United States Patent
Wang et al.

(10) Patent No.: US 6,436,107 B1
(45) Date of Patent: Aug. 20, 2002

(54) METHOD AND APPARATUS FOR PERFORMING MINIMALLY INVASIVE SURGICAL PROCEDURES

(75) Inventors: Yulun Wang, Goleta; Darrin Uecker, Santa Barbara; Keith Laby, Santa Barbara; Jeff Wilson, Santa Barbara; Charles Jordan, Santa Barbara; James Wright, Santa Barbara; Modjtaba Ghodoussi, Santa Barbara, all of CA (US)

(73) Assignee: Computer Motion, Inc., Goleta, CA (US)

( * ) Notice: Subject to any disclaimer, the term of this patent is extended or adjusted under 35 U.S.C. 154(b) by 0 days.

(21) Appl. No.: 09/262,134

(22) Filed: Mar. 3, 1999

Related U.S. Application Data

(63) Continuation-in-part of application No. 09/156,994, filed on Sep. 18, 1998, now Pat. No. 6,063,095, which is a continuation-in-part of application No. 08/900,382, filed on Jul. 12, 1997, now abandoned, which is a continuation-in-part of application No. 08/814,811, filed on Mar. 10, 1997, now abandoned, and a continuation-in-part of application No. 08/755,063, filed on Nov. 22, 1996, which is a continuation-in-part of application No. 08/603,543, filed on Feb. 20, 1996, now Pat. No. 5,762,458.

(51) Int. Cl.[7] ............................................. A61B 17/04

(52) U.S. Cl. ...................... 606/139; 318/568.11; 901/8

(58) Field of Search ................... 606/139, 147, 606/1; 395/80, 92; 128/898; 318/568.11; 414/2; 901/9; 700/245, 251

(56) References Cited

U.S. PATENT DOCUMENTS

| 977,825 A | 12/1910 | Murphy |
| 1,327,577 A | * 1/1920 | Turner ........................ 606/147 |
| 3,171,549 A | 3/1965 | Orloff |

(List continued on next page.)

FOREIGN PATENT DOCUMENTS

| DE | U 9204118.3 | 7/1992 |
| DE | 4310842 C2 | 1/1995 |

(List continued on next page.)

OTHER PUBLICATIONS

Transcript of a video presented by SRI at the 3rd World Congress of Endoscopic Surgery in Bordeaux on Jun. 18–20, 1992, in Washington on Apr. 9, 1992, and in San Diego, CA on Jun. 4–7, 1992 entitled "Telepresence Surgery—The Future of Minimally Invasive Medicine".

(List continued on next page.)

Primary Examiner—Gary Jackson
(74) Attorney, Agent, or Firm—Irell & Manella, LLP

(57) ABSTRACT

A surgical system that may include a remotely controlled surgical instrument. The surgical instrument may be coupled to a tool driver that can spin and actuate the instrument. The instrument may include an actuator rod that is coupled to an end effector and detachably connected to a push rod. The push rod can move relative to the handle to actuate the end effector. The end effector may include a fixture that conforms to the shape of a needle. The handle can be secured to the tool driver by inserting pins into corresponding slots that are located on both the instrument and the tool driver. The instrument can be controlled by an operator through a pair of handles. Each handle may be mechanically balanced by a counterweight. The surgical system may also include a touchpad that allows the operator to enter parameters of the system.

29 Claims, 33 Drawing Sheets

U.S. PATENT DOCUMENTS

| | | |
|---|---|---|
| 3,280,991 A | 10/1966 | Melton et al. |
| 4,058,001 A | 11/1977 | Waxman |
| 4,128,880 A | 12/1978 | Cray, Jr. |
| 4,221,997 A | 9/1980 | Flemming |
| 4,367,998 A | 1/1983 | Causer |
| 4,401,852 A | 8/1983 | Noso et al. |
| 4,456,961 A | 6/1984 | Price et al. |
| 4,460,302 A | 7/1984 | Moreau et al.. |
| 4,474,174 A | 10/1984 | Petruzzi |
| 4,491,135 A | 1/1985 | Klein |
| 4,503,854 A | 3/1985 | Jako |
| 4,517,963 A | 5/1985 | Michel |
| 4,523,884 A | 6/1985 | Clement et al. |
| 4,586,398 A | 5/1986 | Yindra |
| 4,604,016 A | 8/1986 | Joyce |
| 4,616,637 A | 10/1986 | Caspari et al. |
| 4,624,011 A | 11/1986 | Watanabe et al. |
| 4,633,389 A | 12/1986 | Tanaka et al. |
| 4,635,292 A | 1/1987 | Mori et al. |
| 4,641,292 A | 2/1987 | Tunnell et al. |
| 4,655,257 A | 4/1987 | Iwashita |
| 4,672,963 A | 6/1987 | Barken |
| 4,676,243 A | 6/1987 | Clayman |
| 4,728,974 A | 3/1988 | Nio et al. |
| 4,762,455 A | 8/1988 | Coughlan et al. |
| 4,791,934 A | 12/1988 | Brunnett |
| 4,791,940 A | 12/1988 | Hirschfeld et al. |
| 4,794,912 A | 1/1989 | Lia |
| 4,815,006 A | 3/1989 | Anderson et al. |
| 4,815,450 A | 3/1989 | Patel |
| 4,837,734 A | 6/1989 | Ichikawa et al. |
| 4,852,083 A | 7/1989 | Niehaus et al. |
| 4,853,874 A | 8/1989 | Iwamoto et al. |
| 4,854,301 A | 8/1989 | Nakajima |
| 4,860,215 A | 8/1989 | Seraji |
| 4,863,133 A | 9/1989 | Bonnell |
| 4,883,400 A | 11/1989 | Kuban et al. |
| 4,930,494 A | 6/1990 | Takehana et al. |
| 4,945,479 A | 7/1990 | Rusterholz et al. |
| 4,949,717 A | 8/1990 | Shaw |
| 4,954,952 A | 9/1990 | Ubhayakar et al. |
| 4,965,417 A | 10/1990 | Massie |
| 4,969,709 A | 11/1990 | Sogawa et al. |
| 4,969,890 A | 11/1990 | Sugita et al. |
| 4,979,933 A | 12/1990 | Runge |
| 4,979,949 A | 12/1990 | Matsen, III et al. |
| 4,980,626 A | 12/1990 | Hess et al. |
| 4,989,253 A | 1/1991 | Liang et al. |
| 4,996,975 A | 3/1991 | Nakamura |
| 5,019,968 A | 5/1991 | Wang et al. |
| 5,020,001 A | 5/1991 | Yamamoto et al. |
| 5,065,741 A | 11/1991 | Uchiyama et al. |
| 5,078,140 A | 1/1992 | Kwoh |
| 5,086,401 A | 2/1992 | Glassman et al. |
| 5,091,656 A | 2/1992 | Gahn |
| 5,097,829 A | 3/1992 | Quisenberry |
| 5,097,839 A | 3/1992 | Allen |
| 5,098,426 A | 3/1992 | Sklar et al. |
| 5,105,367 A | 4/1992 | Tsuchihashi et al. |
| 5,109,499 A | 4/1992 | Inagami et al. |
| 5,123,095 A | 6/1992 | Papadopulos et al. |
| 5,131,105 A | 7/1992 | Harrawood et al. |
| 5,142,930 A | 9/1992 | Allen et al. |
| 5,145,227 A | 9/1992 | Monford, Jr. |
| 5,166,513 A | 11/1992 | Keenan et al. |
| 5,175,694 A | 12/1992 | Amato |
| 5,182,641 A | 1/1993 | Diner et al. |
| 5,184,601 A | 2/1993 | Putman |
| 5,187,574 A | 2/1993 | Kosemura et al. |
| 5,196,688 A | 3/1993 | Hesse et al. |
| 5,201,325 A | 4/1993 | McEwen et al. |
| 5,201,743 A | 4/1993 | Haber et al. |
| 5,217,003 A | 6/1993 | Wilk |
| 5,221,283 A | 6/1993 | Chang |
| 5,228,429 A | 7/1993 | Hatano |
| 5,230,623 A | 7/1993 | Guthrie et al. |
| 5,236,432 A | 8/1993 | Matsen, III et al. |
| 5,251,127 A | 10/1993 | Raab |
| 5,257,999 A | 11/1993 | Slanetz, Jr. |
| 5,271,384 A | 12/1993 | McEwen et al. |
| 5,279,309 A | 1/1994 | Taylor et al. |
| 5,282,806 A * | 2/1994 | Harber et al. ............... 606/139 |
| 5,289,273 A | 2/1994 | Lang |
| 5,289,365 A | 2/1994 | Caldwell et al. |
| 5,299,288 A | 3/1994 | Glassman et al. |
| 5,300,926 A | 4/1994 | Stoeckl |
| 5,303,148 A | 4/1994 | Mattson et al. |
| 5,304,185 A | 4/1994 | Taylor |
| 5,305,203 A | 4/1994 | Raab |
| 5,305,427 A | 4/1994 | Nagata |
| 5,309,717 A | 5/1994 | Minch |
| 5,313,306 A | 5/1994 | Kuban et al. |
| 5,320,630 A | 6/1994 | Ahmed |
| 5,337,732 A | 8/1994 | Grundfest et al. |
| 5,339,799 A | 8/1994 | Kami et al. |
| 5,343,385 A | 8/1994 | Joskowicz et al. |
| 5,343,391 A | 8/1994 | Mushabac |
| 5,345,538 A | 9/1994 | Narayannan et al. |
| 5,357,962 A | 10/1994 | Green |
| 5,368,015 A | 11/1994 | Wilk |
| 5,368,428 A | 11/1994 | Hussey et al. |
| 5,371,536 A | 12/1994 | Yamaguchi |
| 5,382,885 A | 1/1995 | Salcudean et al. |
| 5,388,987 A | 2/1995 | Badoz et al. |
| 5,395,369 A | 3/1995 | McBrayer et al. |
| 5,397,323 A | 3/1995 | Taylor et al. |
| 5,402,801 A | 4/1995 | Taylor |
| 5,403,319 A | 4/1995 | Matsen, III et al. |
| 5,408,409 A | 4/1995 | Glassman et al. |
| 5,410,638 A | 4/1995 | Colgate et al. |
| 5,417,210 A | 5/1995 | Funda et al. |
| 5,417,701 A | 5/1995 | Holmes |
| 5,422,521 A | 6/1995 | Neer et al. |
| 5,431,645 A | 7/1995 | Smith et al. |
| 5,434,457 A | 7/1995 | Josephs et al. |
| 5,442,728 A | 8/1995 | Kaufman et al. |
| 5,445,166 A | 8/1995 | Taylor |
| 5,451,924 A | 9/1995 | Massimino et al. |
| 5,455,766 A | 10/1995 | Scheller et al. |
| 5,458,547 A | 10/1995 | Teraoka et al. |
| 5,458,574 A | 10/1995 | Machold et al. |
| 5,476,010 A | 12/1995 | Fleming et al. |
| 5,490,117 A | 2/1996 | Oda et al. |
| 5,506,912 A | 4/1996 | Nagasaki et al. |
| 5,512,919 A | 4/1996 | Araki |
| 5,515,478 A | 5/1996 | Wang |
| 5,544,654 A | 8/1996 | Murphy et al. |
| 5,553,198 A | 9/1996 | Wang et al. |
| 5,562,503 A | 10/1996 | Ellman et al. |
| 5,571,110 A | 11/1996 | Matsen, III et al. |
| 5,572,999 A | 11/1996 | Funda et al. |
| 5,609,560 A | 3/1997 | Ichikawa et al. |
| 5,626,595 A | 5/1997 | Sklar et al. |
| 5,629,594 A | 5/1997 | Jacobus et al. |
| 5,630,431 A | 5/1997 | Taylor |
| 5,631,973 A | 5/1997 | Green |
| 5,636,259 A | 6/1997 | Khutoryansky et al. |
| 5,649,956 A | 7/1997 | Jensen et al. |
| 5,657,429 A | 8/1997 | Wang et al. |
| 5,658,250 A | 8/1997 | Blomquist et al. |
| 5,676,673 A | 10/1997 | Ferre et al. |

| | | |
|---|---|---|
| 5,695,500 A | 12/1997 | Taylor et al. |
| 5,696,574 A | 12/1997 | Schwaegerle |
| 5,696,837 A | 12/1997 | Green |
| 5,718,038 A | 2/1998 | Takiar et al. |
| 5,727,569 A | 3/1998 | Benetti et al. |
| 5,735,290 A | 4/1998 | Sterman et al. |
| 5,737,711 A | 4/1998 | Abe |
| 5,749,362 A | 5/1998 | Funda et al. |
| 5,754,741 A | 5/1998 | Wang et al. |
| 5,762,458 A | 6/1998 | Wang et al. |
| 5,766,126 A | 6/1998 | Anderson |
| 5,776,126 A | 7/1998 | Wilk et al. |
| 5,779,623 A | 7/1998 | Bonnell |
| 5,792,135 A | 8/1998 | Madhani et al. |
| 5,792,178 A | 8/1998 | Welch et al. |
| 5,797,900 A | 8/1998 | Madhani et al. |
| 5,800,423 A | 9/1998 | Jensen |
| 5,807,284 A | 9/1998 | Foxlin |
| 5,807,377 A | 9/1998 | Madhani et al. |
| 5,807,378 A | 9/1998 | Jensen et al. |
| 5,808,665 A | 9/1998 | Green |
| 5,810,880 A | 9/1998 | Jensen et al. |
| 5,813,813 A | 9/1998 | Daum et al. |
| 5,814,038 A | 9/1998 | Jensen et al. |
| 5,817,084 A | 10/1998 | Jensen |
| 5,825,982 A | 10/1998 | Wright et al. |
| 5,836,869 A | 11/1998 | Kudo et al. |
| 5,844,824 A | 12/1998 | Newman et al. |
| 5,855,583 A | 1/1999 | Wang et al. |
| 5,859,934 A | 1/1999 | Green |
| 5,860,995 A | 1/1999 | Berkelaar |
| 5,876,325 A | 3/1999 | Mizuno et al. |
| 5,878,193 A | 3/1999 | Wang et al. |
| 5,882,206 A | 3/1999 | Gillio |
| 5,887,121 A | 3/1999 | Funda et al. |
| 5,904,702 A | 5/1999 | Ek et al. |
| 5,906,630 A | 5/1999 | Anderhub et al. |
| 5,931,832 A | 8/1999 | Jensen |
| 5,950,629 A | 9/1999 | Taylor et al. |
| 5,951,475 A | 9/1999 | Gueziec et al. |
| 5,951,587 A | 9/1999 | Qureshi et al. |
| 5,954,731 A | 9/1999 | Yoon |
| 5,980,782 A | 11/1999 | Hershkowitz et al. |
| 5,984,932 A | 11/1999 | Yoon |
| 6,024,695 A | 2/2000 | Taylor et al. |
| 6,120,433 A | 9/2000 | Mizuno et al. |

FOREIGN PATENT DOCUMENTS

| | | |
|---|---|---|
| EP | 0239409 A1 | 9/1987 |
| EP | 0424687 A1 | 5/1991 |
| EP | 0 776 738 A2 | 6/1997 |
| WO | WO 91/04711 | 4/1991 |
| WO | WO 92/20295 | 11/1992 |
| WO | WO 93/13916 | 7/1993 |
| WO | WO 94/18881 | 9/1994 |
| WO | WO 94/26167 | 11/1994 |
| WO | WO 97/15240 | 5/1997 |
| WO | WO 98/25666 | 6/1998 |

OTHER PUBLICATIONS

Statutory Declaration of Dr. Philip S. Green, presenter of the video entitled "Telepresence Surgery—The Future of Minimally Invasive Medicine".

Abstract of a presentation "Telepresence: Advanced Teleoperator Technology for Minimally Invasive Surgery" (P. Green et al.) given at the 3rd World Congress of Endoscopic Surgery in Bordeaux, Jun. 18–20, 1992.

Abstract of a presentation "Telepresence: Advanced Teleoperator Technology for Minimally Invasive Surgery", (P. Green et al.) given at "Medicine meets virtual reality" symposium in San Diego, Jun. 4–7, 1992.

Abstract of a presentation "Camera Control for Laparoscopic Surgery by Speech–Recognizing Robot: Constant Attention and Better Use of Personnel" (Colin Besant et al.) given at the 3rd World Congress of Endoscopic Surgery in Bordeaux, Jun. 18–20, 1992.

"A Literature Review: Robots in Medicine" (B. Preising et al.) IEEE Jun. 1991.

"Robots for the Operating Room" (Elizabeth Corcoran), The New York Times, Sunday Jul. 19, 1992, Section 3, p. 9, col. 1.

"Taming the Bull: Safety in a Precise Surgical Robot" (Russell H. Taylor et al.), IEEE 1991.

Abstract of a presentation "Design Considerations of a New Generation Endoscope Using Robotics and Computer Vision Technology" (S.M. Krishnan et al.) given at the 3rd World Congress of Endoscopic Surgery in Bordeaux, Jun. 18–20, 1992.

Abstract of a presentation "3–D Vision Technology Applied to Advanced Minimally Invasive Surgery Systems" given at the 3rd World Congress of Endoscopic Surgery in Bordeaux, Jun. 18–20, 1992.

"Analysis of the Surgeon's Grasp for Telerobotic Surgical Manipulation" (Frank Tendick and Lawrence Stark), IEEE 1989.

"Kinematic Control and Visual Display of Redundant Teleoperators" (Hardi Das et al.), IEEE 1989.

"A New System for Computer Assisted Neurosurgery" (S. Lavallee), IEEE 1989.

"An Advanced Control Micromanipulator for Surgical Applications" (Ben Gayed et al.), Systems Science vol. 13 1987.

"Force Feedback–Based Telemicromanipulation for Robot Surgery on Soft Tissues" (A.M. Sabatini et al.), IEEE 1989.

"Six–Axis Bilateral Control of an Articulated Slave Manipulator Using a Cartesian Master Manipulator" (Masao Inoue), Advanced Robotics 1990.

"On a Micro–Manipulator for Medical Application—Stability Consideration of its Bilateral Controller" (S. Majima et al.), Mechatronics 1991.

"Anthropomorphic Remote Manipulator", NASA Tech Briefs 1991.

"Controlling Remote Manipulators through Kinesthetic Coupling" (A.K. Bejczy), Computers in Mechanical Engineering 1983.

"Design of a Surgeon–Machine Interface for Teleoperated Microsurgery" (Steve Charles M.D. et al.), IEEE 1989.

"A Robot in an Operating Room: A Bull in a China Shop" (J.M. Dolan et al.), IEEE 1987.

Abstract of a presentation "Concept and Experimental Application of a Surgical Robotic System the Steerable MIS Instrument SMI" given at the 3rd World Congress of Endoscopic Surgery in Bordeaux, Jun. 18–20, 1992.

Abstract of a presentation given at the 3rd World Congress of Endoscopic Surgery in Bordeaux, Jun. 18–20, 1992, entitled "Session 15/1".

Abstract of a presentation "A Pneumatic Controlled Sewing Device for Endoscopic Application the MIS Sewing Instrument MSI" given at the 3rd World Congress of Endoscopic Surgery in Bordeaux, Jun. 18–20, 1992.

Abstract of a presentation given at the 3rd World Congress of Endoscopic Surgery in Bordeaux (Jun. 18 to 20, 1992), entitled "Session 15/2".

Abstract of a presentation given at the 3rd World Congress of Endoscopic Surgery in Bordeaux (Jun. 18 to 20, 1992), entitled Session 15/4.

Abstract of a presentation given at the 3rd World Congress of Endoscopic Surgery in Bordeaux (Jun. 18 to 20, 1992), entitled "Session 15/5".

"Properties of Master–Slave Robots" (C. Vibet), Motor–con 1987.

"A New Microsurgical Robot System for Corneal Transplantation" (Noriyuki Tejima), Precision Machinery 1988.

"Human/Robot Interaction via the Transfer of Power and Information Signals—Part I: Dynamics and Control Analysis" (H. Kazerooni), IEEE 1989.

"Human/Robot Interaction via the Transfer of Power and Information Signals—Part II: An Experimental Analysis" (H. Kazerooni), IEEE 1989.

"Power and Impedance Scaling in Bilateral Manipulation" (J. Edward Colgate), IEEE 1991.

"S.M.O.S.: Stereotaxical Microtelemanipulator for Ocular Surgery" (Aicha Guerrouad and Pierre Vidal), IEEE 1989.

"Motion Control for a Sheep Shearing Robot" (James P. Trevelyan et al.), Proceedings of the 1st International Symposium on Robotics Research, MIT, Cambridge, Massachusetts, USA, 1983.

"Robots and Telechirs" (M.W. Thring), Wiley 1983.

Industrial Robotics (Gordon M. Mair), Prentice Hall 1988 (pp. 41–43, 49–50, 54, 203–209 enclosed).

"Student Reference Manual for Electronic Instrumentation Laboratories" (Wolf et al.), Prentice Hall, New Jersey 1990, pp. 498 amd 499.

"Surgery in Cyberspace" (Taubes), Discover Magazine, Dec. 1994.

* cited by examiner

CORONARY ARTERY

INTERNAL MAMMARY ARTERY

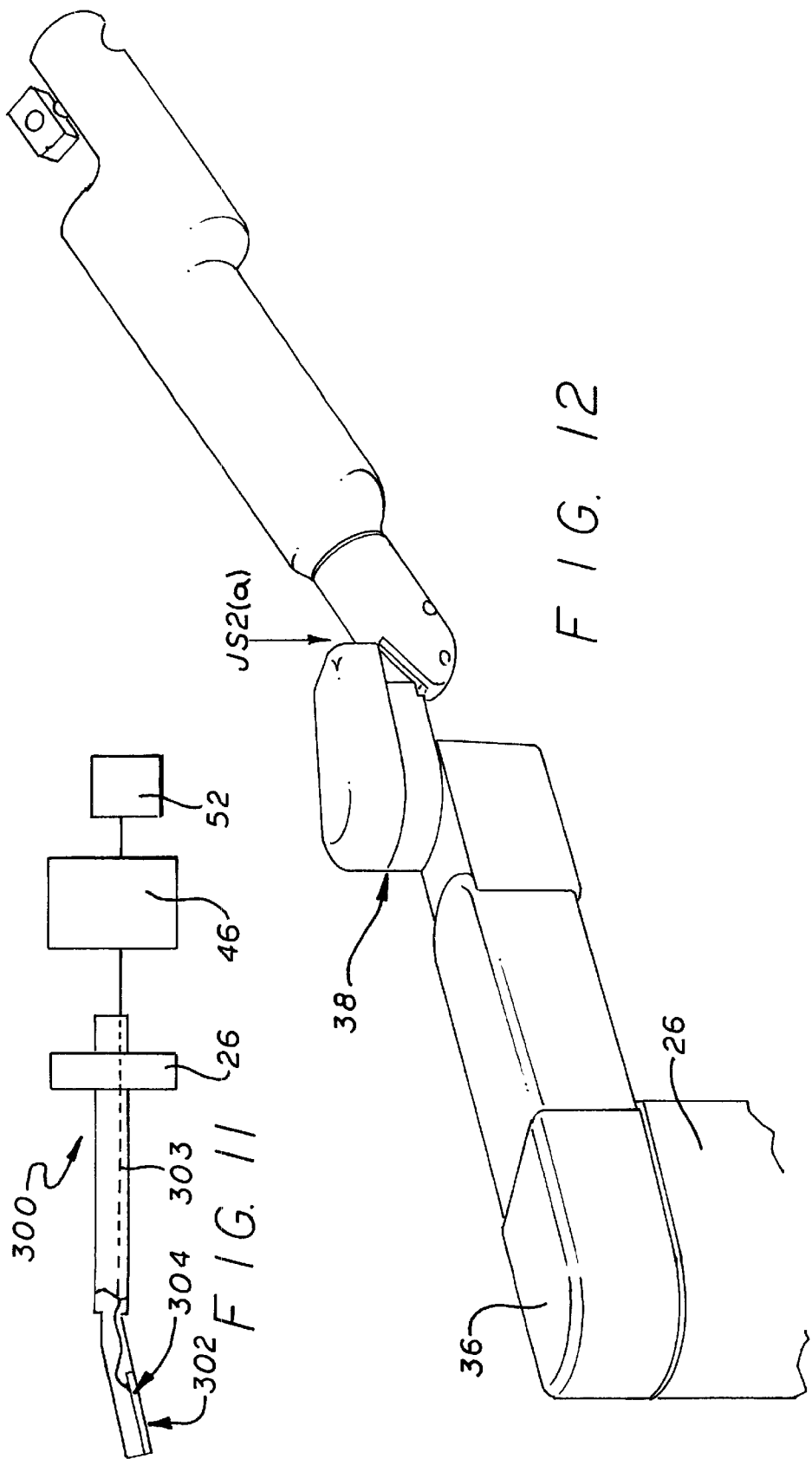

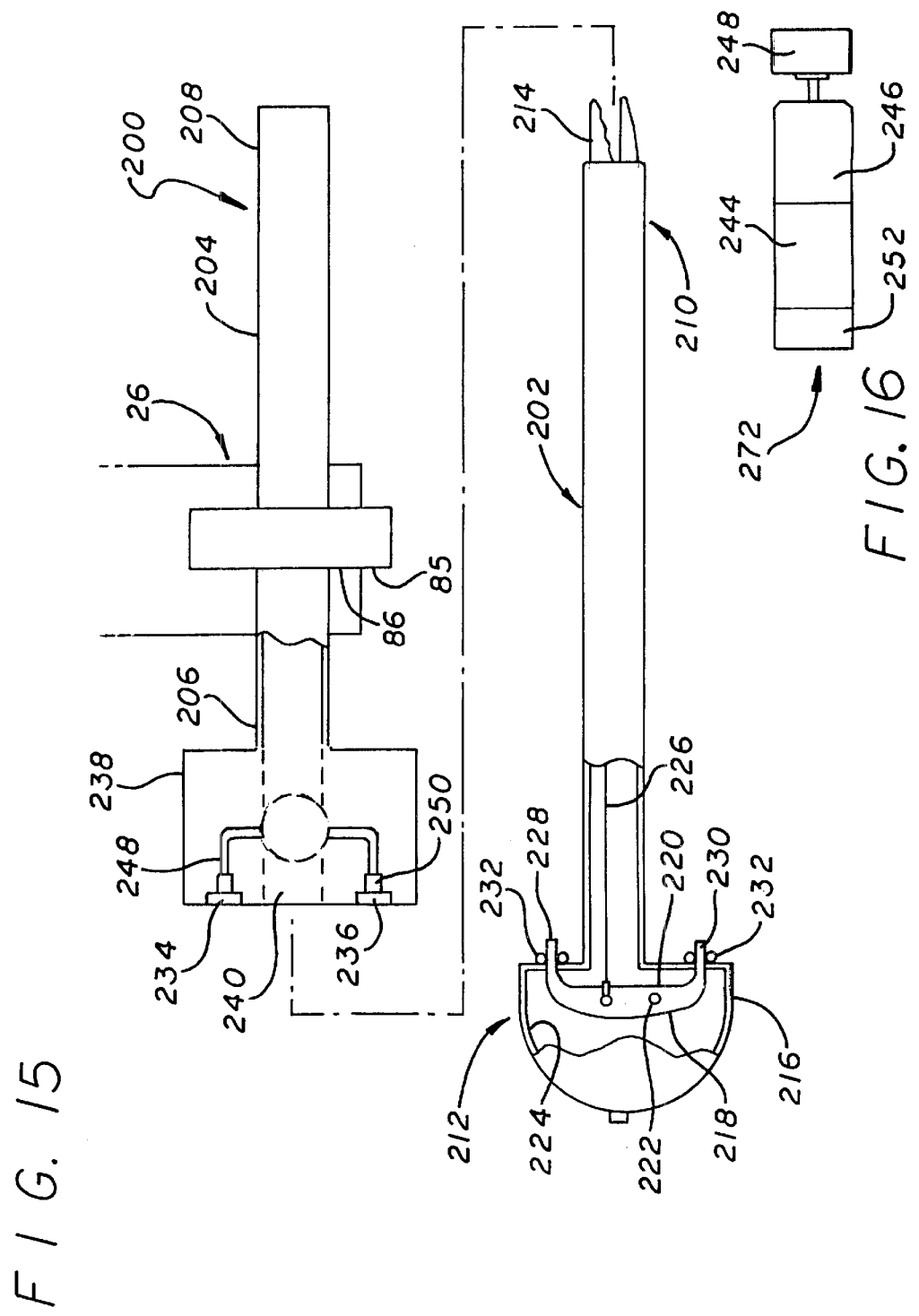

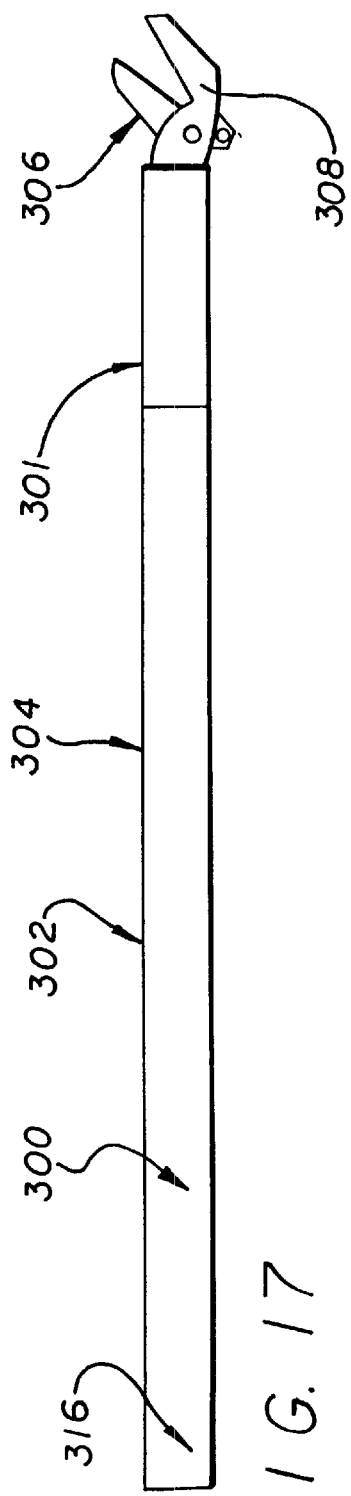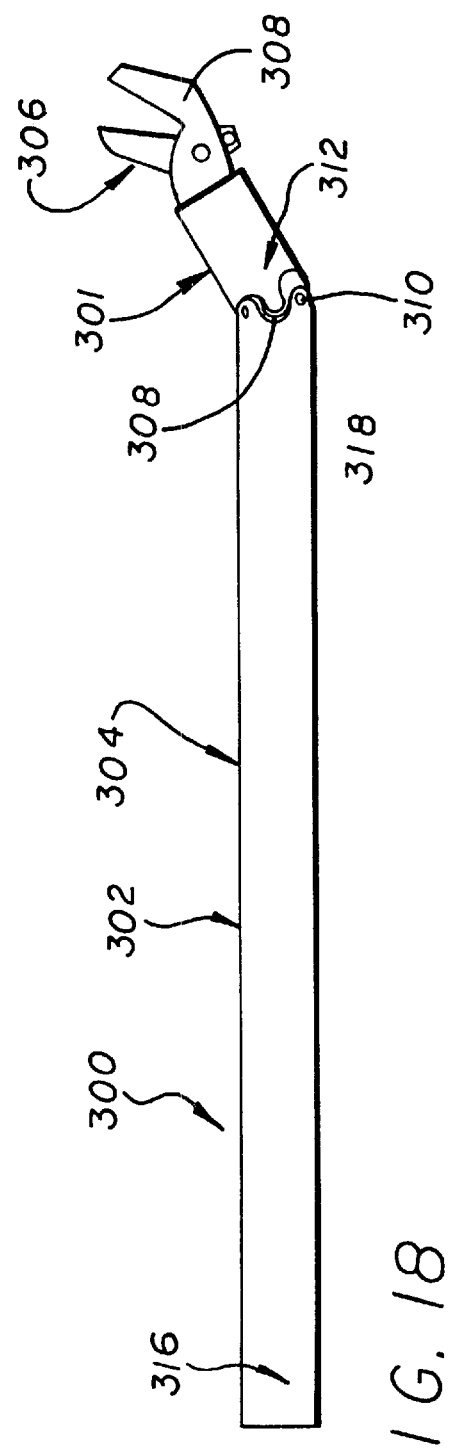

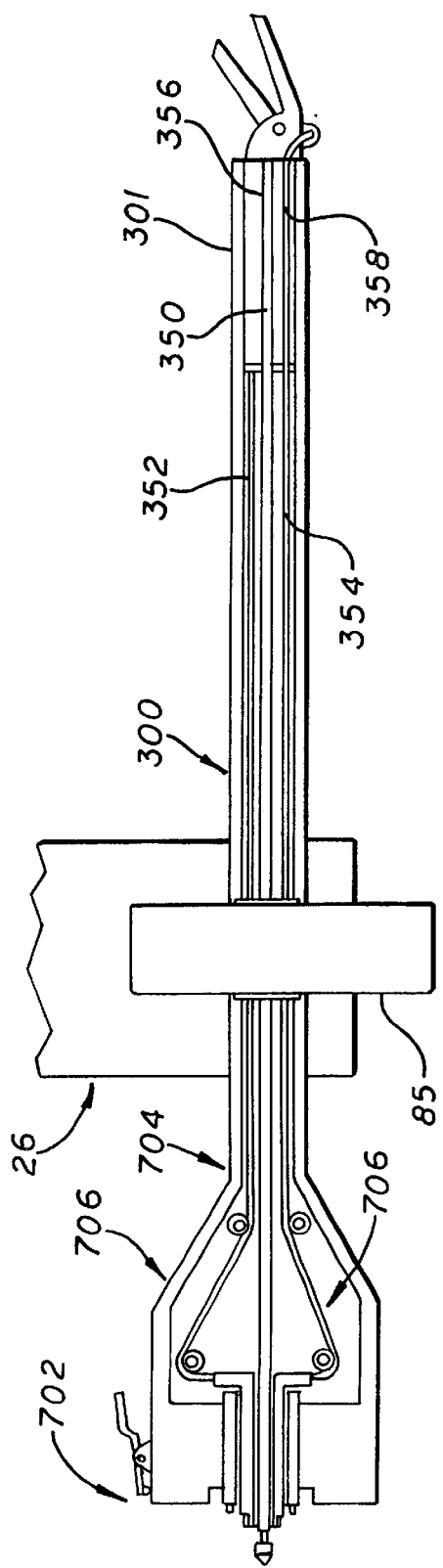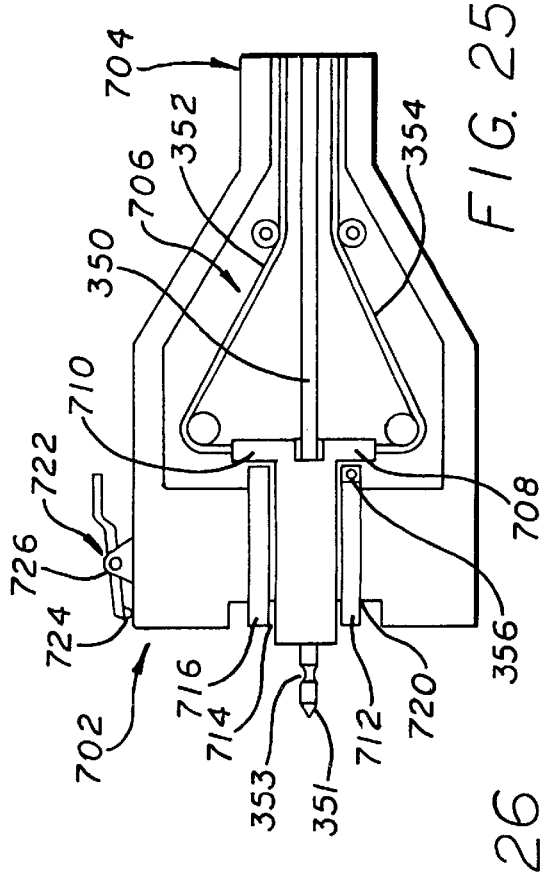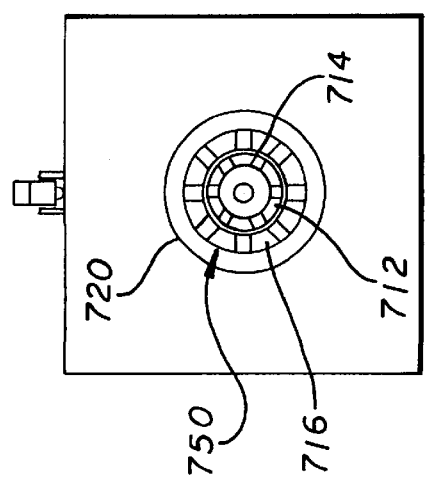

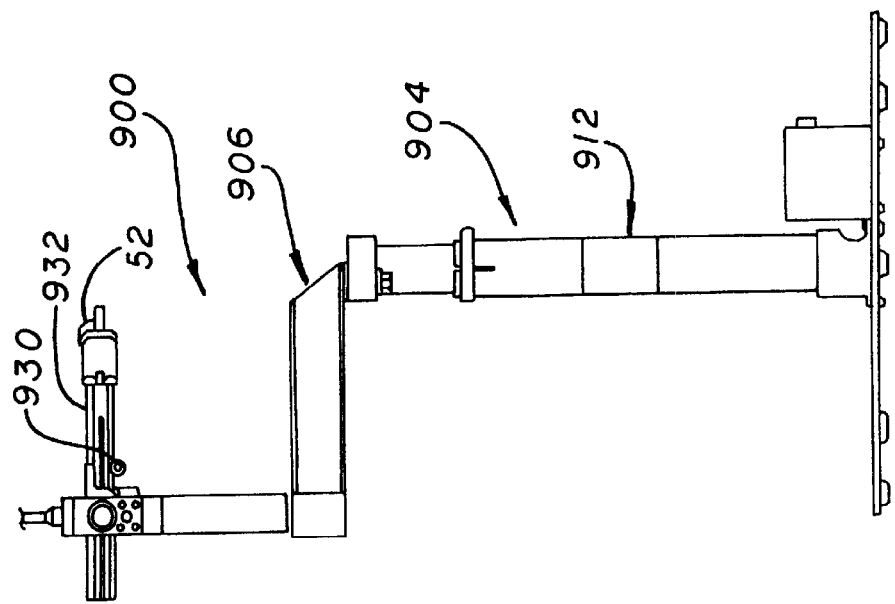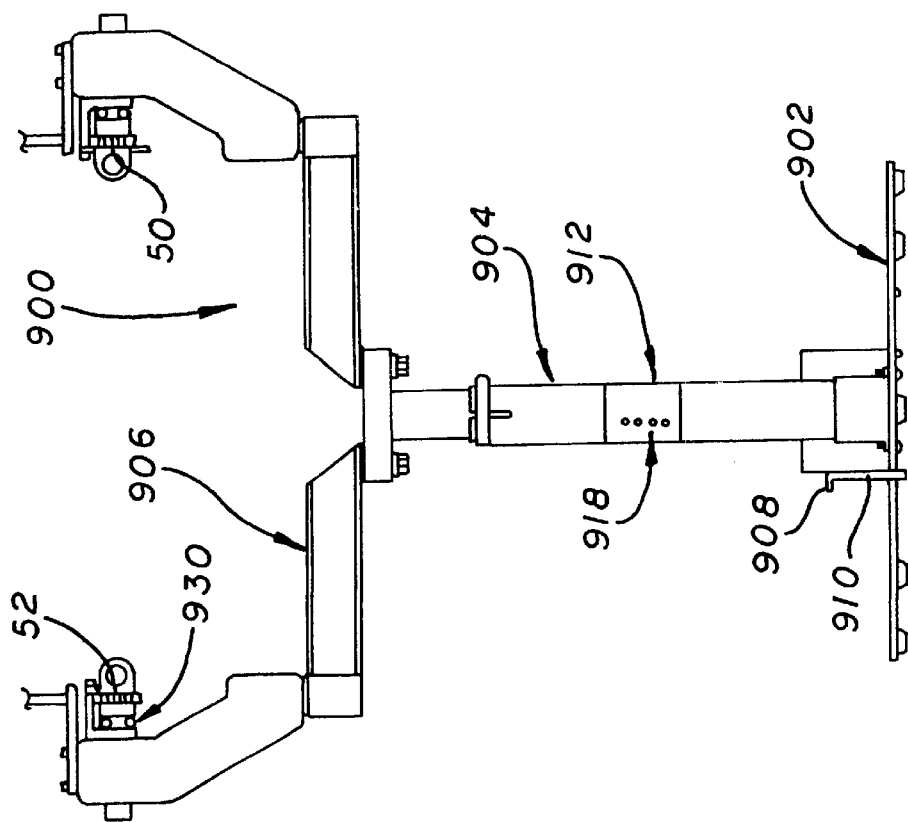

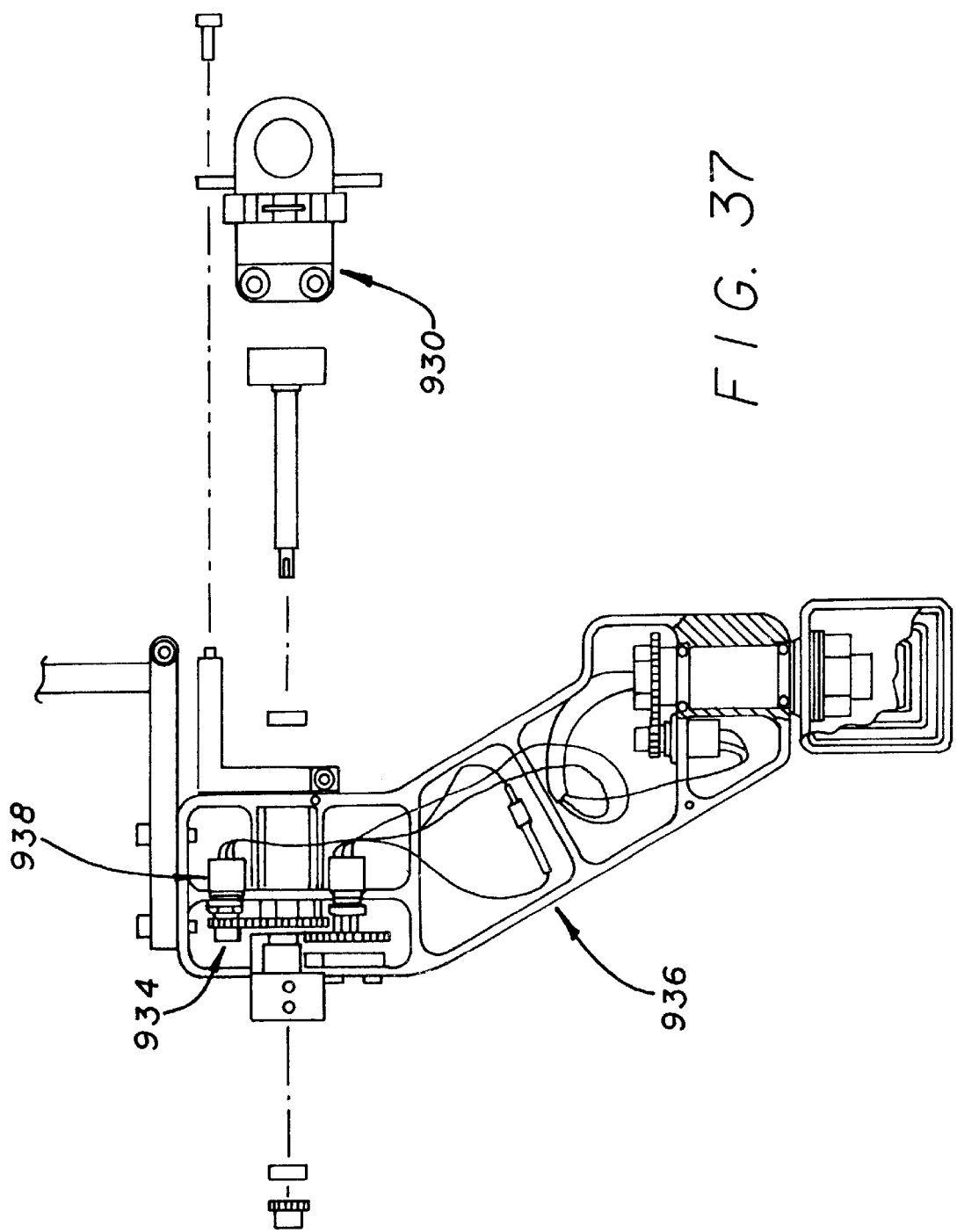

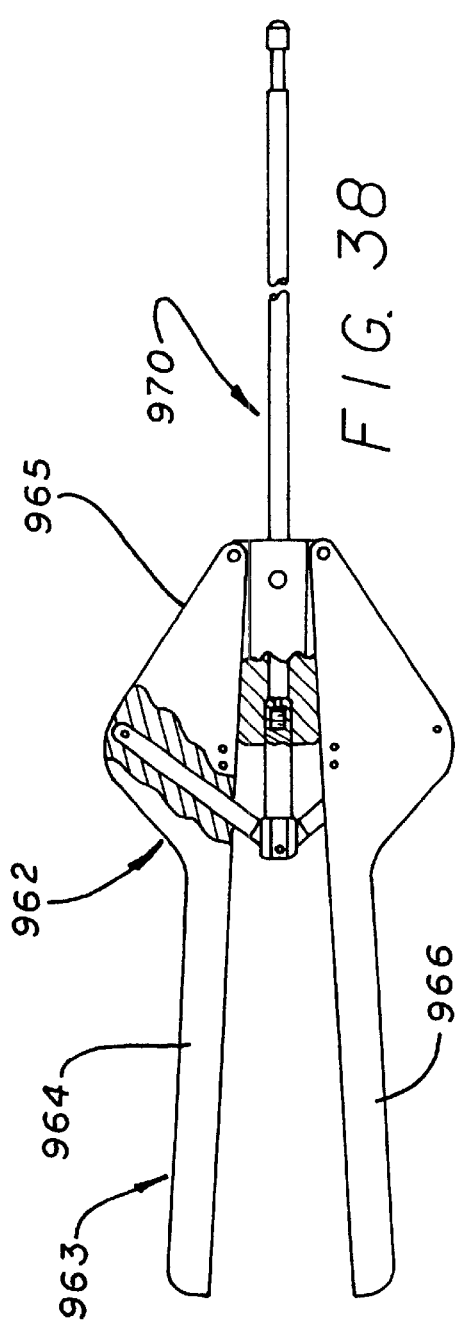
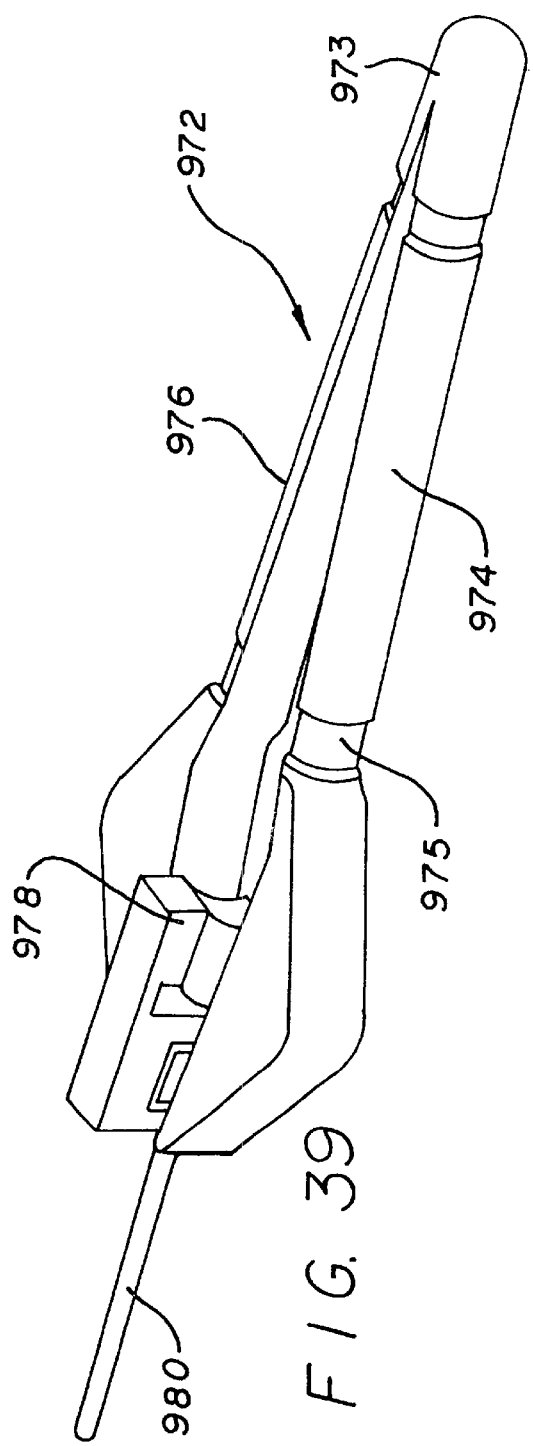

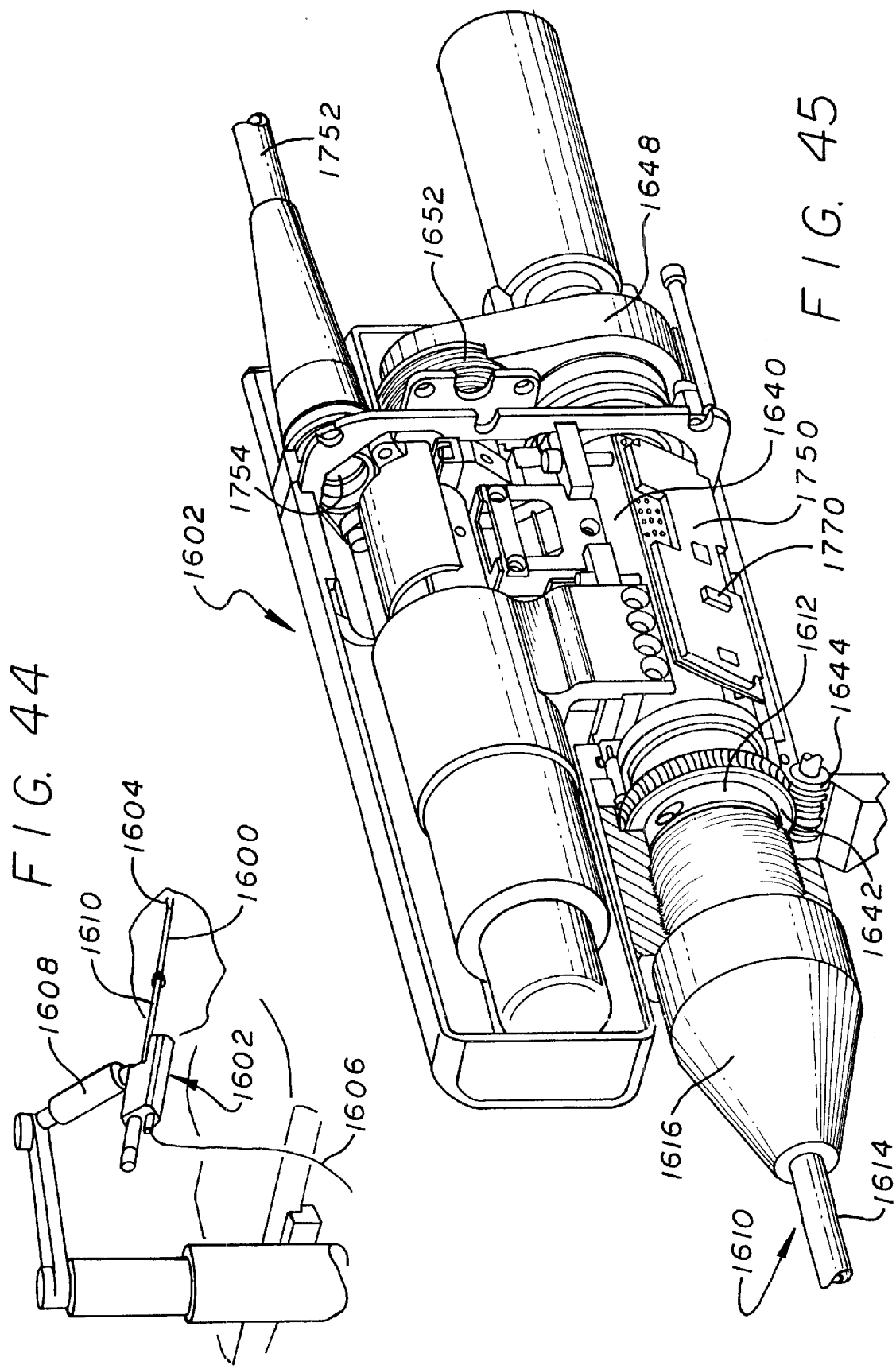

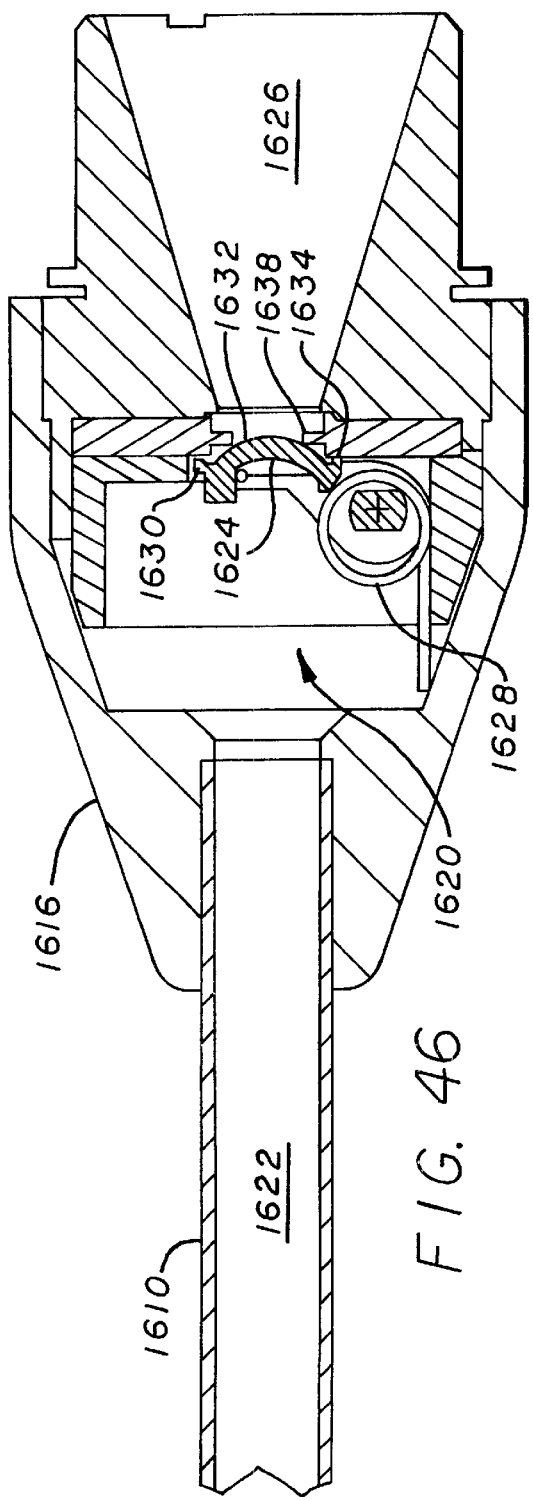
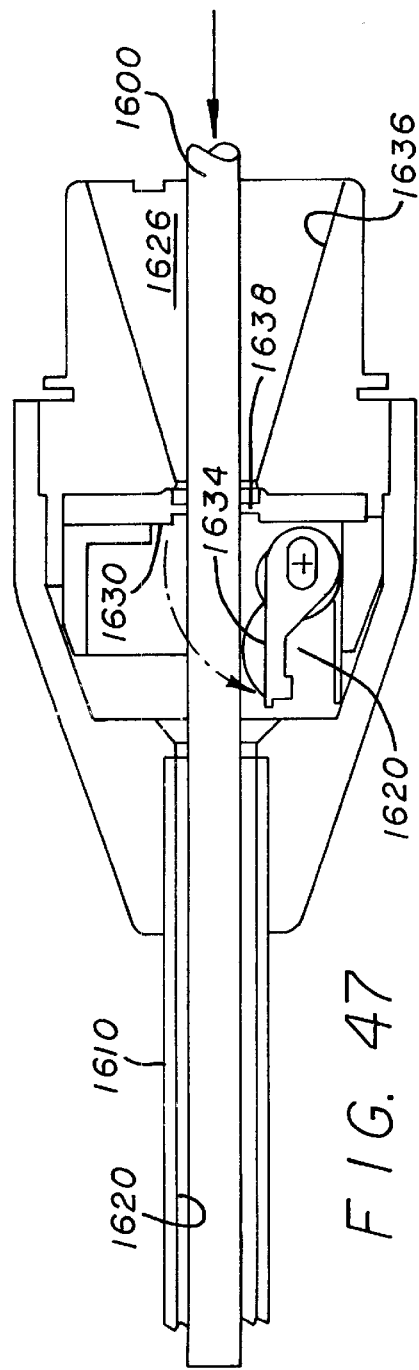
FIG. 46
FIG. 47

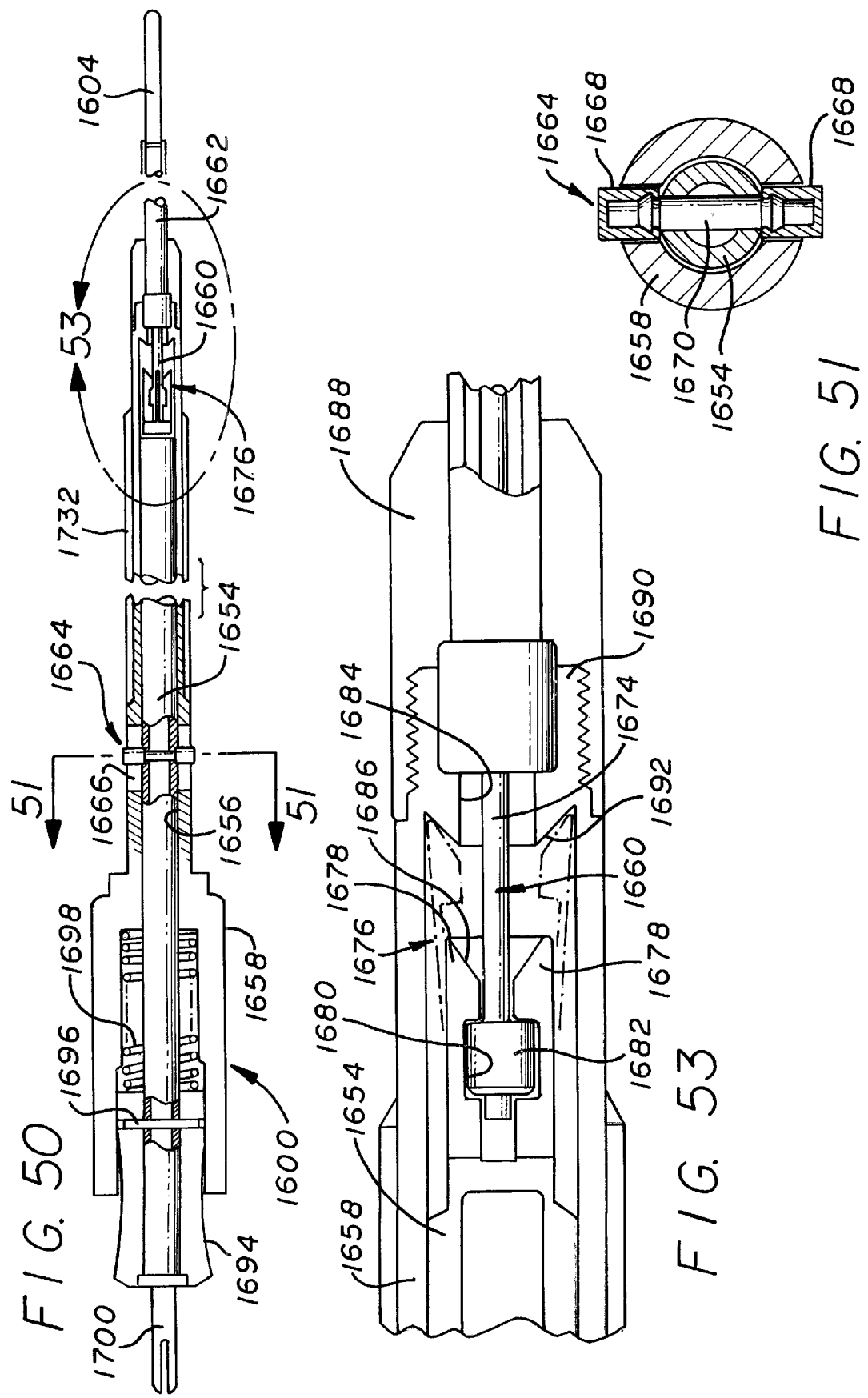

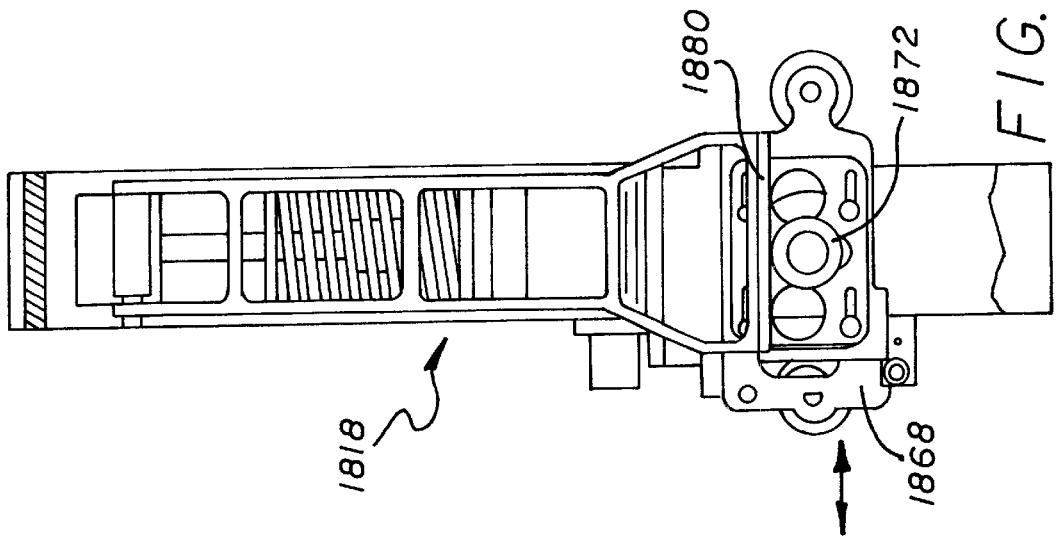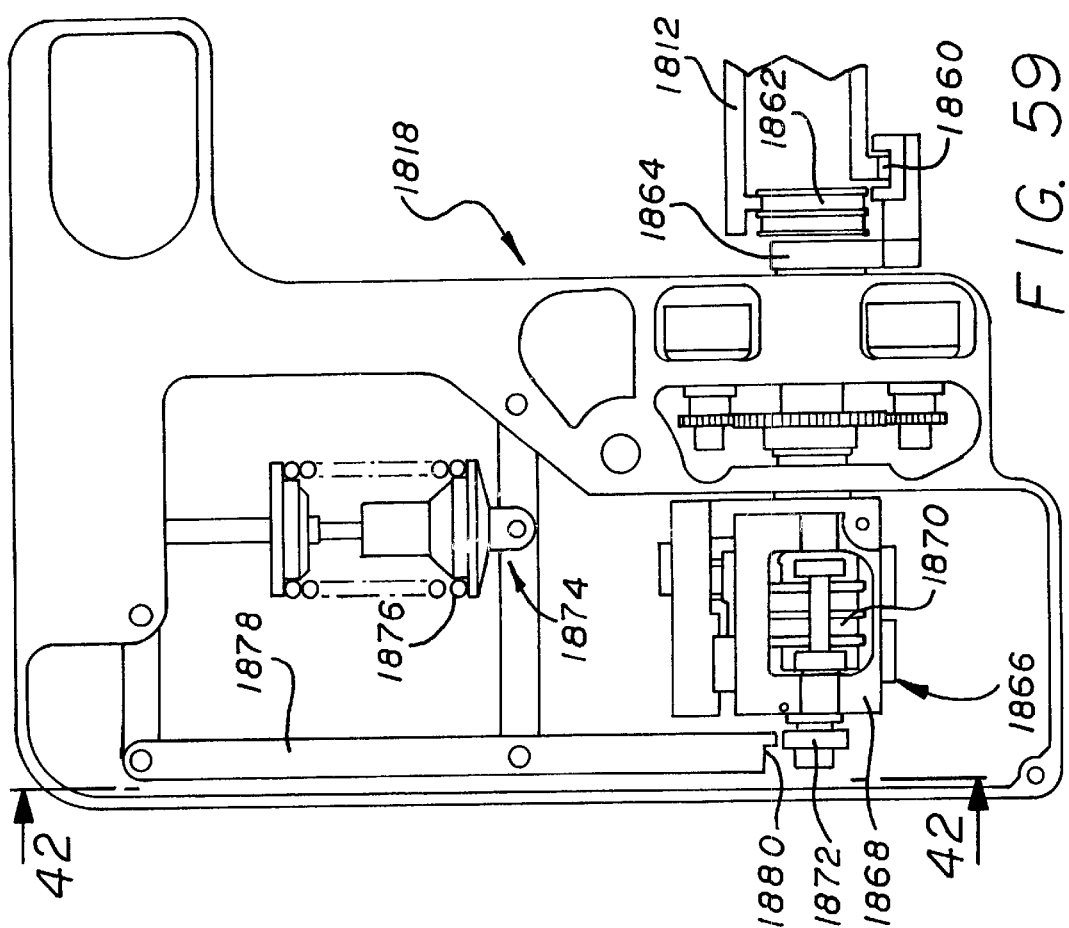

METHOD AND APPARATUS FOR PERFORMING MINIMALLY INVASIVE SURGICAL PROCEDURES

CROSS-REFERENCE TO RELATED APPLICATIONS

This application is a continuation-in-part of application Ser. No. 09/156,994, filed Sep. 18, 1998, now U.S. Pat. No. 6,063,095, which is a continuation-in-part of application Ser. No. 08/900,382, filed Jul. 12, 1997 now abandoned, which is a continuation-in-part of application Ser. No. 08/814,811, filed Mar. 10, 1997, abandoned in favor of a confutation application entitled "A Method and Apparatus for Performing Minimally Invasive Surgical Procedures", filed Nov. 3, 1998, which has not received a U.S. Application Number and is also a continuation-in-part of U.S. Ser. No. 08/755,063, filed Nov. 22, 1996, allowed, which is a continuation-in-part of application Ser. No. 08/603,543, filed Feb. 20, 1996, now U.S. Pat. No. 5,762,458.

BACKGROUND OF THE INVENTION

1. Field of the Invention

The present invention relates to a system and method for performing minimally invasive cardiac procedures. More particularly, the present invention relates to a robotic system and surgical instruments that may be removably attached thereto, wherein said system aids in performing minimally invasive surgical procedures.

2. Background Information

Blockage of a coronary artery may deprive the heart of the blood and oxygen required to sustain life. The blockage may be removed with medication or by an angioplasty. For severe blockage a coronary artery bypass graft (CABG) is performed to bypass the blocked area of the artery. CABG procedures are typically performed by splitting the sternum and pulling open the chest cavity to provide access to the heart. An incision is made in the artery adjacent to the blocked area. The internal mammary artery (IMA) is then severed and attached to the artery at the point of incision. The IMA bypasses the blocked area of the artery to again provide a full flow of blood to the heart. Splitting the sternum and opening the chest cavity, commonly referred to as 'open surgery', can create a tremendous trauma on the patient. Additionally, the cracked sternum prolongs the recovery period of the patient.

There have been attempts to perform CABG procedures without opening the chest cavity. Minimally invasive procedures are conducted by inserting surgical instruments and an endoscope through small incision in the skin of the patient. Manipulating such instruments can be awkward, particularly when suturing a graft to an artery. It has been found that a high level of dexterity is required to accurately control the instruments. Additionally, human hands typically have at least a minimal amount of tremor. The tremor further increases the difficulty of performing minimally invasive cardiac procedures.

To perform MIS, the surgeon uses special instruments. These instruments allow the surgeon to maneuver inside the patient. One type of instrument that is used in minimally invasive surgery is forceps, an instrument having a tip specifically configured to grasp objects, such as needles. Because forceps and other instruments designed for minimally invasive surgery are generally long and rigid, they fail to provide a surgeon the dexterity and precision necessary to effectively carry out many procedures in a minimally invasive fashion. For example, conventional MIS forceps are not well suited for manipulating a needle during a minimally invasive procedure, such as during endoscopy. Therefore, many MIS procedures that might be performed, have, as of yet, not been accomplished.

In essence, during open surgeries, the tips of the various instruments may be positioned with six degrees of freedom. However, by inserting an instrument through a small aperture, such as one made in a patient to effectuate a minimally invasive procedure, two degrees of freedom are lost. It is this loss of freedom of movement within the surgical site that has substantially limited the types of MIS procedures that are performed.

Dexterity is lacking in MIS because the instruments that are used fail to provide the additional degrees of freedom that are lost when the instrument is inserted into a patient. One problem associated with this lack of dexterity is the inability to suture when the instruments are in certain positions. As a result, surgeries that require a great deal of suturing within the surgical site are almost impossible to perform because the surgical instruments to enable much of this work are not available.

Another problem associated with MIS is the lack of precision within the surgical site. For procedures such as the MICABG (Minimally Invasive Coronary Artery Bypass Graft), extremely small sutures must be emplaced in various locations proximate the heart. As such, precise motion of the tool at the tip of a surgical instrument is necessary. Currently, with hand positioned instruments, the precision necessary for such suturing is lacking.

As such, what is needed in the art is a tool and class of surgical instruments that may be articulated within the patient such that a surgeon has additional degrees of freedom available to more dexterously and precisely position the tool at the tip of the instrument, as is needed.

Additionally, what is needed in the art is a method and mechanism that provides simple handle, instrument and tool changing capabilities so that various tools may be easily and readily replaced to enable faster procedures to thus minimize operating room costs to the patient and to lessen the amount of time a patient is under anesthesia.

It is to the solution of the aforementioned problems to which the present invention is directed.

U.S. Pat. No. 5,649,956 issued to Jensen et al. and assigned to SRI International discloses a system for holding a surgical instrument. The system includes an instrument holder that can hold a surgical instrument. The instrument can be inserted into a collar assembly an instrument holder. The instrument has a pair of pins that are rotated into circumferential slots of the collar assembly. The collar assembly further contains a latch which secures one of the pins within a corresponding slot to prevent the instrument from being inadvertently detached from the holder. When installed into the collar assembly the surgical instrument can be rotated and actuated through the holder.

The surgical instrument can be detached from the holder by twisting and then pulling the instrument away from the collar. These steps may require valuable time during a surgical procedure. Additionally, it appears that a cover of the holder must be opened to pull the instrument out of the collar. Opening the cover exposes the mechanism that rotates and actuates the instrument. The exposed mechanism may introduce contaminants into the operating site. It would be desirable to provide an instrument and tool driver which allow an operator to quickly change instruments without introducing contaminates into the surgical site.

SUMMARY OF THE INVENTION

One embodiment of the present invention is a surgical instrument which has an actuator rod that is coupled to an end effector. The actuator rod is also detachably connected to a push rod that can move relative to a handle to actuate the end effector.

BRIEF DESCRIPTION OF THE DRAWINGS

FIG. 8a is a side view of the master handle of the system in accordance with the present invention;

FIG. 11 is a side view of a force feedback tool in accordance with one aspect of the present invention;

FIG. 12 is a perspective view of a robotic arm including an additional joint;

FIG. 15 is a side view of a rear-loading tool driver in accordance with the system of the present invention;

FIG. 16 is a plan view of the motor assembly of the back loading tool driver of FIG. 15;

FIG. 17 is a side plan view of an articulable instrument in accordance with the present invention;

FIG. 18 is a side plan view of an articulable instrument, where the instrument tip is articulated;

FIG. 24 is a cross-sectional view of an articulable instrument attached to the articulate-translator of the present invention;

FIG. 25 is an enlarged cross-sectional view of the articulate-translator in accordance with the present invention;

FIG. 26 is an end view of the articulate translator in accordance with the present invention;

FIG. 35 is a plan view of an alternative master-handle console in accordance the present invention;

FIG. 36 is a plan view of an alternative master-handle console in accordance with the present invention;

FIG. 37 is a partial cut away cross-section of the master handle console in accordance with the present invention;

FIG. 38 is a partial cut-away plan view of a handle in accordance with the present invention;

FIG. 39 is a perspective view of an alternative embodiment of a handle in accordance with the present invention;

FIG. 44 is a perspective view of a tool driver and surgical instrument coupled to an articulate arm;

FIG. 45 is a cross-sectional perspective view of an embodiment of a surgical instrument coupled to a tool driver;

FIG. 46 is a side cross-sectional view of a sheath of the tool driver;

FIG. 47 is a cross-sectional view similar to FIG. 46 showing a surgical instrument inserted into the sheath;

FIG. 50 is a cross-sectional view of an embodiment of a surgical instrument;

FIG. 51 is a cross-sectional view of an actuator pin assembly;

FIG. 52 is a perspective view of a sleeve of the tool holder;

FIG. 53 is an enlarged cross-sectional view showing a connector assembly of the instrument;

FIG. 59 is a cross-sectional view of a swing arm of the handle assembly;

FIG. 60 is a side sectional view of the swing arm;

DETAILED DESCRIPTION

Figure 1:
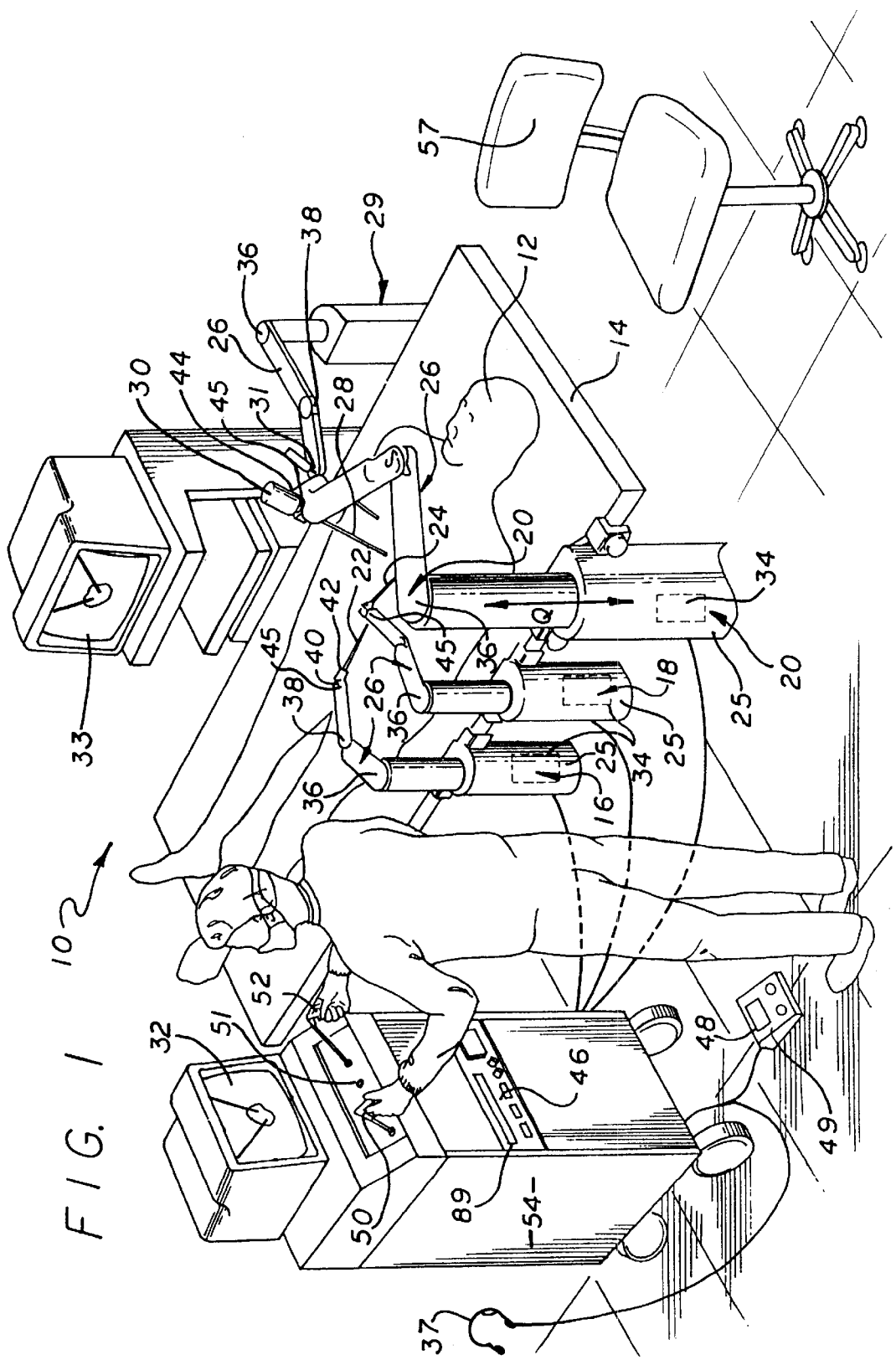
FIG. 1 is a perspective view of a minimally invasive surgical system in accordance with the present invention.

Referring to the drawings more particularly by reference numbers, FIG. 1 shows a system 10 that can be used to perform minimally invasive surgery. In a preferred embodiment, the system 10 may be used to perform a minimally invasive coronary artery bypass graft, or Endoscopic coronary artery bypass graft (E-CABG) and other anastomostic procedures. Although a MI-CABG procedure is shown and described, it is to be understood that the system may be used for other surgical procedures. For example, the system can be used to suture any pair of vessels as well as cauterizing, cutting, and radiating structures within a patient.

The system 10 is used to perform a procedure on a patient 12 that is typically lying on an operating table 14. Mounted to the operating table 14 is a first articulate arm 16, a second articulate arm 18 and a third articulate arm 20. The articulate arms 16–20 are preferably mounted to the table so that the arms are in a plane proximate the patient. It is to be appreciated that the arms may be mounted to a cart or some other device that places the arms proximate the plane of the patient as well. Although three articulate arms are shown and described, it is to be understood that the system may have any number of arms, such as one or more arms.

The first and second articulate arms 16 and 18 each have a base housing 25 and a robotic arm assembly 26 extending from the base housing 25. Surgical instruments 22 and 24 are preferably removably coupled at the end of each robotic arm assembly 26 of the first and second articulate arms 16, 18. Each of the instruments 22, 24 may be coupled to a corresponding robotic arm assembly 26 in a variety of fashions which will be discussed in further detail hereinbelow.

The third articulate arm 20 additionally comprises a base housing 25 and a robotic arm assembly 26, and preferably has an endoscope 28 that is attached to the robotic arm assembly 26. The base housing 25 and robotic arm assemblies 26 of each of the articulate arms 16, 18, and 20 are substantially similar. However, it is to be appreciated that the configuration of the third articulate arm 20, may be different as the purpose of the third articulate arm is to hold and position the endoscope 28 as opposed to hold and position a surgical instrument. Additionally, a fourth arm 29 may be included in the system 10. The fourth arm 29 may hold an additional instrument 31 for purposes set out hereinbelow.

The instruments 22, 24 and 29 and endoscope 28 are inserted through incisions cut into the skin of the patient 12. The endoscope 28 has a camera 30 that is coupled to a monitor 32 which displays images of the internal organs of the patient 12.

Each robotic arm assembly 26 has a base motor 34 which moves the arm assembly 26 in a linear fashion, relative to the base housing 25, as indicated by arrows Q. Each robotic arm assembly 26 also includes a first rotary motor 36 and a second rotary motor 38. Each of the robotic arm assemblies 26 also have a pair of passive joints 40 and 42. The passive joints 40, 42 are preferably disposed orthogonal to each other to provide pivotal movement of the instrument 22, 24 or endoscope 28 that is attached to a corresponding robotic arm assembly 26. The passive joints may be spring biased in any specific direction, however, they are not actively motor driven. The joint angle is controlled to a particular value using a feedback control loop. The robotic arm assemblies 26 also have a coupling mechanism 45 to couple the instruments 22 and 24, or endoscope 28 thereto. Additionally, each of the robotic arm assemblies 26 has a motor driven worm gear 44 to rotate the instrument 22, 24 or endoscope 28 attached thereto about its longitudinal axis. More particularly, the motor driven worm gear spins the instruments or endoscope.

The first, second, and third articulate arms 16, 18, 20 as well as the fourth arm 29 are coupled to a controller 46 which can control the movement of the arms. The arms are coupled to the controller 46 via wiring, cabling, or via a transmitter/receiver system such that control signals may be passed form the controller 46 to each of the articulate arms 16, 18, and 20. It is preferable, to ensure error free communication between each of the articulate arms 16, 18, 20 and 29 and the controller 46 that each arm 16, 18, 20 and 29 be electrically connected to the controller, and for the purposes of example, each arm 16, 18, 20 and 29 is electrically connected to the controller 46 via electrical cabling 47. However, it is possible to control each of the arms 16, 18, 20 and 29 remotely utilizing well-known remote control systems as opposed to direct electrical connections. As such remote control systems are well-known in the art, they will not be further discussed herein.

The controller 46 is connected to an input device 48 such as a foot pedal, hand controller, or voice recognition unit. For purposes of example, a foot controller and voice recognition unit are disclosed herein. The input device 48 can be operated by a surgeon to move the location of the endoscope 28 and view a different portion of the patient by depressing a corresponding button(s) disposed on the input device 48. Alternatively, the endoscope 28 may be positioned via voice control. Essentially, a vocabulary of instructions to move the endoscope, such as up, down, back, and in may be recognized via a speech recognition system and the appropriate instructions are sent to the controller. The speech recognition system may be any well-known speech recognition software. Additionally, the controller 46 includes a vocabulary of appropriate words that may be used with the system 10. Including such a vocabulary in the controller 46 may be accomplished through the inclusion of the aforementioned speech recognition software. To effectuate the voice recognition a microphone 37 is included in the system 10. The microphone 37 may be part of a digital system such that integrity of the signal is ensure.

The controller 46 receives the input signals from the input device 48 and moves the endoscope 28 and robotic arm assembly 26 of the third articulate arm 20 in accordance with the input commands of the surgeon. Each of the robotic arm assemblies 26 may be devices that are sold by the assignee of the present invention, Computer Motion, Inc. of Goleta, Calif., under the trademark AESOP. The system is also described in U.S. Pat. No. 5,515,478, which is hereby incorporated by reference. Although a foot pedal 49 is shown and described, it is to be understood that the system may have other input means such as a hand controller, or a speech recognition interface.

The movement and positioning of instruments 22, 24 attached to the first and second articulate arms 16 and 18 is controlled by a surgeon at a pair of master handles 50 and 52. Each of the master handles 50, 52 which can be manipulated by the surgeon, has a master-slave relationship with a corresponding one of the articulate arms 16, 18 so that movement of a handle 50 or 52 produces a corresponding movement of the surgical instrument 22, 24 attached to the articulate arm 16, 18. Additionally, a switch 51 may be included in the system 10. The switch 51 may be used by the surgeon to allow positioning of the fourth arm 29. This is accomplished because the position of the switch 51 allows the surgeon to select which of the arms a specific handle 50 or 52 controls. In this way, a pair of handles 50 and 52 may be used to control a plurality of robotic arms. The switch 51 may be connected to a multiplexer to act as a selector so that output from the multiplexer is transmitted to the appropriate robotic arm. Alternatively, the switch may have several positions and may, therefore, direct its output to the appropriate input on the controller 46.

The handles 50 and 52 may be mounted to a portable cabinet 54. A second television monitor 56 may be placed onto the cabinet 54 and coupled to the endoscope 28 via well-known means so that the surgeon can readily view the internal organs of the patient 12. The handles 50 and 52 are also coupled to the controller 46. The controller 46 receives input signals from the handles 50 and 52, computes a corresponding movement of the surgical instruments, and provides output signals to move the robotic arm assemblies 26 and instruments 22, 24. Because the surgeon may control the movement and orientation of the instruments 22, 24 without actually holding the ends of the instruments, the surgeon may use the system 10 of the present invention both seated or standing. One advantage of the present system is that a surgeon may perform endoscopic surgeries in a sitting position. This helps reduce surgeon fatigue and may improve performance and outcomes in the operating room, especially during those procedures that are many hours in length. To accommodate a seated position, a chair 57 may be provided with the system.

Alternatively, and as depicted in FIGS. 35–37, the handles 50 and 52 may be mounted to a handle stand 900. The handle stand 900 essentially provides for adjustment of the height and tilt of the handles 50 and 52. The handle stand 900 includes a base 902, a neck 904 and a handle portion 906. The base 902 may be adjusted so that the handle stand 900 is tilted. A lever 908 connected to an elongated rod 910 may provide a means for tilting the handle stand 900. As such, the stand 900 may be tilted such that a surgeon using the system 10 can remain comfortable standing or sitting while manipulating the handles 50 and 52.

Additionally, the handle stand 900 may be heightened or shortened depending upon the position of the surgeon (i.e. standing or sitting). This is accomplished via a telescoping section 912. The telescoping section 912 includes an upper portion 914 telescopingly housed within a lower portion 916. A spring biased detent 918 is attached to the upper portion 914 and a plurality of apertures 920 are provided in the lower portion 916 such that the detent 918 seats in an associated aperture 920. The upper portion 914 may be extended by depressing the detent 918 and pulling up on the stand 900. Alternatively, the stand 900 may be lowered by depressing the detent and pushing down on the stand 900. The telescoping section 912 and associated mechanisms serve as a means to raise and lower the stand 900.

Additionally, and as depicted in FIGS. 35–37, the handles 50 and 52 may be attached to the stand 900 via a plurality of rollers 930 and an elongated rod 932. Motion of the rod 932 is transmitted to a plurality of gears 934 disposed on the stand 900. The gears 934 may be housed within a housing 936 to protect them from the environment and to preclude access thereto. Additionally, potentiometers 938 are utilized to measure the position of the handles 50 and 52 relative to a starting position. This will be discussed in more detail hereinbelow. It is to be appreciated that the present invention may be accomplished either utilizing a cabinet 54 or a stand 900. As the handles 50 and 52 are connected to the controller 46 in either case.

Figure 2:
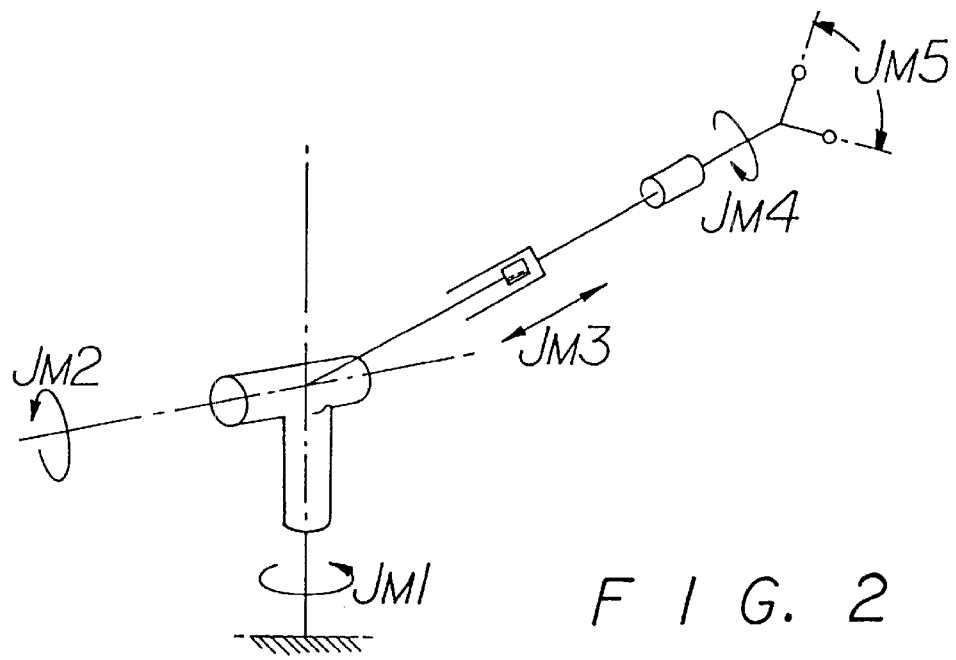
FIG. 2 is a schematic of a master of the system.

Each handle has multiple degrees of freedom provided by the various joints Jm1–Jm5 depicted in FIG. 2. Joints Jm1 and Jm2 allow the handle to rotate about a pivot point in the cabinet 54 or on the stand 900. Joint Jm3 allows the surgeon to move the handle into and out of the cabinet 54 in a linear manner or in a similar manner on the stand 900. Joint Jm4 allows the surgeon to rotate the master handle about a longitudinal axis of the handle. The joint Jm5 allows a surgeon to open and close a gripper.

Each joint Jm1–Jm5 has one or more position sensors which provides feedback signals that correspond to the relative position of the handle. The position sensors may be potentiometers, or any other feedback device such as rotary optical encoders that provides an electrical signal which corresponds to a change of position. Additionally, a plurality of position sensors may be emplaced at each joint to provide redundancy in the system which can be used to alert a surgeon of malfunctions or improper positioning of a corresponding robotic arm assembly 26.

In addition to position sensors, each joint may include tachometers, accelerometers, and force sensing load cells, each of which may provide electrical signals relating to velocity, acceleration and force being applied at a respective joint. Additionally, actuators may be included at each joint to reflect force feed back received at a robotic arm assembly 26. This may be especially helpful at joint jm5 to indicate the force encountered inside a patient by the gripper disposed at the end of one of the tools 22, or 24. As such, a force reflective element must be included at the gripper of the instrument 22, 24 to effectuate such a force reflective feedback loop. Force reflective elements, such as a piezoelectric element in combination with a whetstone bridge are well-known in the art. However, it is not heretofore know to utilize such force reflection with such a system 10.

As such, a force reflective element must be included at the gripper of the instrument 22, 24 to effectuate such a force reflective feedback loop. Force reflective elements, such as a piezoelectric element in combination with a whetstone bridge are well-known in the art. However, it is not heretofore know to utilize such force reflection with such a system 10. Additionally, and as depicted in FIG. 11, a specialized tool 300 may be used in conjunction with the system 10. The tool 300 is attached to an articulate arm 26 as any other instrument used with the system. However, the instrument 300 includes force reflective elements at its tip or distal end 302. As such, the instrument may be dragged across an artery, vein or the like and provide feedback to the surgeon as to the rigidity of the vessel. A lead 303 extends the length of the instrument and connects to the controller 46 to provide electrical signals indicative of the force encountered at the instrument tip. Such signals are then processed at the controller and transmitted to the corresponding handle which provides feedback indicative of the force. Force reflection and feedback are well known in the robotics art and as such will not be further discussed herein. In this fashion, the surgeon may determine whether there is plaque built up interior the vessel proximate the area that is palpated with the device. The force sensing portion 304 is electrically connected to a corresponding handle 51, 52 through the controller 46 and the switches disclosed herein earlier.

Figure 3:
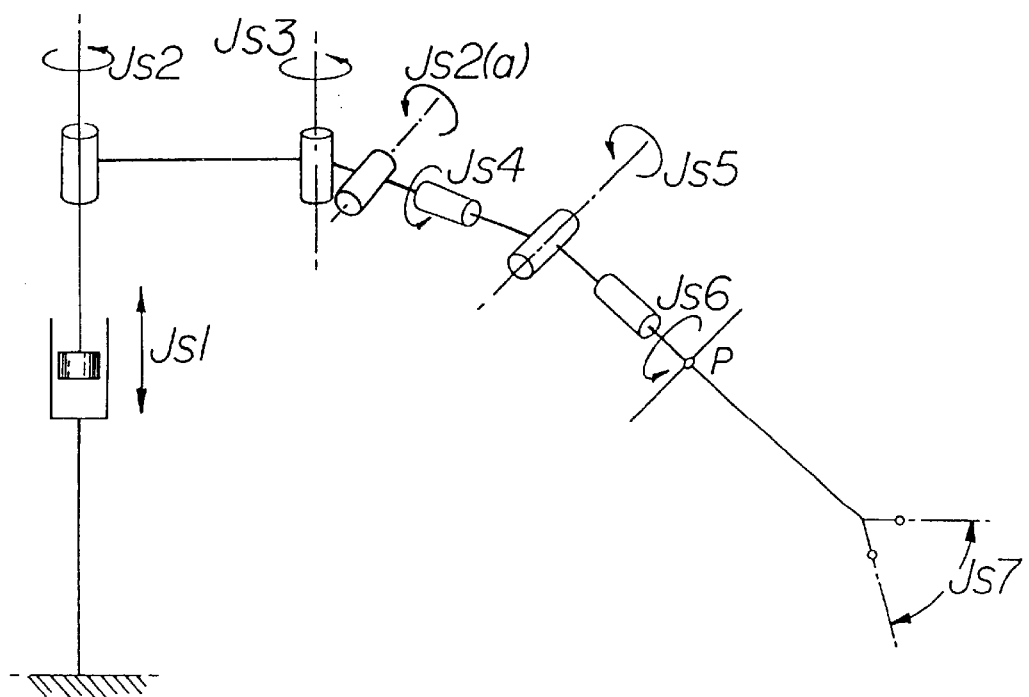
FIG. 3 is a schematic of a slave of the system.

FIG. 3 shows the various degrees of freedom of each articulate arm 16 and 18. The joints Js1, Js2 and Js3 correspond to the axes of movement of the base motor 34 and rotary motors 36, 38 of the robotic arm assemblies 26, respectively. The joints Js4 and Js5 correspond to the passive joints 40 and 42 of the arms 26. The joint Js6 may be a motor which rotates the surgical instruments about the longitudinal axis of the instrument. The joint Js7 may be a pair of fingers that can open and close. The instruments 22 and 24 move about a pivot point P located at the incision of the patient.

Joint Js2(s) is a joint that is included directly after Joints Js2 and Js3 to provide for additional positionability of the arm 26, and more particularly an instruments disposed at the end thereof.

Joint Js2(a) is disposed orthogonal to both joints Js2 and Js3. Essentially, joint Js2(a) allows the arm 26 to be offset an angle, theta, from the plane formed by segments 36 and 38. As such, the controller must account for this offset which is measured by a potentiometer or optical encoder emplaced at the joint Js2(a) and is depicted in FIG. 12.

FIG. 12 shows a robotic arm including the additional joint, Js2(a). This joint is not motor drive, however the displacement of this joint from the plane formed by segments 36 and 38 must be accounted for to ensure proper functioning of the robotic arm. As such, and as disclosed hereinbelow, the coordinate transforms necessary to provide for movement of surgical instruments disposed at the end of the arm 26 must include transformation at this joint. Coordinate frame transforms are well known in the robotic art and as such, they will not be further discussed herein. It is the inclusion of the additional joint itself that is unobvious over the prior art. More particularly, the inclusion of the additional joint provides additional maneuverability of the robotic arm making it easier to position for use with a patient.

The joints Js4 and Js5 correspond to the passive joints 40 and 42 of the arms 26. The joint Js6 may be a motor which rotates the surgical instruments about the longitudinal axis of the instrument. The joint Js7 may be a pair of fingers that can open and close. The instruments 22 and 24 move about a pivot point P located at the incision of the patient.

Figure 4:
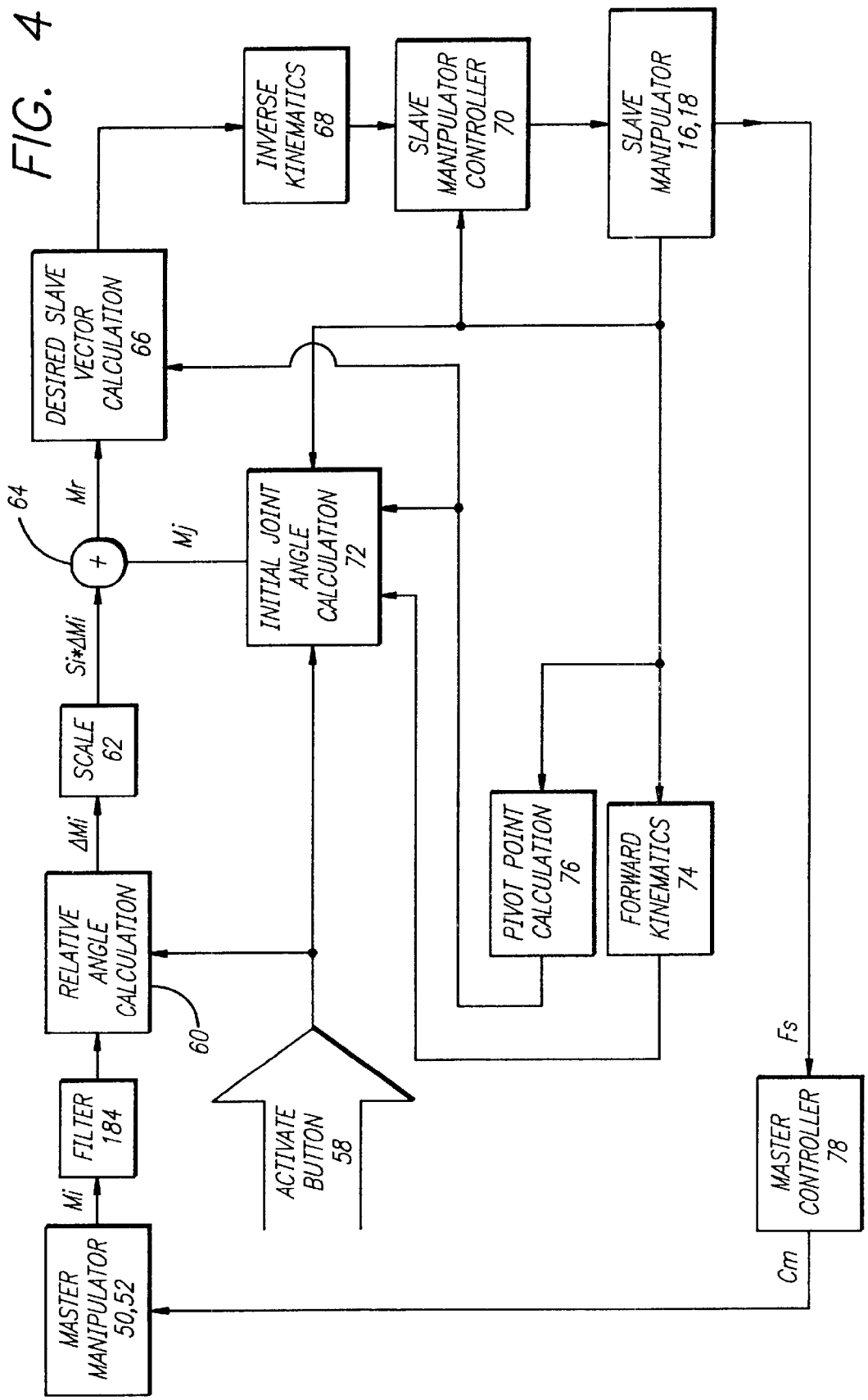
FIG. 4 is a schematic of a control system of the system.

FIG. 4 shows a schematic of a control system that translates a movement of a master handle into a corresponding movement of a surgical instrument. In accordance with the control system shown in FIG. 4, the controller 46 computes output signals for the articulate arms so that the surgical instrument moves in conjunction with the movement of the handle. Each handle may have an input button 58 which enables the instrument to move with the handle. When the input button 58 is depressed the surgical instrument follows the movement of the handle. When the button 58 is released the instrument does not track the movement of the handle. In this manner the surgeon can adjust or "ratchet" the position of the handle without creating a corresponding undesirable movement of the instrument. The "ratchet" feature allows the surgeon to continuously move the handles to more desirable positions without altering the positions of the arms. Additionally, because the handles are constrained by a pivot point the ratchet feature allows the surgeon to move the instruments beyond the dimensional limitations of the handles. Although an input button 58 is shown and described, it is to be understood that the surgical instrument may be activated by other means such as voice recognition. Using the voice recognition would require a specifically vocabulary such as "AWAKE" and "SLEEP" or some other two words having opposing meanings. Voice recognition is well known in general, and it is the specific use of voice recognition in this system 10 that has substantial novelty and utility.

The input button may alternatively be latched so that movement of the corresponding instrument toggles between active and inactive each time the button is depressed by the surgeon.

When the surgeon moves a handle, the position sensors provide feedback signals M–M5 that correspond to the movement of the joints Jm1–Jm5, respectively. The controller 46 computes the difference between the new handle position and the original handle position in computation block 60 to generate incremental position values _M1–_M5.

The incremental position values _M1–_M5 are multiplied by scale factors S1–S5, respectively in block 62. The scale factors are typically set at less than one so that the movement of the instrument is less than the movement of the handle. In this manner the surgeon can produce very fine movements of the instruments with relatively coarse movements of the handles. The scale factors S1–S5 are variable so that the surgeon can vary the resolution of instrument movement. Each scale factor is preferably individually variable so that the surgeon can more finely control the instrument in certain directions. By way of example, by setting one of the scale factors at zero the surgeon can prevent the instrument from moving in one direction. This may be advantageous if the surgeon does not want the surgical instrument to contact an organ or certain tissue located in a certain direction relative to the patient. Although scale factors smaller than a unit one are described, it is to be understood that a scale factor may be greater than one. For example, it may be desirable to spin the instrument at a greater rate than a corresponding spin of the handle.

The controller 46 adds the incremental values _M1–_M5 to the initial joint angles Mj1–Mj5 in adder element 64 to provide values Mr1–Mr5. The controller 46 then computes desired slave vector calculations in computation block 66 in accordance with the following equations.

$$Rdx = Mr3 \cdot \sin(Mr2) \cdot \cos(Mr1) + Px$$

$$Rdy = Mr3 \cdot \sin(Mr2) \cdot \sin(Mr1) + Py$$

$$Rdz = Mr3 \cdot \cos(Mr2) + Pz$$

$$Sdr = Mr4$$

$$Sdg = Mr5$$

where;
  Rdx,y,z=the new desired position of the end effector of the instrument.
  Sdr=the angular rotation of the instrument about the instrument longitudinal axis.
  Sdg=the amount of movement of the instrument fingers.
  Px,y,z=the position of the pivot point P.

The controller 46 then computes the movement of the robotic arm 26 in computational block 68 in accordance with the following equations.

$$Jsd1 = Rdz$$

$$Jsd3 = \pi - \cos^{-1}\left[\frac{Rdx^2 + Rdy^2 - L1^2 - L2^2}{2L1 \cdot L2}\right]$$

$$Jsd2 = \tan^{-1}(Rdy/Rdx) + \Delta \text{ for } Jsd3 \leq 0$$

$$Jsd2 = \tan^{-1}(Rdy/Rdx) - \Delta \text{ for } Jsd3 > 0$$

$$\Delta = \cos^{-1}\left[\frac{Rdx^2 + Rdy^2 + L1^2 - L2^2}{2 \cdot L1\sqrt{Rdx^2 + Rdy^2}}\right]$$

$$Jsd6 = Mr4$$

$$Jsd7 = Mr5$$

where;
- Jsd1=the movement of the linear motor.
- Jsd2=the movement of the first rotary motor.
- Jsd3=the movement of the second rotary motor.
- Jsd6=the movement of the rotational motor.
- Jsd7=the movement of the gripper.
- L1=the length of the linkage arm between the first rotary motor and the second rotary motor.
- L2=the length of the linkage arm between the second rotary motor and the passive joints.

The controller provides output signals to the motors to move the arm and instrument in the desired location in block 70. This process is repeated for each movement of the handle.

The master handle will have a different spatial position relative to the surgical instrument if the surgeon releases, or toggles, the input button and moves the handle.

When the input button 58 is initially depressed, the controller 46 computes initial joint angles Mj1–Mj5 in computational block 72 with the following equations.

$$Mj1 = \tan^{-1}(ty/tx)$$

$$Mj2 = \tan^{-1}(d/tz)$$

$$Mj3 = D$$

$$Mj4 = Js6$$

$$Mj5 = Js7$$

$$d = \sqrt{tx^2 + ty^2}$$

$$tx = \frac{Rsx - Px}{D} \quad ty = \frac{Rsy - Py}{D} \quad tz = \frac{Rsz - Pz}{D}$$

$$D = \sqrt{(Rsx - Px)^2 + (Rsy - Py)^2 + (Rsz - Pz)^2}$$

The forward kinematic values are computed in block 74 with the following equations.

$$Rsx = L1 \cdot \cos(Js2) + L2 \cdot \cos(Js2 + Js3)$$

$$Rsy = L1 \cdot \sin(Js2) + L2 \cdot \sin(Js2 + Js3)$$

$$Rsz = J1$$

Figure 5:
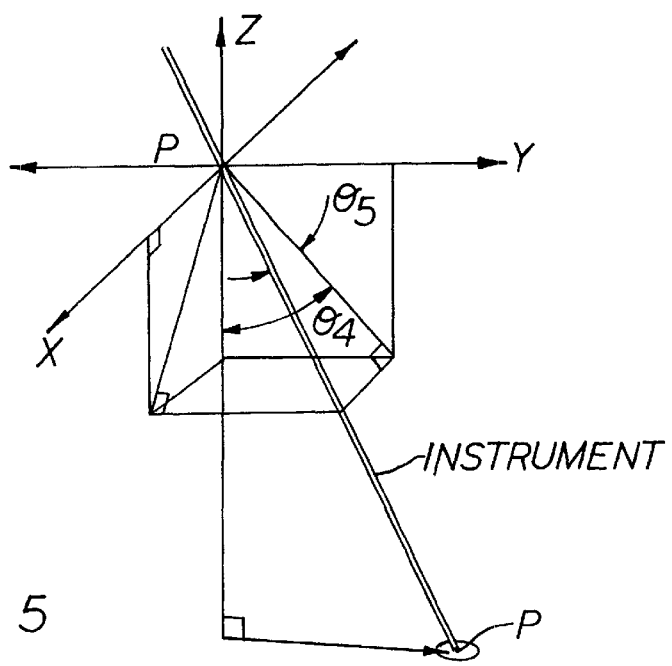
FIG. 5 is a schematic showing the instrument within a coordinate frame.

The joint angles Mj are provided to adder 64. The pivot points Px, Py and Pz are computed in computational block 76 as follows. The pivot point is calculated by initially determining the original position of the intersection of the end effector and the instrument PO, and the unit vector Uo which has the same orientation as the instrument. The position P(x, y, z) values can be derived from various position sensors of the robotic arm. Referring to FIG. 5 the instrument is within a first coordinate frame (x, y, z) which has the angles q4 and q5. The unit vector Uo is computed by the transformation matrix:

$$Uo = \begin{bmatrix} \cos\Theta_5 & 0 & -\sin\Theta_5 \\ -\sin\Theta_4\sin\Theta_5 & \cos\Theta_4 & -\sin\Theta_4\cos\Theta_5 \\ \cos\Theta_4\sin\Theta_5 & \sin\Theta_4 & \cos\Theta_4 \end{bmatrix} \begin{bmatrix} 0 \\ 0 \\ -1 \end{bmatrix}$$

After each movement of the end effector an angular movement of the instrument DQ is computed by taking the arcsin of the cross-product of the first and second unit vectors Uo and U1 of the instrument in accordance with the following line equations Lo and L1.

$$\Delta\theta = \arcsin(|T|)$$

$$T = Uo \infty U1$$

where;
T=a vector which is a cross-product of unit vectors Uo and U1.

Figure 6:
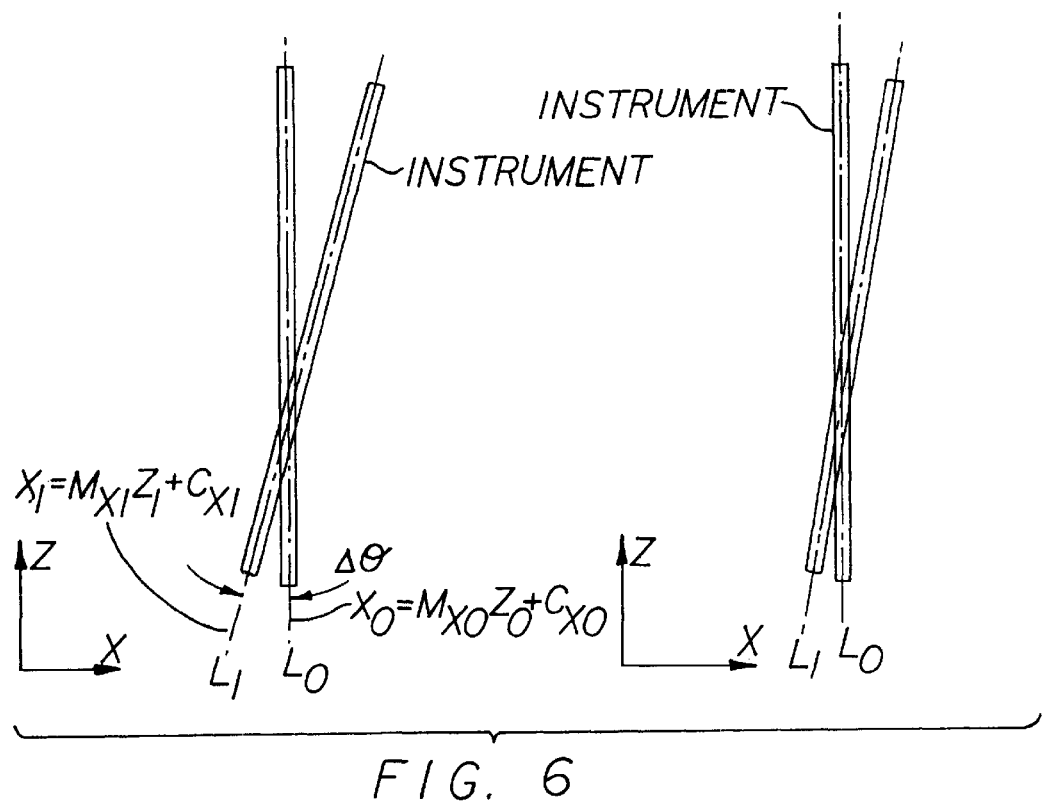
FIG. 6 is a schematic of the instrument moving about a pivot point.

The unit vector of the new instrument position U1 is again determined using the position sensors and the transformation matrix described above. If the angle $\Delta\theta$ is greater than a threshold value, then a new pivot point is calculated and Uo is set to U1. As shown in FIG. 6, the first and second instrument orientations can be defined by the line equations Lo and L1:

Lo:

$$xo = M_x0 \cdot Zo + Cxo$$

$$yo = M_yo \cdot Zo + Cyo$$

L1:

$$x1 = Mx1 \cdot Z1 + Cx1$$

$$y1 = My1 \cdot Z1 + Cy1$$

where;
- Zo=a Z coordinate along the line Lo relative to the z axis of the first coordinate system.
- Z1=a Z coordinate along the line L1 relative to the z axis of the first coordinate system.
- Mxo=a slope of the line Lo as a function of Zo.
- Myo=a slope of the line Lo as a function of Zo.
- Mx1=a slope of the line L1 as a function of Z1.
- My1=a slope of the line L1 as a function of Z1.
- Cxo=a constant which represents the intersection of the line Lo and the x axis of the first coordinate system.
- Cyo=a constant which represents the intersection of the line Lo and the y axis of the first coordinate system.
- Cx1=a constant which represents the intersection of the L1 and the x axis of the first coordinate system.
- Cy1=a constant which represents the intersection of the line L1 and the y axis of the first coordinate system.

The slopes are computed using the following algorithms:

Mxo=Uxo/Uzo

Myo=Uyo/Uzo

Mx1=Ux1/Uz1

$My1 = Uy1/Uz1$ $Cx0 = Pox - Mx1 \cdot Poz$ $Cy0 = Poy - My1 \cdot Poz$ $Cx1 = P1x - Mx1 \cdot P1z$ $Cy1 = P1y - My1 \cdot P1z$ where;

Uo(x, y and z)=the unit vectors of the instrument in the first position within the first coordinate system.

U1(x, y and z)=the unit vectors of the instrument in the second position within the first coordinate system. Po(x, y and z)=the coordinates of the intersection of the end effector and the instrument in the first position within the first coordinate system.

P1(x, y and z)=the coordinates of the intersection of the end effector and the instrument in the second position within the first coordinate system.

To find an approximate pivot point location, the pivot points of the instrument in the first orientation Lo (pivot point Ro) and in the second orientation L1 (pivot point R1) are determined, and the distance half way between the two points Ro and R1 is computed and stored as the pivot point $R_{ave}$ of the instrument. The pivot point $R_{ave}$ is determined by using the cross-product vector T.

To find the points Ro and R1 the following equalities are set to define a line with the same orientation as the vector T that passes through both Lo and L1.

$tx = Tx/Tz$ $ty = Ty/Tz$ where;

tx=the slope of a line defined by vector T relative to the Z-x plane of the first coordinate system.

ty=the slope of a line defined by vector T relative to the Z-y plane of the first coordinate system.

Tx=the x component of the vector T.

Ty=the y component of the vector T.

Tz=the z component of the vector T.

Picking two points to determine the slopes Tx, Ty and Tz (eg. Tx=x1−xo, Ty=y1−yo and Tz=z1−z0) and substituting the line equations Lo and LI, provides a solution for the point coordinates for Ro (xo, yo, zo) and R1 (x1, y1, z1) as follows.

$$zo = ((Mx1-tx)z1 + Cx1 - Cxo)/(Mxo-tx)$$

$$z1 = ((Cy1-Cyo)(Mxo-tx) - (Cx1-Cxo)(Myo-ty))/((Myo-ty)(Mx1-tx) - (My1-ty)(Mxo-tx))$$

$$yo = Myo \geq zo + Cyo$$

$$y1 = My1 \geq z1 + Cy1$$

$$xo = Mxo \geq zo + Cxo$$

$$x1 = Mx1 \geq z1 + Cx1$$

The average distance between the pivot points Ro and R1 is computed with the following equation and stored as the pivot point of the instrument.

$$R_{ave} = ((x1+xo)/2, (y1+yo)/2, (z1+zo)/2)$$

The pivot point can be continually updated with the above described algorithm routine. Any movement of the pivot point can be compared to a threshold value and a warning signal can be issued or the robotic system can become disengaged if the pivot point moves beyond a set limit. The comparison with a set limit may be useful in determining whether the patient is being moved, or the instrument is being manipulated outside of the patient, situations which may result in injury to the patient or the occupants of the operating room.

While substantial real time movement of the robotic arms is provided, it may be appreciated that pre-planned movements may be incorporated into the present system 10. This is most advantageous with regard to movement of the endoscope. Any type of movement may be stored in am associated memory of the controller so that a surgeon may define his own favorite movements and then actuate such movement by pressing a button or via voice control. Because the movement is taught in the present application as well as those patents incorporated herein by reference, no further disclosure of this concept is required.

To provide feedback to the surgeon, the system 10 may include a voice feedback unit. As such, it the robotic arms suffer any malfunction, the voice feedback may supply a message that such error has occurred. Additionally, messages regarding instrument location, time-in-use, as well as a host of other data may be supplied to the surgeon through the voice feedback unit. If such a condition occurs that requires a message, the system has a set of messages stored in an associated memory, such message may be encoded and saved in the memory. A speech synthesis unit 89, as depicted in FIG. 1 can then vocalize the message to the surgeon. In this fashion, a surgeon can maintain sight of the operative environment as opposed to looking for messages displayed on a video screen or the like. Speech synthesis is well known, although its inclusion in a master-slave robotic system for minimally invasive surgery is heretofore unknown and present novel and unobvious advantages.

To provide feedback to the surgeon the fingers of the instruments may have pressure sensors that sense the reacting force provided by the object being grasped by the end effector. Referring to FIG. 4, the controller 46 receives the pressure sensor signals Fs and generates corresponding signals Cm in block 78 that are provided to an actuator located within the handle. The actuator provides a corresponding pressure on the handle which is transmitted to the surgeon's hand. The pressure feedback allows the surgeon to sense the pressure being applied by the instrument. As an alternate embodiment, the handle may be coupled to the end effector fingers by a mechanical cable that directly transfers the grasping force of the fingers to the hands of the surgeon.

Figure 7:
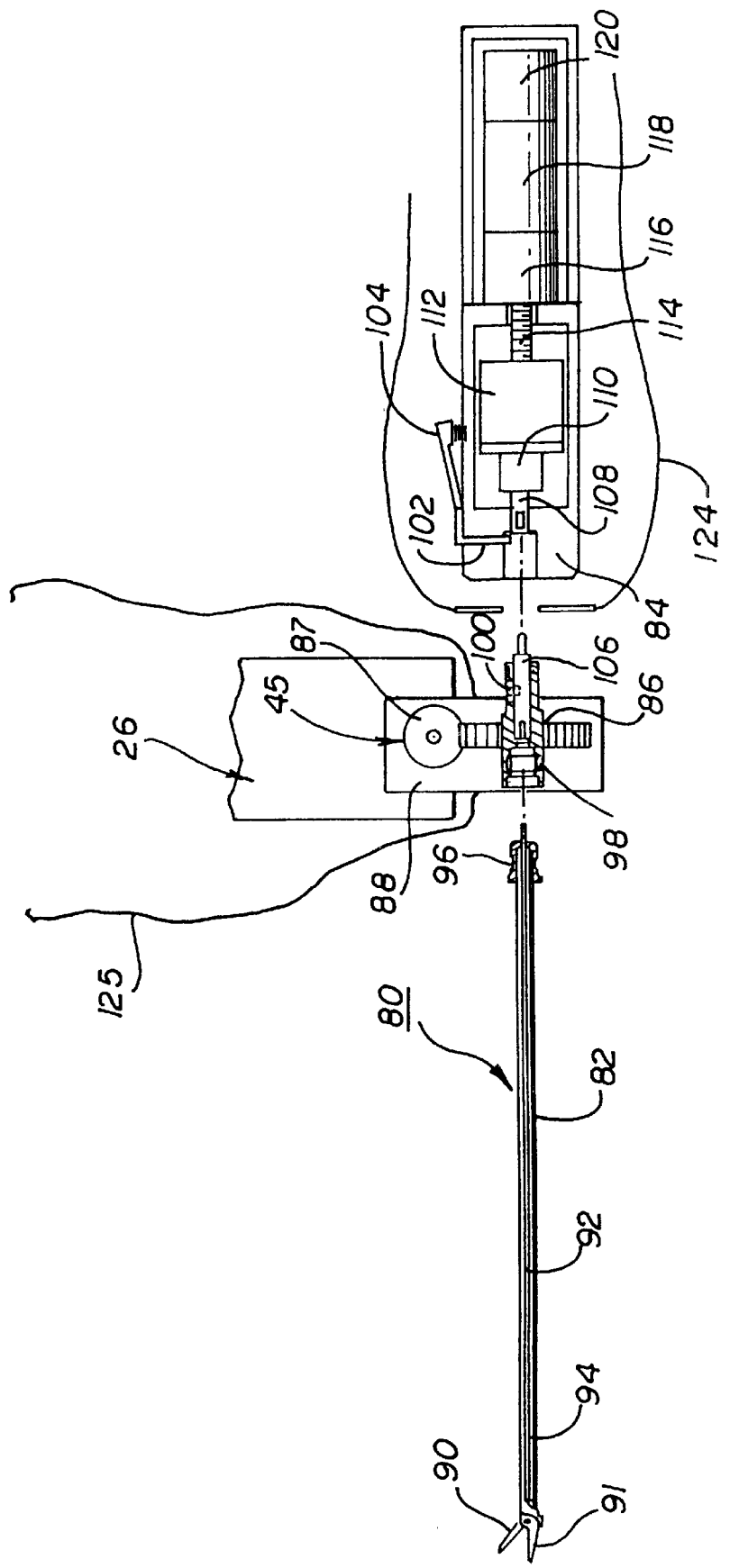
FIG. 7 is an exploded view of an end effector in accordance with the system of the present invention.

FIG. 7 shows a preferred embodiment of an end effector 80 that may be used in the present invention. The end effector 80 includes a surgical instrument 82, such as those disclosed hereinabove 22, 24, that is coupled to a front loading tool driver 84. The end effector 80 is mounted to one of the robotic arm assemblies 26 by coupling mechanism 45. The coupling mechanism 45 includes a collar 85 that removably attaches to a holder 86. The holder 86 includes a worm gear 87 that is driven by a motor in the robotic arm assembly 26 to rotate the collar 85 and in turn rotate the instrument 82 about its longitudinal axis. The holder 86 includes a shaft 88 that seats into a slot in the robotic arm assembly 26. The shaft 88 may be turned by the motor in the arm assembly, which then rotates the worm gear 87 thus rotating the collar 86 and the instrument 82. A tightening tool 89 may be employed to tighten and loosen the collar about the instrument 82. Such a tool operates like a chuck key, to tighten and loosen the collar 86.

The surgical instrument 82 has a first finger 90 that is pivotally connected to a second finger 91. The fingers 90, 91 can be manipulated to hold objects such as tissue or a suturing needle. The inner surface of the fingers may have a texture to increase the friction and grasping ability of the instrument 82. The first finger 90 is coupled to a rod 92 that extends through a center channel 94 of the instrument 82. The instrument 82 may have an outer sleeve 96 which cooperates with a spring biased ball quick disconnect fastener 98. The quick disconnect 98 allows instruments other than the finger grasper to be coupled to front loading tool driver 84. For example, the instrument 82 may be decoupled from the quick disconnect 98 and replaced by a cutting tool, a suturing tool, a stapling tool adapted for use in this system, such as the stapling apparatus disclosed in U.S. Pat. No. 5,499,990 or 5,389,103 assigned to Karlsruhe, a cutting blade, or other surgical tools used in minimally invasive surgery. The quick disconnect 98 allows the surgical instruments to be interchanged without having to re-sterilize the front loading tool driver 84 each time an instrument is plugged into the tool driver 84. The operation of the front loading tool driver 84 shall be discussed in further detail hereinbelow.

The quick disconnect 98 has a slot 100 that receives a pin 102 of the front loading tool driver 84. The pin 102 locks the quick disconnect 98 to the front loading tool driver 100. The pin 102 can be released by depressing a spring biased lever 104. The quick disconnect 98 has a piston 106 that is attached to the tool rod 92 and in abutment with an output piston 108 of a load cell 110 located within the front loading tool driver 84.

The load cell 110 is mounted to a lead screw nut 112. The lead screw nut 112 is coupled to a lead screw 114 that extends from a gear box 116. The gear box 116 is driven by a reversible motor 118 that is coupled to an encoder 120. The entire end effector 80 is rotated by the motor driven worm gear 87.

In operation, the motor 118 of the front loading tool driver 84 receives input commands from the controller 46 via electrical wiring, or a transmitter/receiver system and activates, accordingly. The motor 118 rotates the lead screw 114 which moves the lead screw nut 112 and load cell 110 in a linear manner. Movement of the load cell 110 drives the coupler piston 106 and tool rod 92, which rotate the first finger 88. The load cell 110 senses the counteractive force being applied to the fingers and provides a corresponding feedback signal to the controller 46.

Figure 13:
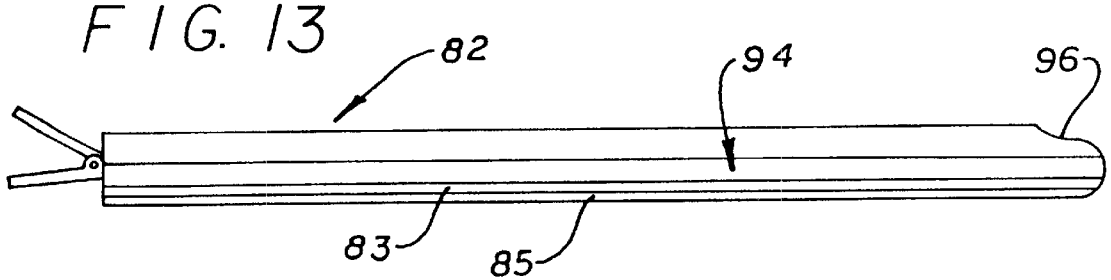
FIG. 13 is a side cross sectional view of an instrument in accordance with the present invention wherein said instrument includes irrigation and suction lines.
Figure 14:
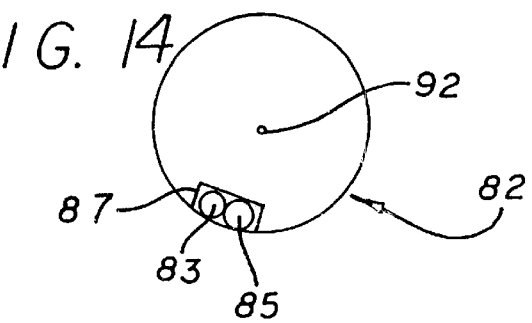
FIG. 14 is an end sectional view of the instrument of FIG. 13.
Figure 19:
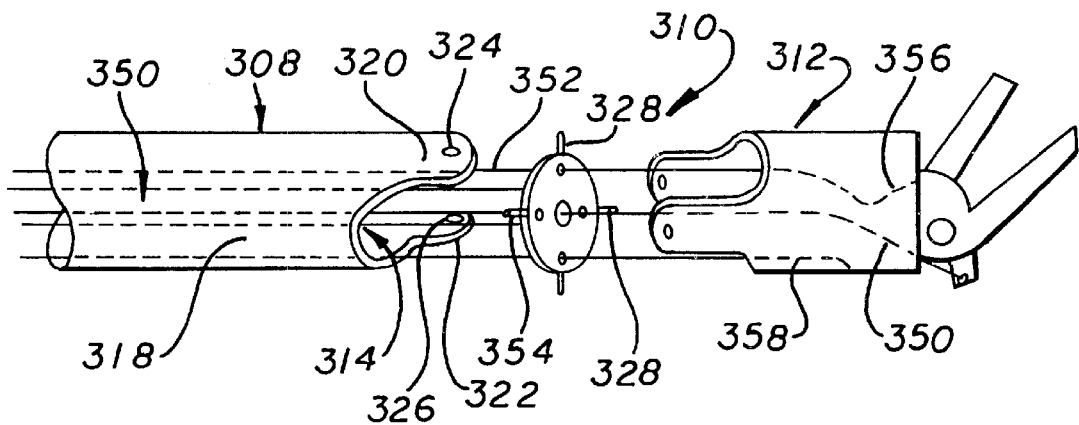
FIG. 19 is an exploded view of the articulable portion of the articulable instrument in accordance with the present invention.
Figure 20:
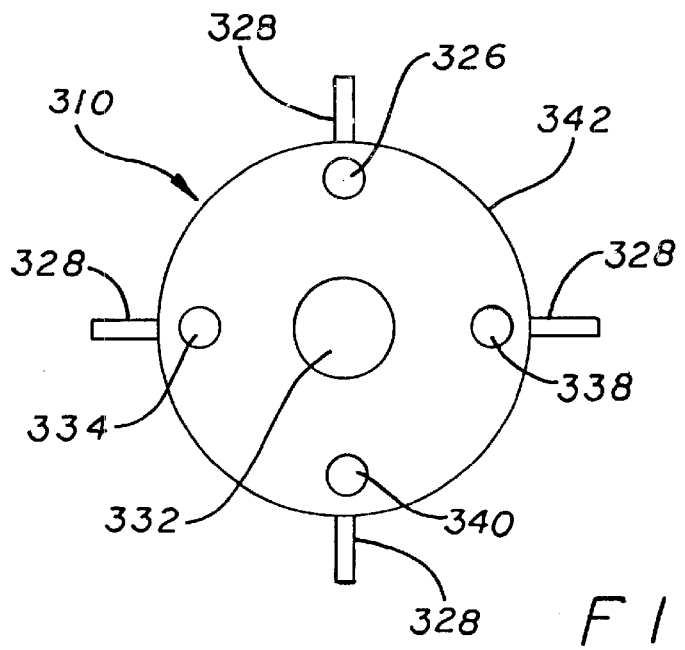
FIG. 20 is a plan view of a pivot linkage in accordance with the articulate portion of the articulable surgical instrument of the present invention.
Figure 21:
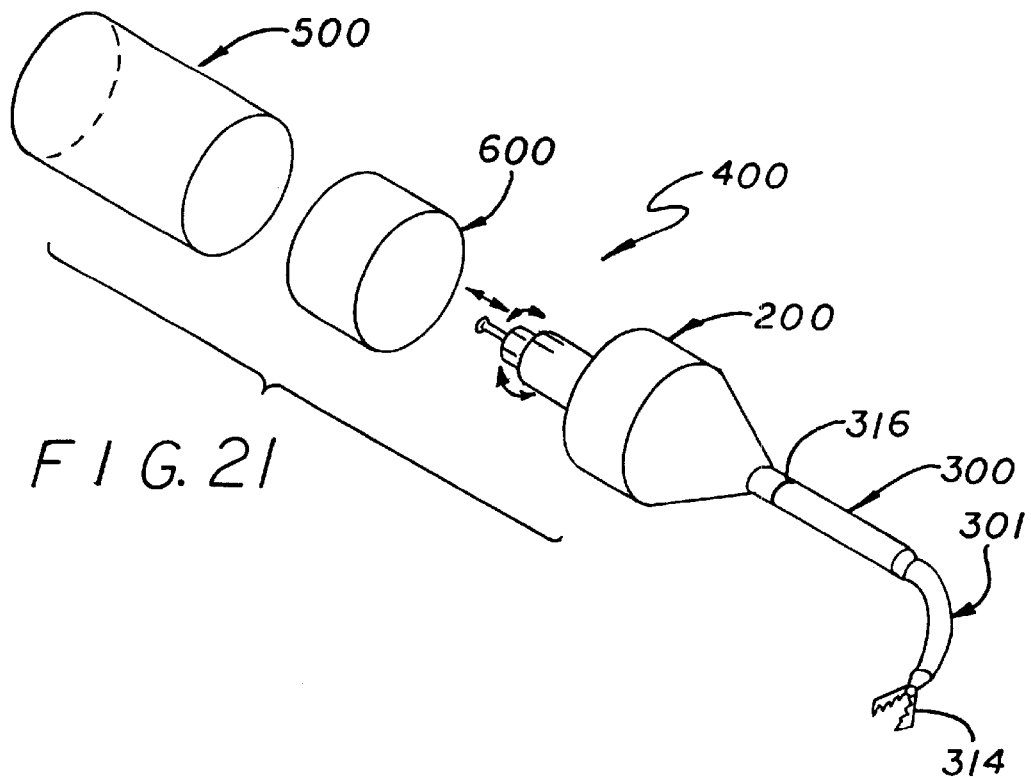
FIG. 21 is a perspective view of an articulating tool driving assembly in accordance with the present invention.

The tool 82 and any tool included in the system may include an irrigation line 83 and a suction line 85. Each of the irrigation line 83 and suction line 85 extend down the center channel 94 and may be enclosed within a separate housing 89 disposed interior the tool 82. This is depicted in FIGS. 13 and 14. The irrigation line 83 is connected to a water source or saline source and may be used to irrigate the surgical site or to remove tissue from the instrument 82. Irrigation systems are generally well known. It is not heretofore known, though, to include an irrigation line 83 into an endoscopic instrument for use with a robotic system 10.

Additionally, a suction line 85 may be enclosed within the housing 89 disposed interior the instrument 82. Suction is generally needed to remove blood, or other fluids from the surgical site. Again, it is not heretofore known to include a suction line 85 in an endoscopic instrument for use with a robotic system 10. As such, the inclusion of either an irrigation line or a suction line present advances in the art that are novel and as of yet unknown.

Each of the suction and irrigation lines run to well known suction and irrigation systems which are well known in the art. The activation of irrigation or suction is generally accomplished through the use of a foot controller or hand controller. However, it must be appreciated that the activation of such devices may be integrated into the present system by including a button at the surgeon input device or the cabinet. Alternatively, the suction and irrigation may be voice activated and as such, additional vocabulary must be included in the voice recognition system of the present invention. More particularly, the voice recognition system should recognize the commands "suction" and "irrigate".

The front loading tool driver 84 may be covered with a sterile drape 124 so that the tool driver 84 does not have to be sterilized after each surgical procedure. Additionally, the robotic arm assembly 26 is preferably covered with a sterile drape 125 so that it does not have to be sterilized either. The drapes 124, 125 serve substantially as a means for enclosing the front loading tool driver 84 and robotic arm assembly 26. The drape 125 used to enclose the robotic arm assembly 26 is depicted in further detail in FIG. 26. The drape 125 has a substantially open end 300 wherein the robotic arm assembly 26 may be emplaced into the drape 125. The drape 125 additionally includes a substantially tapered enclosed end 302 that effectively separates the arm assembly 26 from the operating room environment. A washer 304 having a small aperture 306 formed therethrough allows an instrument to be coupled to the arm assembly 26 via the coupling mechanism 45. The washer 304 reinforces the drape 125 to ensure that the drape 125 does not tear as the arm assembly 26 moves about. Essentially, the instrument cannot be enclosed in the drape 125 because it is to be inserted into the patient 12. The drape 125 also includes a plurality of tape 308 having adhesive 310 disposed thereon. At least one piece of tape 308 is opposedly arranged the other pieces of tape 308 to effectuate the closing of the drape 125 about the arm assembly 26.

Figure 8:
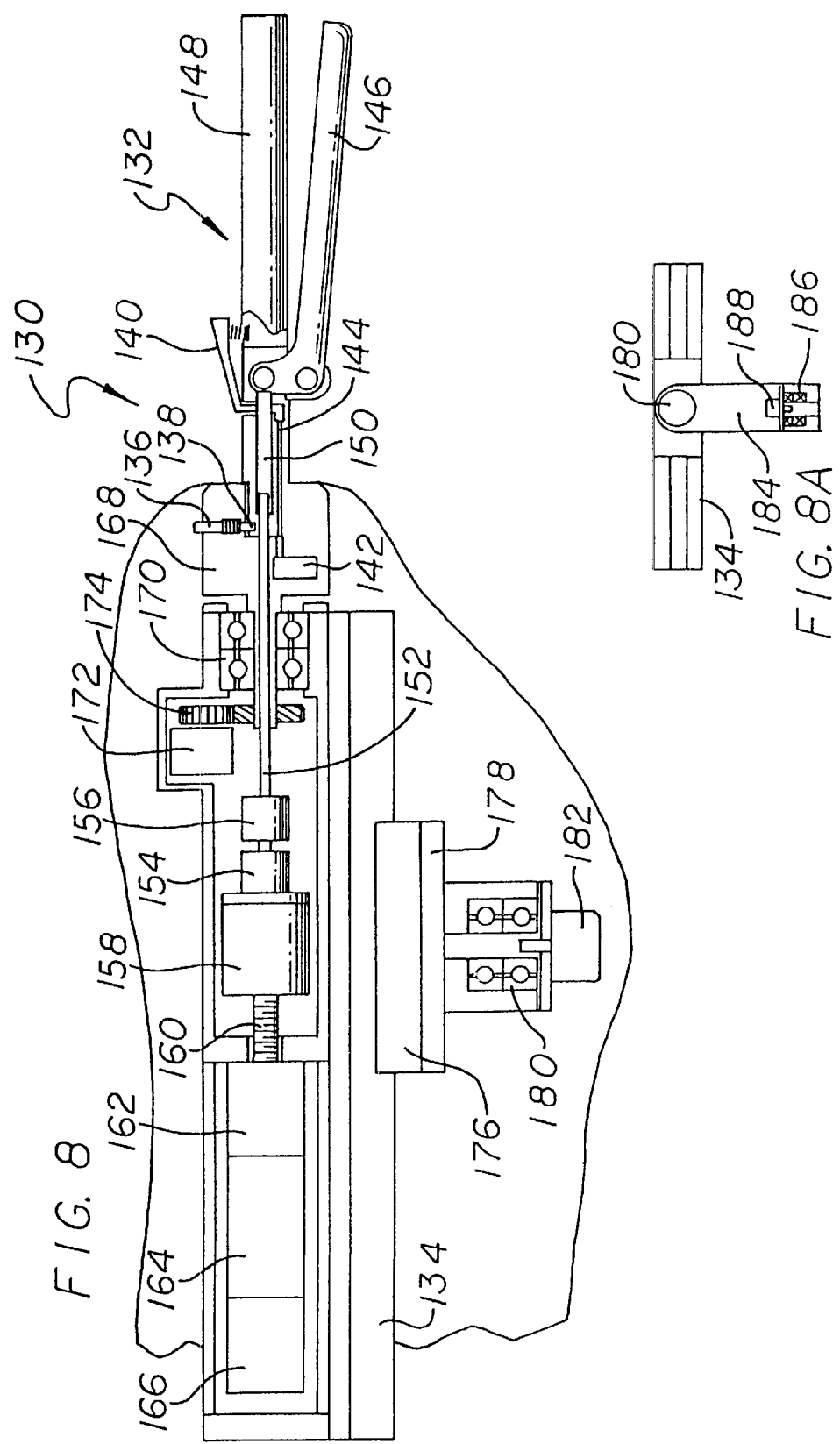
FIG. 8 is a side sectional view of a master handle of the system in accordance with the present invention.
Figure 9:
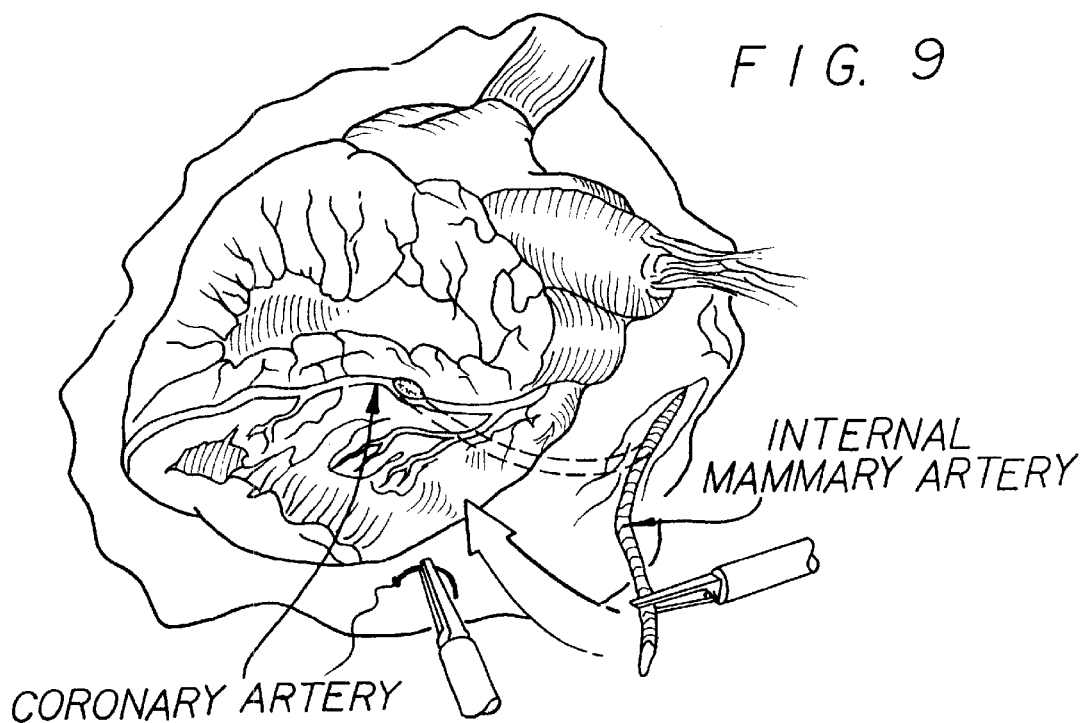
FIGS. 9–10A–I are illustrations showing an internal mammary artery being grafted to a coronary artery.

FIGS. 8 and 8a show a preferred embodiment of a master handle assembly 130. The master handle assembly 130 includes a master handle 132 that is coupled to an arm 134. The master handle 132 may be coupled to the arm 134 by a pin 136 that is inserted into a corresponding slot 138 in the handle 132. The handle 132 has a control button 140 that can be depressed by the surgeon. The control button 140 is coupled to a switch 142 by a shaft 144. The control button 140 corresponds to the input button 58 shown in FIG. 4, and activates the movement of the end effector.

The master handle 132 has a first gripper 146 that is pivotally connected to a second stationary gripper 148. Rotation of the first gripper 146 creates a corresponding linear movement of a handle shaft 150. The handle shaft 150 moves a gripper shaft 152 that is coupled a load cell 154 by a bearing 156. The load cell 154 senses the amount of pressure being applied thereto and provides an input signal to the controller 46. The controller 46 then provides an output signal to move the fingers of the end effector.

The load cell 154 is mounted to a lead screw nut 158 that is coupled to a lead screw 160. The lead screw 160 extends from a reduction box 162 that is coupled to a motor 164 which has an encoder 166. The controller 46 of the system receives the feedback signal of the load cell 110 in the end effector and provides a corresponding command signal to the motor to move the lead screw 160 and apply a pressure on the gripper so that the surgeon receives feedback relating to the force being applied by the end effector. In this manner the surgeon has a "feel" for operating the end effector.

The handle is attached to a swivel housing 168 that rotates about bearing 170. The swivel housing 168 is coupled to a position sensor 172 by a gear assembly 174. The position sensor 172 may be a potentiometer which provides feedback signals to the controller 46 that correspond to the relative position of the handle. Additionally, an optical encoder may be employed for this purpose. Alternatively, both a potentiometer and an optical encoder may be used to provide redundancy in the system. The swivel movement is translated to a corresponding spin of the end effector by the controller and robotic arm assembly. This same type of assembly is employed in the stand 900.

The arm 134 may be coupled to a linear bearing 176 and corresponding position sensor 178 which allow and sense linear movement of the handle. The linear movement of the handle is translated into a corresponding linear movement of the end effector by the controller and robotic arm assembly. The arm can pivot about bearings 180, and be sensed by position sensor 182 located in a stand 184. The stand 184 can rotate about bearing 186 which has a corresponding position sensor 188. The arm rotation is translated into corresponding pivot movement of the end effector by the controller and robotic arm assembly.

A human hand will have a natural tremor typically resonating between 6–12 hertz. To eliminate tracking movement of the surgical instruments with the hand tremor, the system may have a filter that filters out any movement of the handles that occurs within the tremor frequency bandwidth. Referring to FIG. 4, the filter 184 may filter analog signals provided by the potentiometers in a frequency range between 6–12 hertz. Alternatively, an optical encoder and digital filter may be used for this purpose.

As shown in FIGS. 9 and 10A–J, the system is preferably used to perform a cardiac procedure such as a coronary artery bypass graft (CABG). The procedure is performed by initially cutting three incisions in the patient and inserting the surgical instruments 22 and 24, and the endoscope 26 through the incisions. One of the surgical instruments 22 holds a suturing needle and accompanying thread when inserted into the chest cavity of the patient. If the artery is to be grafted with a secondary vessel, such as a saphenous vein, the other surgical instrument 24 may hold the vein while the end effector of the instrument is inserted into the patient.

Figure 10A:
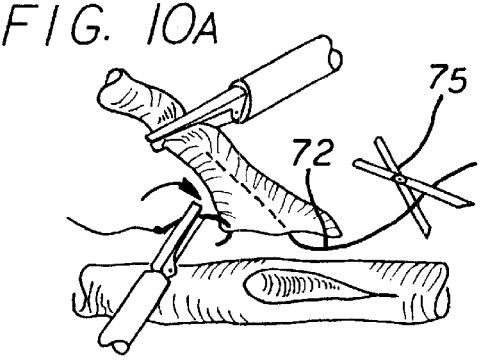
Figure 10B:
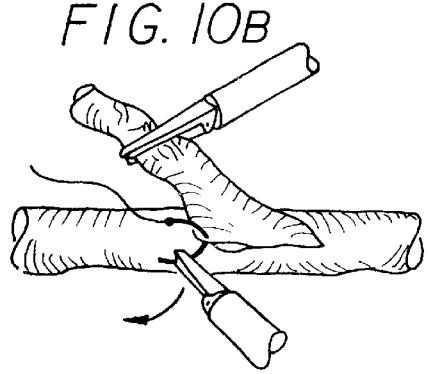
Figure 10C:
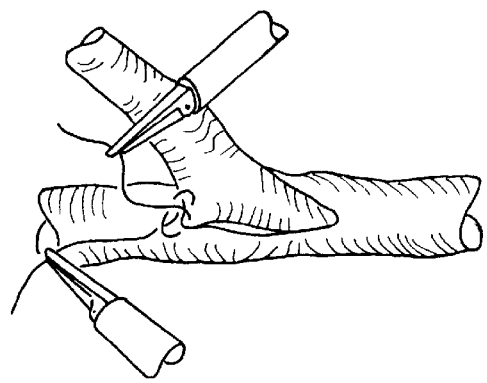
Figure 10D:
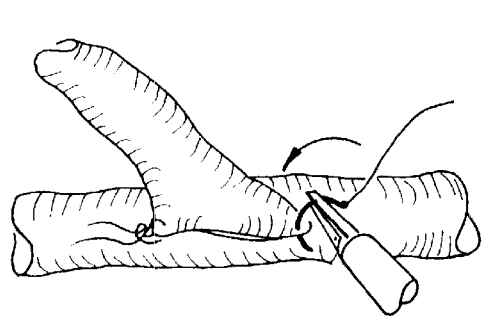
Figure 10E:
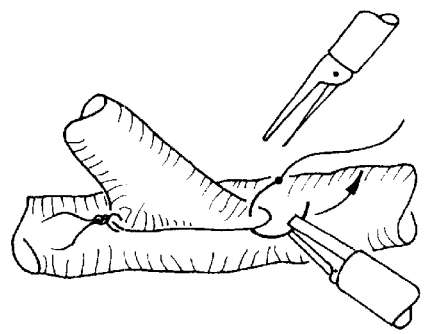
Figure 10F:
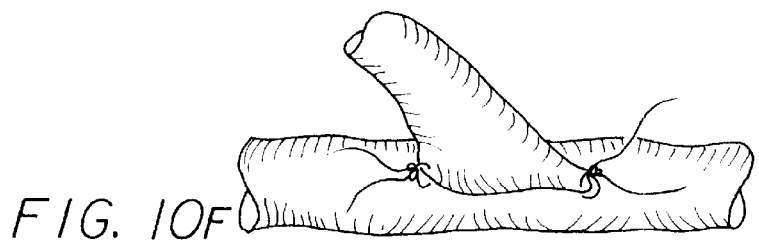
Figure 10G:
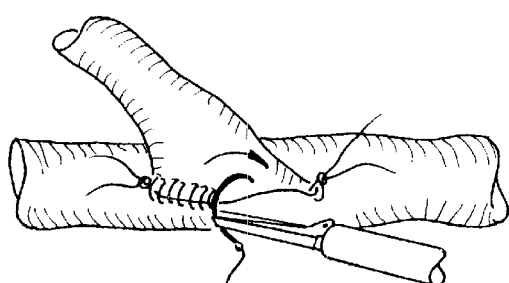
Figure 10H:
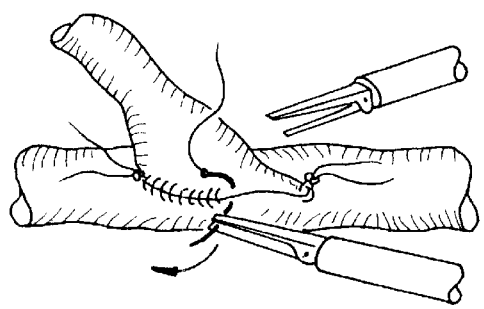
Figure 10I:
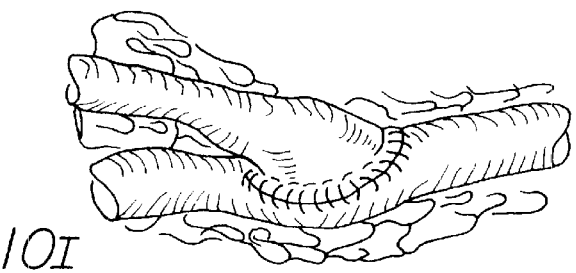

The internal mammary artery (IMA) may be severed and moved by one of the instruments to a graft location of the coronary artery. The coronary artery is severed to create an opening in the artery wall of a size that corresponds to the diameter of the IMA. The incision(s) may be performed by a cutting tool that is coupled to one of the end effectors and remotely manipulated through a master handle. The arteries are clamped to prevent a blood flow from the severed mammary and coronary arteries. The surgeon manipulates the handle to move the IMA adjacent to the opening of the coronary artery. Although grafting of the IMA is shown and described, it is to be understood that another vessel such as a severed saphaneous vein may be grafted to bypass a blockage in the coronary artery. Referring to FIGS. 10A–J, the surgeon moves the handle to manipulate the instrument into driving the needle through the IMA and the coronary artery. The surgeon then moves the surgical instrument to grab and pull the needle through the coronary and graft artery as shown in FIG. 10B. As shown in FIG. 10C, the surgical instruments are then manipulated to tie a suture at the heel of the graft artery. The needle can then be removed from the chest cavity. As shown in FIGS. 10D–F, a new needle and thread can be inserted into the chest cavity to suture the toe of the graft artery to the coronary artery. As shown in FIG. 10H–J, new needles can be inserted and the surgeon manipulates the handles to create running sutures from the heel to the toe, and from the toe to the heel. The scaled motion of the surgical instrument allows the surgeon to accurately move the sutures about the chest cavity. Although a specific graft sequence has been shown and described, it is to be understood that the arteries can be grafted with other techniques. In general the system of the present invention may be used to perform any minimally invasive anastomostic procedure.

Additionally, it may be advantageous to utilize a fourth robotic arm to hold a stabilizer 75. The stabilizer may be a tube or wire or some other medical device that may be emplaced within an artery, vein or similar structure to stabilize such structure. Using the switch 51 to interengage the fourth robotic arm, with a handle 50 or 52 a surgeon may position the stabilizer 75 into the vessel. This eases the task of placing a stitch through the vessel as the stabilizer 75 maintains the position of the vessel. Once the stabilizer 75 has been placed, the surgeon then flips the switch or like mechanism to activate the robotic arm that had been disconnected to allow for movement of the fourth robotic arm. The stabilizer 75 should be substantially rigid and hold its shape. Additionally, the stabilizer should be formed form a material that is steralizable. Such material are well known in the medical arts. However, this application and configuration is heretofore unknown.

As disclosed hereinabove, the system may include a front loading tool driver 84 which receives control signals from the controller 46 in response to movement of a master handle 50 or 52 and drives the tool disposed at the end of a surgical instrument. Alternatively, a back loading tool driver 200 may be incorporated into the system 10 of the present invention, as depicted in FIGS. 15 and 16. The back loading tool driver 200 cooperates with a back loadable surgical instrument 202. The incorporation of such a back loading tool driver 200 and instrument 202 expedites tool changing during procedures, as tools may be withdrawn from the tool driver 200 and replaced with other tools in a very simple fashion.

The back loading tool driver 200 is attached to a robotic arm assembly 26 via a collar and holder as disclosed hereinabove. The back loading tool driver includes a sheath 204 having a proximal end 206 and a distal end 208. The sheath 204 may be formed of plastic or some other well-known material that is used in the construction of surgical instruments. The sheath 204 is essentially a hollow tube that fits through the collar 85 and is tightened in place by the tightening tool that is described in more detail hereinabove.

The back loadable surgical instrument 202 has a tool end 210 and a connecting end 212. A surgical tool 214, such as a grasper or some other tool that may be driven by a push/pull rod or cable system, or a surgical tool that does not require such a rod or cable, such as a coagulator, or harmonic scalpel is disposed at the tool end 210 of the instrument 202.

A housing 216 is disposed at the connecting end 212 of the instrument 202. The housing has a lever 218 disposed interiorly the housing 216. The lever 218 has a pivot point 220 that is established by utilizing a pin passing through an associated aperture 222 in the lever. The pin may be attached to the interior wall 224 of the housing. A push/pull cable or rod 226, that extends the length of the instrument 202 is attached to the lever 218, such that movement of the lever 218 about the pivot point 220 results in a linear movement of the cable or rod 226. Essentially the cable or rod 226 servers as a means 227 for actuating the tool 214 at the tool end 210 of the instrument 202. The cable or rod 226 may be attached to the lever via a connection pin as well. The lever 218 has a C-shape, wherein the ends of the lever 218 protrude through two apertures 228, 230 in the housing 216. The apertures 228, 230 are preferably surrounded by O-rings 232 the purpose of which shall be described in more detail hereinbelow.

The tool end 210 of the back loadable surgical instrument 202 is emplaced in the hollow tube of the back loading tool driver 200. The tool 202 may be pushed through the tool driver until the tool end 210 extends beyond the sheath 204. The O-rings 232 seat in associated apertures 234, 236 in a housing 238 of the tool driver 200. The housing additionally has an aperture 240 centrally formed therethrough, the aperture being coaxial with the interior of the hollow tube. In this fashion, the surgical instrument 202 may be inserted into and through the tool driver 200. Each of the O-rings 232 snugly seats in its associated aperture in the housing 238 of the tool driver 200.

The housing 238 additionally includes a motor assembly 242 which is depicted in FIG. 16. The motor assembly 242 is attached to the housing 238 and is held firmly in place therein. The motor assembly generally includes a motor 244 attached to a reducer 246. The motor drives a leaf 248 attached at the end thereof. The leaf 248 engages the ends of the lever 218 such that rotational movement of the motor results in the movement of the lever 218 about the pivot point 220. This in turn results in the lateral movement of the means 227 for actuating the tool 214 at the tool end 210 of the instrument 202. The motor moves in response to movements at a control handle. Additionally, force sensors 248, 250 may be attached at the ends of the leaf 248. As such, a force feedback system may be incorporated to sense the amount of force necessary to actuate the tool 214 at the tool end 210 of the instrument 202. Alternatively, the motor 244 may have a force feedback device 252 attached thereto, which can be used in a similar fashion.

One advantage of utilizing the back loading tool driver 200 is that the sheath 204 always remains in the patient 12. As such, the tools do not have to be realigned, nor does the robotic arm assembly 26 when replacing or exchanging tools. The sheath 204 retains its position relative to the patient 12 whether or not a toll is placed therethrough.

Figure 29:
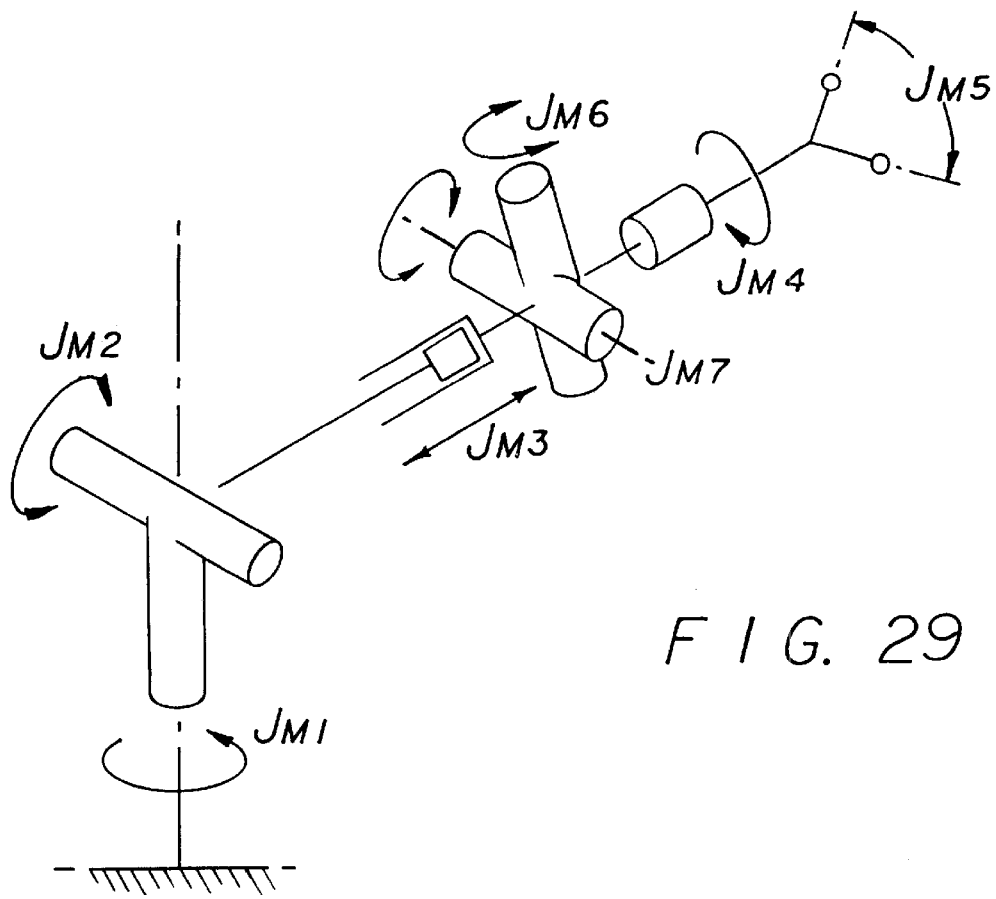
FIG. 29 is an schematic of a master of a system in accordance with the present invention that includes the articulating tool driving assembly.
Figure 30:
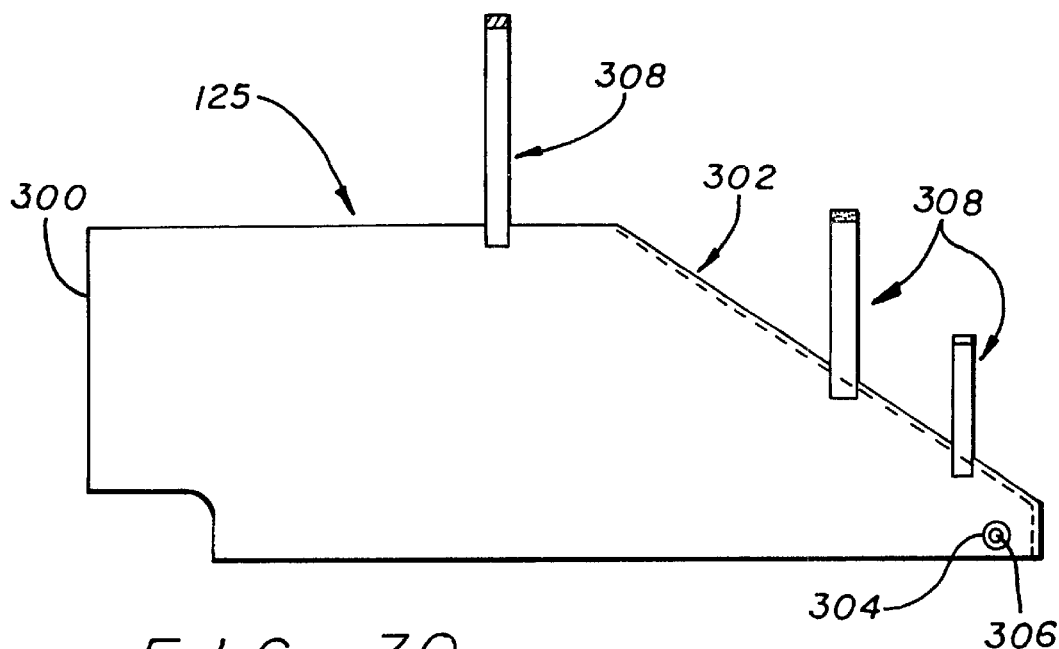
FIG. 30 is a plan view of a drape for use with the robotic arm in accordance with the present invention.

The system 10 of the present invention may additionally be supplied with one or two additional degrees of freedom at the tip of an instrument. For the purposes of example, two additional degrees of freedom will be disclosed; however it is to be appreciated that only one degree of freedom may be included as well. To provide the additional degrees of freedom, and as depicted in FIGS. 17–20, an articulable surgical instrument 300 may be incorporated into the present. The instrument 300 may be coupled to the arm assembly 26 via a collar and holder as disclosed hereinabove. In order to articulate the tip of the articulable instrument 300 an articulating tool driver 500 must be employed. The articulating tool driver 500 shall be described in more detail hereinbelow. The master must have an additional two degrees of freedom added thereto to proved the controls for the articulation at the tip of the instrument 300. FIG. 29 depicts an alternative master schematic that includes the two additional degrees of freedom. As disclosed hereinbelow, the two additional degrees of freedom are mapped to the articulable portion of the instrument 300. The two additional axes at the master are referred to as Jm6 and Jm7.

By incorporating the articulable instrument 300 and the articulating tool driver 500 and the additional degrees of freedom at the master, difficult maneuvers may be carried out in an easier fashion.

With reference to FIGS. 17–20, the articulable instrument 300 generally includes an elongated rod 302, a sheath 304, and a tool 306. The tool can be a grasper, a cutting blade, a retractor, a stitching device, or some other well-known tool used in minimally invasive surgical procedures. FIGS. 27–30 show various tools that may be emplaced at the distal end of the articulable surgical instrument 300.

The instrument 300 includes an articulable portion 301 having a proximal portion 308, a pivot linkage 310 and a distal portion 212 each of which will be discussed in more detail hereinbelow. Additionally, the instrument 300 includes means 311 for articulating the articulable portion 301 of the instrument 300 with respect to the elongated rod 302. The inclusion of the articulable portion 301 provides two additional degrees of freedom at the instrument tip. It must also be appreciated that although the articulable portion 301 is described as including a proximal portion, a pivot linkage and a distal portion, there may be provided a plurality of intermediate portions each mounted to each other via a corresponding pivot linkage.

Disposed between and mounted to each of the respective proximal portion and distal portion and any intervening intermediate portions are pivot linkages 310. The pivot linkage 310 interengages with the proximal and distal portions of the articulable portion to provide articulation at the instrument tip. Essentially, the cooperation of the proximal portion, pivot linkage and distal portion serves as a universal joint.

The elongated rod 302 is preferably hollow and formed of stainless steel or plastic or some other well-know material that is steralizable. Because the rod 302 is hollow, it encompasses and defines an interior 314. The elongated rod 302 additionally has a proximal end 316 and a distal end 318. The distal end 318 of the elongated rod 302 should not be confused with the distal portion 312 of the articulable portion 301 of the instrument 300.

The proximal portion 308 of the articulable portion 301 may be integrally formed with the elongated rod 302 or it may be attached thereto vie welding, glue or some other means well-known to the skilled artisan. It is preferable that the proximal portion 308 be integrally formed with the elongated rod 302 to ensure sufficient stability and durability of the instrument 300. The proximal portion 308 of the articulable portion 301 comprises two fingers 320, 322 each of which have an aperture 324, 326 formed therethrough.

A pivot linkage 310 is mounted to the proximal portion 308 via a plurality of pins 328 that each pass through an associated aperture in an adjoining finger. The pivot linkage 310 is a generally flat disk 330 having a central aperture 332 passing therethrough and four apertures 334, 336, 338, 340 evenly spaced at the periphery of the disk 330. Additionally pins 328 are attached to and extend from the edge 342. The pins 328 seat in the apertures of the associated fingers to provide the articulability of the instrument 300. Five leads 350, 352, 354, 356, 358 extend interiorly the hollow shaft. On lead 350 extends down the center and passes through the center aperture 332 in the pivot linkage 310. Two 352, 354 of the five leads extend down the hollow interior of the instrument and are attached to the pivot linkage such that linear tension on one of the leads results in rotational movement of the pivot portion 301. These two leads 352, 354 attach to the pivot linkage at two of the apertures formed therethrough. Additionally, they attach at those apertures that are adjacent to the pins that pass through the fingers of the proximal portion 308 of the articulable portion 301 of the instrument 300. The other two leads 356, 358 pass through the two other apertures in the pivot linkage and attach at the distal end of the articulable portion 301. Movement of these two leads results in movement of the articulable portion 301 that is orthogonal to the movement when the two other leads 352, 354 are moved.

To articulate the instrument as a part of the present system, and as depicted in FIGS. 21–28, there is provided an articulating mechanism 400. The articulating mechanism 400 generally comprises the articulating tool driver 500, a sterile coupler 600, a translator 700 and the articulable tool 300.

Figure 22:
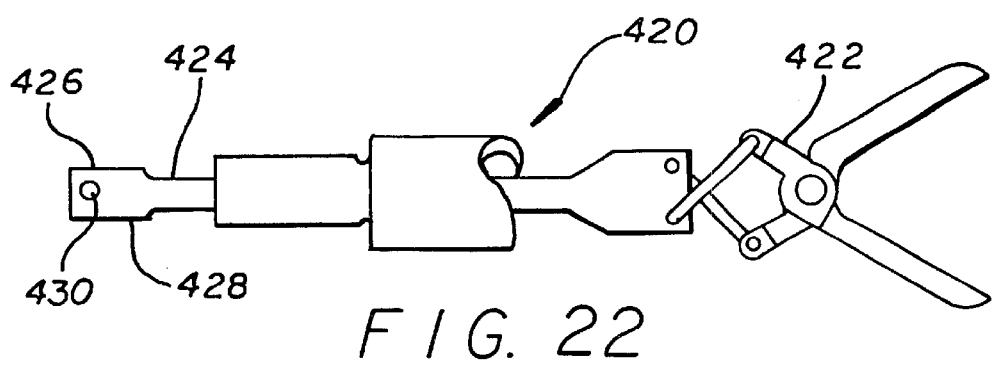
FIG. 22 is a view of a removable tool-tip in accordance with an articulable instrument of the present invention.
Figure 23:
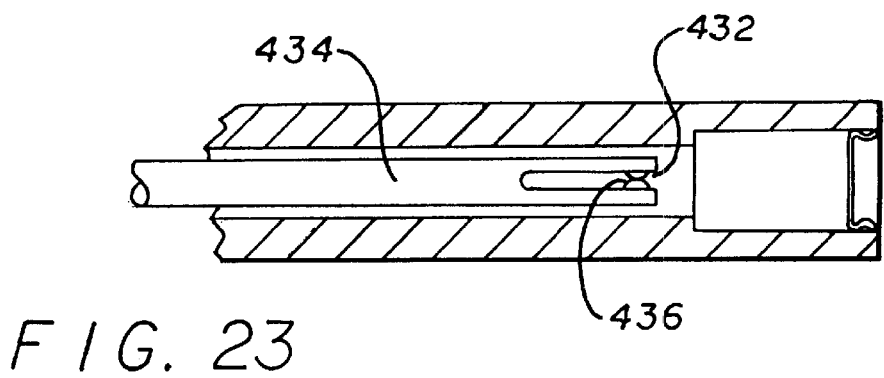
FIG. 23 is a tool-tip receptacle in accordance with the present invention.
Figure 27:
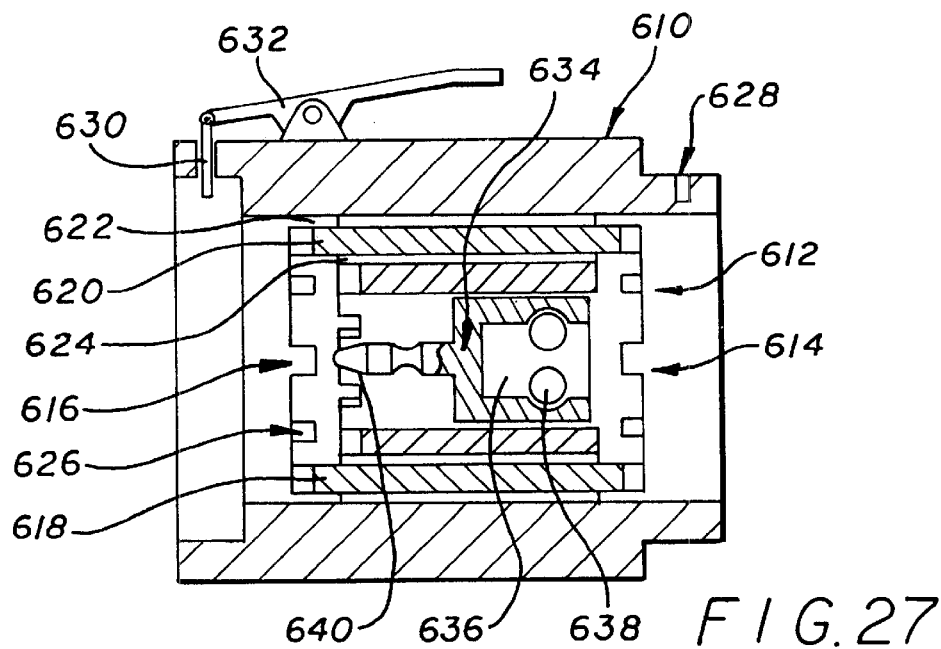
FIG. 27 is a cross-sectional view of the sterile section of the articulating tool driving assembly in accordance with the system of the present invention.
Figure 28:
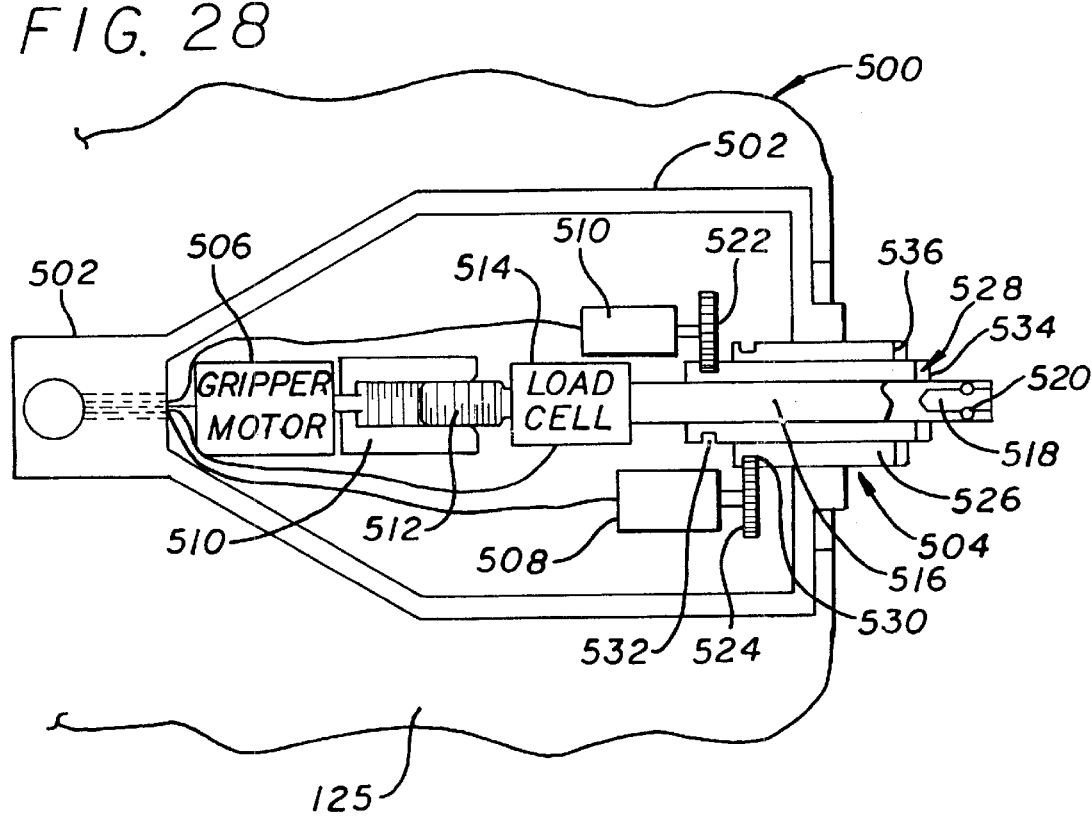
FIG. 28 is a cross sectional view of the tool driver of the articulating tool driving assembly in accordance with the system of the present invention.

The translator is attached to the proximal end 316 of the instrument 300. The instrument 300 may additionally have a removable tool 420 as shown in FIGS. 22–23. The removable tool 420 may be any tool, such as a cutter 422 that is attached to an elongated rod or cable 424. At the end of the rod 246 there is disposed a flat section 428 with an aperture 430 formed therethrough. The flat section 428 seats into a channel 432 disposed at the end of a second cable or rod 434 that travels down the elongated shaft of the instrument 300. The second cable 434 has a channel 432 formed in the end thereof such that the flat section 428 seats in the channel 432. At least one spring biased detent 436 seats in the aperture 430 disposed through the flat section 428. This connects the tool 420 to the rest of the instrument 300. As such, tools may be exchanged at the tip of the instrument without having to remove the instrument from the system 10 every time a new tool is required.

The tool 300 is attached to the translator 700 and essentially is integrally formed therewith. The articulating mechanism 400 is attached to the robotic arm assembly 26 via the collar 85 as is disclosed hereinabove. The collar 85 fits about the shaft 302 of the instrument 300.

The translator 700 has a proximal end 702 and a distal end 704. The distal end 704 of the translator 700 has a cross sectional shape that is substantially similar to the cross sectional shape of the elongated rod 302 of the instrument 300. Additionally, the translator 700 has a hollow interior 706. The center rod 350 extends through the hollow interior 706 of the translator 700 and emerges at the proximal end 702 thereof. Two of the leads 352, 354 terminate interiorly the translator at two shoulders 708, 710 that are attached to a first hollow tube 712 through which the center lead 350 extends. The first hollow tube 712 may be formed of some strong durable material such as stainless steel, steel, hard plastic or the like.

The first hollow tube 712 is mounted to a bearing 714 such that it may be rotated. Rotation of the first hollow tube 712 results in the linear motion of the leads 352, 254 and the articulation of the articulable portion 301 of the instrument 300 in one plane of motion.

A second hollow tube 716 has a pair of shoulders 718, 719 extending therefrom. Two leads 356, 358 attach to one each of the shoulders 718, 719. The hollow tube 716 is disposed within a bearing assembly 720 such that it may be rotated. Again, rotation of the second hollow tube 716 results in linear movement of the leads 356, 358 which articulates the articulable portion 301 of the instrument 300 in a plane orthogonal the plane of motion established through the rotation of the first hollow tube. It is to be appreciated that the second hollow tube 714 radially surrounds the first hollow tube 712. The translator 700 additionally includes a quick disconnect 722 comprising a pin 724 disposed at the end of a spring biased lever 726 which provides removable attachment of the translator 700 to the sterile coupler 600. Both of the hollow tubes 712 and 716 may have notches 750 formed therein at their ends. The notches serve as a means 752 for interconnecting each of the tubes to the sterile coupler 600 which will be discussed in further detail hereinbelow.

The translator 700 is removably attached to the sterile coupler 600 via the quick disconnect 722. Because the articulable tool driver 500 is not easily sterilized, it is advantageous to include a sterile coupler 600 so that instruments may be exchanged without having to sterilize the articulable tool driver 500. Additionally, the coupler 600 provides a means by which the translator 700 may be attached to the tool driver 500 while the tool driver is enclosed in a drape 125 such as that depicted in FIG. 26. The translator 600 has a housing 610. Preferably the housing and the components of the coupler 600 are formed of some easily steralizable mater such as stainless steel, plastics or other well-known sterilizable materials. The housing 610 has a substantially hollow interior 612 and open ends 614 and 616. Two hollow tubes 618 and 620 are rotatively disposed within the housing 610. To effectuate the rotation of each of the tubes 618 and 620, bearings 622 and 624 are disposed about each of the tubes. Each of the tubes has notches 626 formed in the ends thereof so effectuate the attachment of the translator 700 to the coupler 600 at one end. And to effectuate the attachment of the coupler 600 to the articulable tool driver 500 at the other end thereof.

The pin 724 on the translator may seat in a notch 628 to attach the translator 700 to the coupler 600. Additionally, the coupler 600 may include a pin 630 attached to a spring biased pivot 632 to effectuate attachment of the coupler to the driver 500. The coupler 600 additionally includes a center section 634 that slidably receives the end 351 of the center cable or rod 350. The end 351 may include a tip with a circumferential groove 353 disposed thereabout. The tip seats in a recess 636 formed in the center section 634 and is removably locked in place by at least one spring biased detent 638. A tip 640, which is substantially similar to the tip containing the circumferential groove 353 is disposed adjacent the recess 636 and serves to attach the cable center cable 350 to the articulable tool driver 500, which will be discussed in further detail hereinbelow.

The center section 634 is intended to laterally slide within the innermost tube 618. To effectuate such a sliding motion, a linear bearing may be disposed about the center section interiorly of the innermost tube. Alternatively, the center section 634 may be formed of a bearing material that provides smooth sliding within the innermost tube 618.

The coupler 600 is removably attached to the articulable tool driver 500. It is intended that the articulable tool driver be enclosed by a drape 125. The articulable tool driver 500 includes a substantially hollow housing 502 having a closed first end 504 and a substantially open second end 504. Securely disposed interiorly the housing 502 is a gripper motor 506, and a pair of wrist motors 508 and 510. Each of the motors are in electrical connection with the controller 46. Alternatively, the motors may receive signals from the controller via a transmitter/receiver system where such systems are well known. It is the application of such a transmitter/receiver system to the present invention that is new. The gripper motor 506 is attached to a load nut 510 that surrounds a load screw 512. The motor 506 receives the control signals and turns in response thereto. The load nut 510 turns which laterally moves the load screw 512. The load screw 512 is attached to a load cell 514 which may be employed to measure the force required to laterally move the cable 350 which is attached vie the coupler 600 to the gripper motor 506. This may be used in a force feedback system that may be incorporated in the system 10 of the present invention. A rod 516 having a channel 518 formed at the end thereof is attached to the load cell 514. As such, the rod 516 moves in a linear fashion. The tip 640 of the coupler 600 seats in the channel 518 and is removably held in place by at least one spring biased detent or some other similar attachment mechanism 520. Therefore, if a surgeon at a master handle actuates the grippers, the gripper motor 506 turns, thus laterally moving the rod 516, and in turn the center cable 350 which opens and closes the grippers at the tool accordingly. Of course, the action at the tool will depend upon the type of tool disposed thereat. For example, if a stapling tool is disposed at the end of the surgical instrument 300 then a stapling action would take place.

If a master handle 50 or 52 is turned about axes J6 or J7 then one of the two wrist motors 510, 508 corresponding to the required motion turns. Each of the motors 508, 510 are attached to a corresponding gear 522, 524. Each of the gears 522, 524 engage a corresponding slotted section 530, 532 of an associated hollow tube 526, 528 to turn the associated tube radially about its longitudinal axis. Each of the tubes 526, 528 include notched ends 534, 536 to engage the notched ends of corresponding hollow tubes of the coupler 600. It is to be appreciated that each of the hollow tubes 526, 528, 618 and 620 are all coaxial. Additionally, bearings may be emplaced intermediate each of the tubes 526 and 528 to provide easy independent rotatability of the individual tubes.

When the tubes 526, 528 are rotated, they rotate the tubes in the coupler which rotates the tubes in the translator. This results in the articulation at the tip of the surgical instrument 300. More particularly, this results in the articulation of the articulable portion of the surgical instrument 300. Additionally, whether the front loading tool driver, the back loading tool driver, or the articulable tool driver are employed, surgical instruments may be easily exchanged.

As such, a cutting blade 800 may be exchanged for a grasper, and a grasper may be exchanged for a stapler 810. Essentially, such a system simplifies the performance of minimally invasive surgical procedures where the procedures include the step of changing one tool for another. And because the system allows articulation at the tip of certain instruments, the articulation mechanism may be used to articulate such stapling, or cutting instruments that incorporate the articulable portion as disclosed hereinabove.

Figure 31:
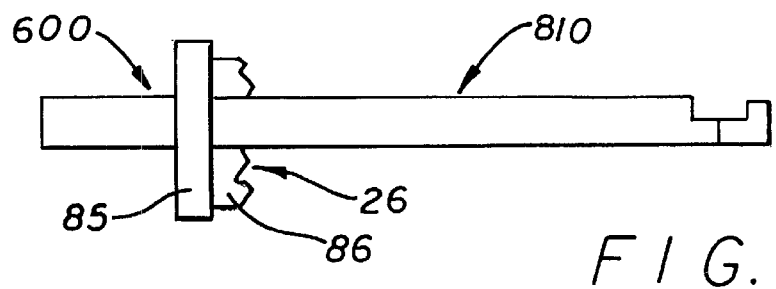
FIG. 31 is a plan view of a surgical instrument having a stapling tool disposed at the end thereof and wherein the surgical instrument is attached to the robotic arm in accordance with the present invention.

Additionally, the instrument may not be an articulable instrument, but the articulating mechanism can be used to control other functions, such as stapling. FIG. 31 depicts a stapling instrument 810 attached to the robotic arm assembly via the collar 85 and holder 86. The lead that is generally use for the grasping tool, may be used to effectuate the stapling mechanism. Endoscopic staplers are generally well known in the art, however, it is heretofore to known to use a stapler that is attached to a robotic arm as is disclosed herein.

Figure 32:
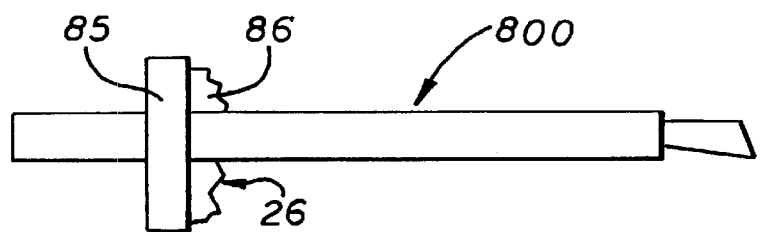
FIG. 32 is a plan view of a surgical instrument having a cutting blade disposed at the end thereof wherein the instrument is attached to the robotic arm in accordance with the present invention.
Figure 33:
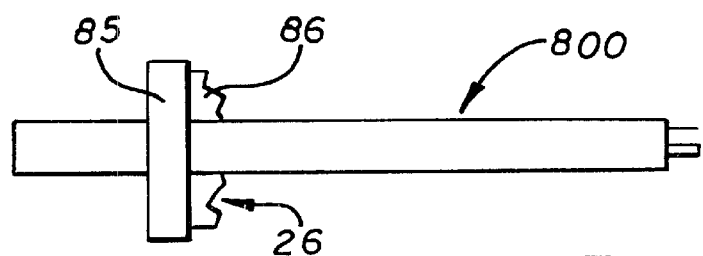
FIG. 33 is a plan view of a surgical instrument having a coagulating/cutting device disposed at the end thereof, the instrument attached to a robotic arm in accordance with the present invention.
Figure 34:
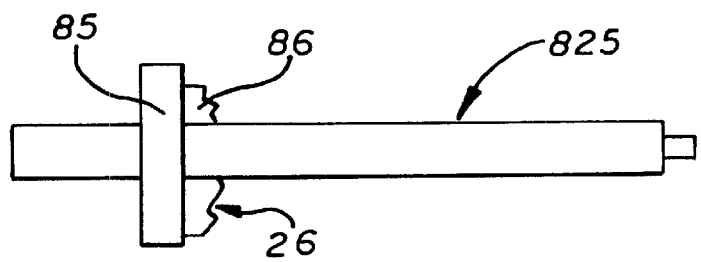
FIG. 34 is a plan view of a surgical instrument having a suturing tool disposed at the end thereof and wherein the surgical instrument is attached to the robotic arm in accordance with the present invention.
Figure 40A:
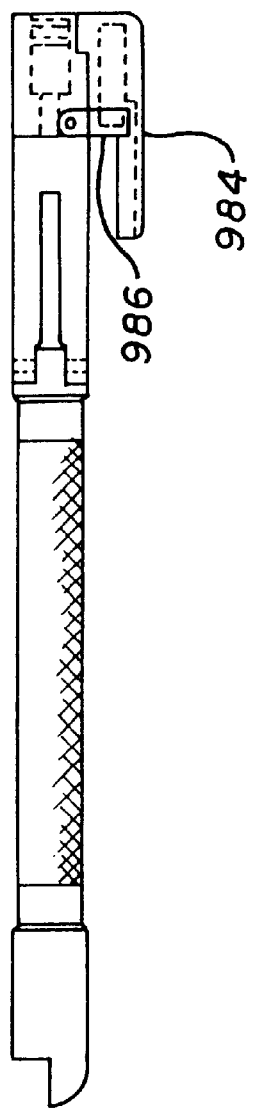
FIG. 40A is a top plan view which shows an interchange mechanism of the handle shown in FIG. 40.
Figure 40:
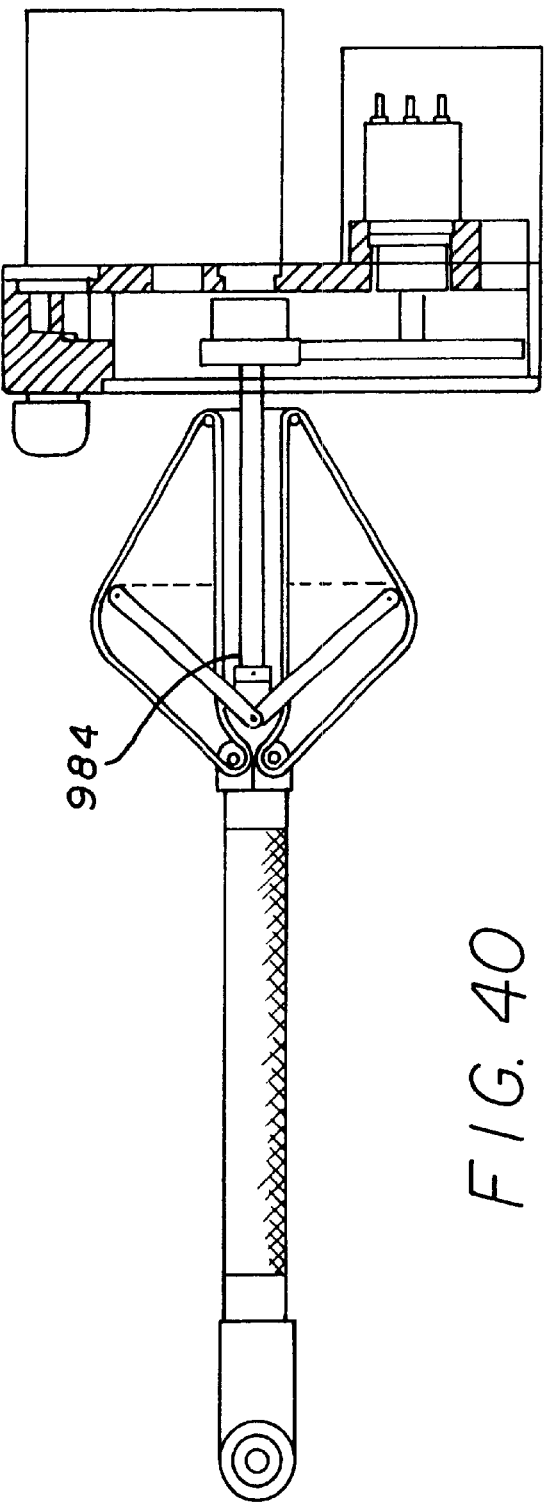
FIG. 40 is a top plan cross-sectional view of the handle depicted in FIG. 39.

Additionally, a cutting blade, such as that depicted in FIG. 32 may be employed in the system of the present invention. The cutting blade 800 is attached to the robotic arm assembly 26 via the collar 85 and holder 86. The cutting blade does not require a lead such as that required by the grasper or the stapler; however, the cutting tool, may be articulated via the articulating mechanism that has been disclosed hereinabove.

A cauterizer or coagulator may additionally be attached to the robotic arm assembly 26 via the collar 85 and holder. Cauterizers and coagulators are well known and the cauterizing tool may be attached at the end of an articulable instrument as disclosed hereinabove. By using a variety of tools in predetermined sequences, various procedures may be carried out. It is generally preferable to be able to change instruments because many procedures require such.

As disclosed hereinabove, the handles 50 and 52 allow a surgeon to control the movement of the tools attached to the robotic arms. As such, the configuration of the handles 50 and 52 should provide great ease of use for a surgeon. FIGS. 38–43 depict various handle configurations. Additionally, the handles 50 and 52 may be selected by a surgeon from a plurality of handles 960 that are available for use by the surgeon.

A proximally open handle 962 has a proximal end 963 and a distal end 965. The handle 962 has first finger portion 964 and a second finger portion 966 pivotally attached at the distal end 965 of the handle 962. A joint 968 disposed intermediate the finger portion 964 and 966 provides linear motion of an elongated rod 970 which is used to actuate the tool tip of an instrument attached to the robotic arm. This handle may serve as one or both of the two handles 50 and 52 of the system.

A distally open handle 972 has a proximal end 973 and a distal end 975. The handle 972 has first finger portion 974 and a second finger portion 976 pivotally attached at the proximal end 973 of the handle 972. A joint 978 disposed intermediate the finger portion 964 and 966 provides linear motion of an elongated rod 980 which is used to actuate the tool tip of an instrument attached to the robotic arm. This handle may serve as one or both of the two handles 50 and 52 of the system.

Such handles 962 and 972 may be interchanged through the inclusion of an interchange mechanism 984. The interchange mechanism 984 includes a biased detent latch 986 that engages an aperture in the elongated rod 932 such that the handle may be attached or removed from the rod 932.

Figure 43:
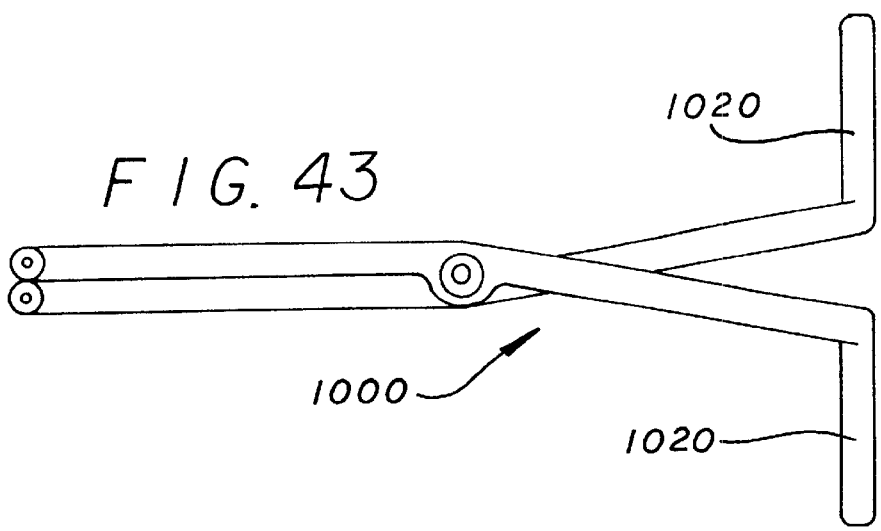
FIG. 43 is an alternative embodiment of a handle in accordance with the present invention.
Figure 41:
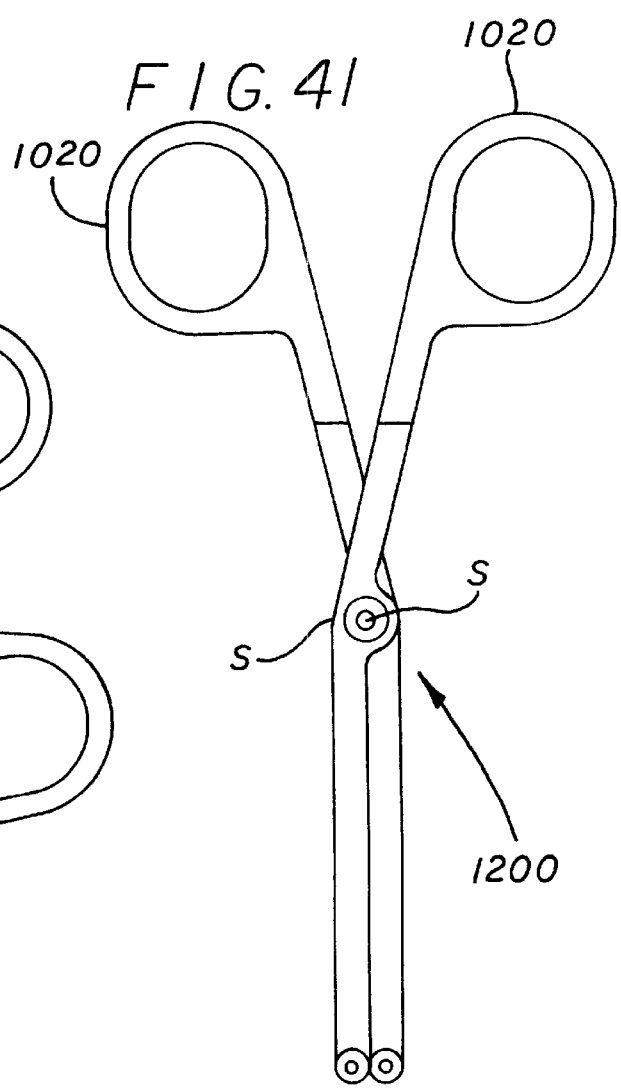
FIG. 41 is an alternative embodiment of a handle in accordance with the present invention.
Figure 42:
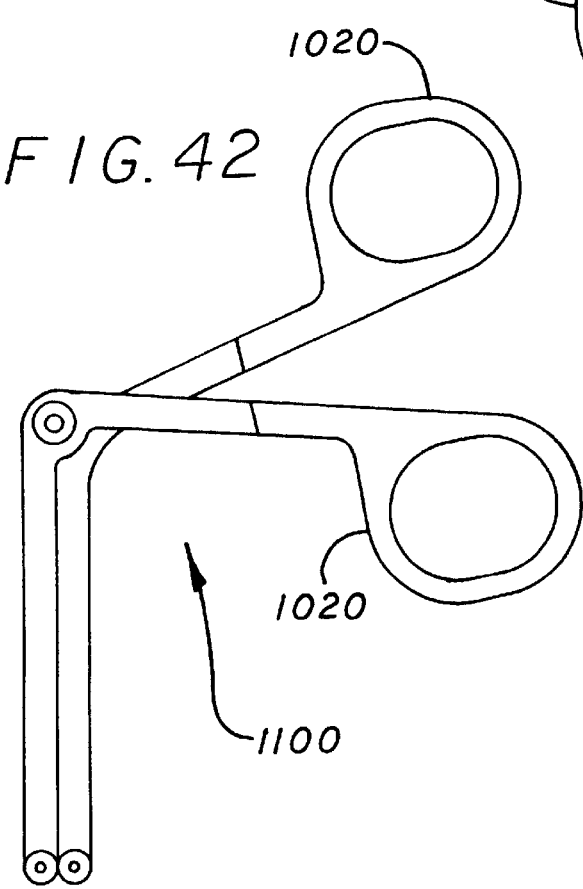
FIG. 42 is an alternative embodiment of a handle in accordance with the present invention.

Other handle configurations are depicted in FIGS. 41–43. And more particularly, each of the handles 1000, 1100, and 1200 have a pair of fingerseats 1020. The major difference between each of the handles 1000, 1100, and 1200 is the orientation of the fingerseats to a pivot point on the handle. The fingerseats may be parallel, or perpendicular to the axis S of the pivot point of the handle. Each of these configurations may be included as an attachable handle. As such, a surgeon may exchange handles throughout a procedure depending upon the task to be accomplished. A surgeon may prefer one handle for a set of tasks and another handle for a different set of tasks. As such, the surgeon may exchange handles during the performance of a surgical procedure to enable such tasks.

While certain exemplary embodiments have been described and shown in the accompanying drawings, it is to be understood that such embodiments are merely illustrative of and not restrictive on th broad invention, and that this invention not be limited to the specific constructions and arrangements shown and described, since various other modifications may occur to those ordinarily skilled in the art.

FIG. 44 shows an embodiment of a surgical instrument 1600 that is coupled to a tool driver 1602. The instrument 1600 may have an end effector 1604 that is actuated by the tool driver 1602. The tool driver 1602 can be connected to a controller (not shown) by a wire assembly 1606. Additionally, the tool driver 1602 can be coupled to an articulate arm 1608. The articulate arm 1608 can both move the tool driver 1602 and spin the instrument 1600.

As shown in FIG. 45, the tool driver 1602 may include a sheath 1610 that is attached to a tool housing 1612. The sheath 1610 may include a sleeve portion 1614 that extends from a collar 1616. The collar 1616 may have internal threads (not shown) that are screwed onto corresponding threads (not shown) of the housing 1612 so that the sheath can be detached from the housing 1612. The sheath 1610 may be constructed from a material that is both electrically non-conductive and transparent to x-rays.

The electrically non-conductive material may prevent electrical current from flowing to the patient from the surgical instrument. By way of example, if the instrument is an electro-cautery device the non-conductive sheath may prevent an electrical short through the sheath. As an alternate embodiment, the sheath 1610 may be constructed from a metal material that has an outer layer of non-conductive material. Providing a sheath 1610 that is transparent to x-rays allows x-ray images of the patient to be taken without interference from the sheath.

The sheath 1610 is typically inserted into an incision of a patient. The sheath 1610 and incision define a pivot point for the instrument 1600. The articulate arm 1608 may include passive joints which provide additional degrees of freedom for the arm (not shown). The sheath 1610 provides a structure that may hold the arm 1608 in place when a new instrument 1600 is being coupled to the tool driver 1602.

FIG. 46 shows an embodiment of the sheath collar 1616. The collar 1616 may include a valve assembly 1620 that can move between an open position and a closed position. A gas is typically introduced into the patient when performing a procedure with the surgical instrument 1600. The valve 1620 prevents gas from escaping the patient and flowing through a sheath inner channel 1622 when the instrument 1600 is pulled out of the sheath 1610.

The valve assembly 1620 may include a valve 1624 that controls fluid communication between a valve port 1626 and the inner channel 1622. The valve 1624 may be coupled to a torsion spring 1628 that biases the valve 1624 into the closed position. In the closed position the valve 1624 may cooperate with a valve seat 1630 to prevent gas from flowing through the inner channel 1622 and into the port 1626. The valve 1624 may have a radial portion 1632 and an annular flat portion 1634 that presses against the seat 1630.

As shown in FIG. 47, the instrument 1600 can be inserted through the port 1626 and into the inner channel 1622. The port 1626 may have a tapered surface 1636 to guide the instrument 1600 through the valve 1624. Insertion of the instrument 1600 into the sheath 1610 pushes the valve 1624 into the open position. The seat 1630 may have a wiper 1638 that presses against the outside surface of the instrument 1600 and prevents gas from escaping the patient through the valve assembly 1620. The wiper 1638 may have an inner diameter that is approximately equal to the outer diameter of the surgical instrument 1600 so that there is a slip fit between the wiper 1638 and the instrument 1600. The valve 1624 may not make contact with the wiper 1638 even in the closed position.

Figure 48:
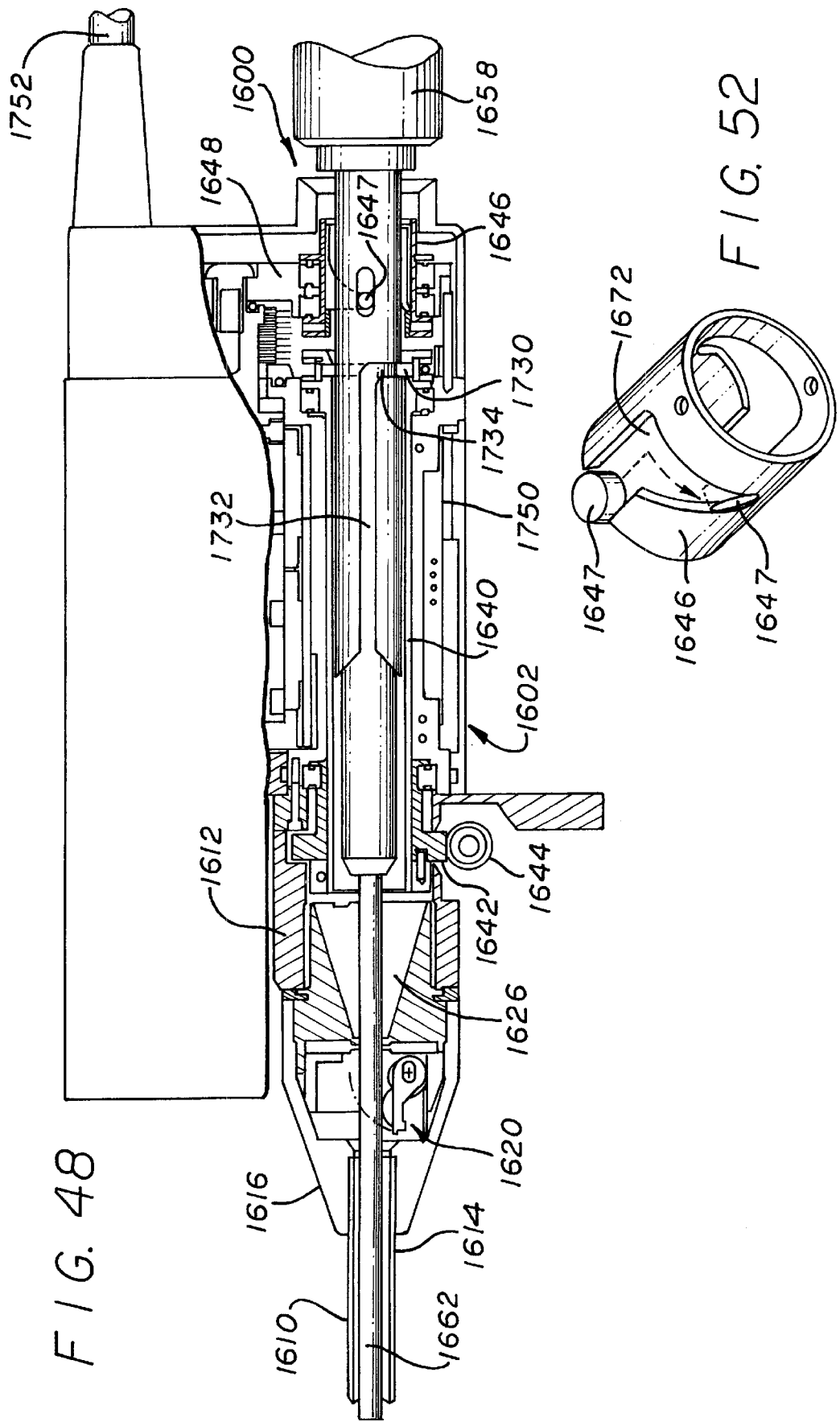
FIG. 48 is a cross-sectional view showing a surgical instrument coupled to a tool holder.
Figure 49:
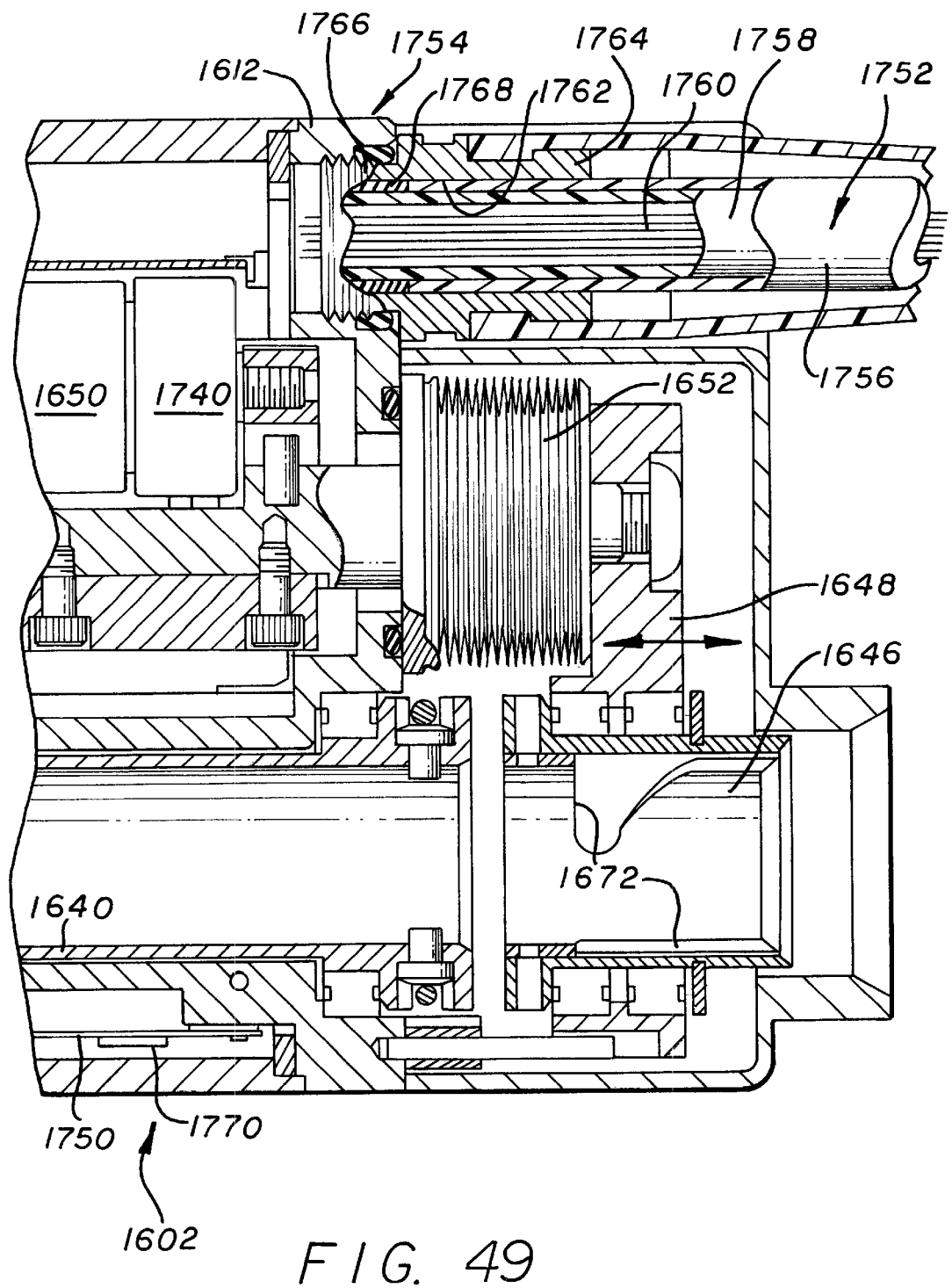
FIG. 49 is an enlarged cross-sectional view of the holder without an instrument.

As shown in FIGS. 48 and 49, the tool driver 1602 may include a tube 1640 that is coupled to the surgical instrument 1600. The tube 1640 may have gear teeth 1642 that are coupled to a mating gear 1644 of the articulate arm 1608 (also shown in FIG. 45). The mating gear 1644 can be rotated by a motor (not shown) in the arm 1608. Rotation of the gear 1644 rotates the worm gear 1642 and the tube 1640. Rotation of the tube 1640 rotates the instrument 1600 within the patient.

The driver 1602 may include an inner sleeve 1646 that is coupled to an actuator pin 1647 of the instrument 1600. The sleeve 1646 is attached to a plate 1648. The plate 1648 is coupled to a linear actuator 1650. The actuator 1650 can move the plate 1646 along the longitudinal axis of the tube 1640 as indicated by the arrow. Movement of the plate 1648 translates the sleeve 1646 and pin 1647 to actuate the end effector 1604 of the instrument 1600. The inner sleeve 1646 is coupled to the plate 1648 so that the sleeve 1646 can spin within the instrument 1600.

The tool driver 1602 may include a bellows 1652 that couples the linear actuator 1650 to the plate 1648. The bellows 1652 seals the interface so that the actuator of the driver 1602 does not become contaminated. In one embodiment, the bellows 1652 is constructed from a stainless steel material which is particularly suitable for reuse when the tool driver 1604 is sterilized under elevated pressures and temperatures.

FIG. 50 shows an embodiment of a surgical instrument 1600 that can be coupled to the tool driver 1602. The instrument 1600 may have a push rod 1654 that extends through the inner channel 1656 of a handle 1658. The push rod 1654 may be coupled to a detachable actuator rod 1660. The actuator rod 1660 extends through an instrument sleeve 1662 and terminates at the end effector 1604.

The actuator pin 1647 may be pressed into the push rod 1654. The pin 1647 is free to move along a slot 1666 of the handle 1658. As shown in FIG. 51 the actuator pin 1647 may include a pair of caps 1668 that snap onto a barbed pin 1670. The caps 1668 secure the pin 1670 to the push rod 1654.

As shown in FIG. 52, when the instrument 1600 is installed into the driver 1602 the pin assembly 1664 engages a corresponding groove 1672 of the sleeve 1646. Movement of the sleeve 1646 by the linear actuator 1650 translates the pin 1647 and the attached actuator rod 1660 to provide a controlled movement of the end effector 1604.

As shown in FIG. 53, the actuator rod 1660 may have a proximal extension 1674 that engages a clamp portion 1676 of the push rod 1654. The extension 1674 and clamp 1676 allow the actuator rod 1654 and corresponding end effector to be detachably connected to the handle 1658. The clamp portion 1676 may include four barbed tips 1678 that essentially enclose a locking cavity 1680. The locking cavity 1680 may receive a locking barrel 1682 located at the end of the extension 1674.

The extension 1674 can be inserted through an opening 1684 of the handle 1658. The locking barrel 1682 engages chamfered surfaces 1686 of the barbed tips 1678 to deflect the tips 1678 in an outward direction and allow the barrel 1682 to be inserted into the locking cavity 1680. The locking cavity 1680 has a profile which prevents the barrel 1682 from becoming detached from the push rod 1654. A collar 1688 can be screwed onto a threaded portion 1690 to capture a collar of the instrument sleeve 1662 and secure the sleeve 1662 to the handle 1658.

The actuator rod 1660 can be removed by moving the push rod 1654 until the chamfered surfaces 1686 of the tips 1678 engage an annular lip 1692 of the handle 1658. The annular lip 1692 deflects the tips 1678 so that the actuator rod 1660 can be separated from the push rod 1654. The collar 1688 is typically initially removed to decouple the instrument sleeve 1662 from the handle 1654. The clamp arrangement allows different end effectors to be attached to the same handle 1654 during a surgical procedure without having to decouple the entire instrument 1600 from the tool driver 1602.

Figure 54:
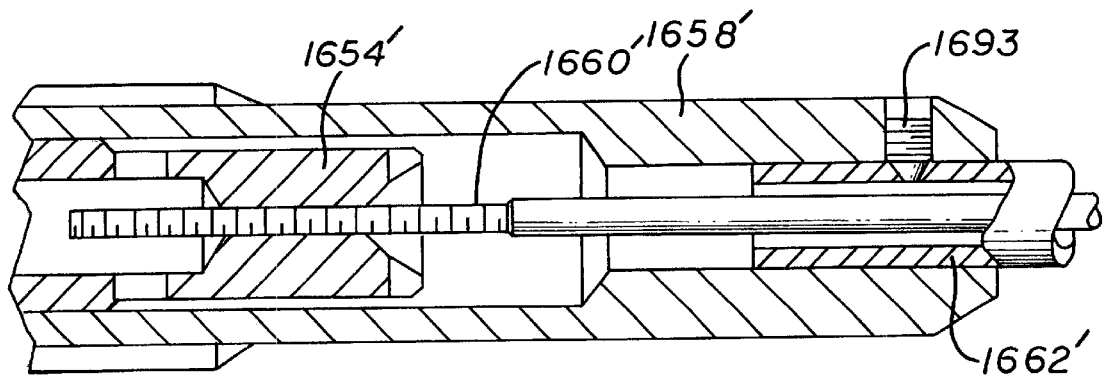
FIG. 54 is a cross-sectional view of an alternate embodiment of a connector assembly.

FIG. 54 shows an alternate embodiment wherein the actuator rod 1660' is screwed into a push rod 1654'. The instrument sleeve 1662' may be connected to the handle 1658' by a set screw 1693.

Referring again to FIG. 50, the push rod 1654 may be attached to a plunger 1694 by a pin 1696. The plunger 1694 allows an operator to manually move the push rod 1654 into the annular lip 1692 shown in FIG. 53 so that the end effector 1604 can be replaced with another unit. The instrument 1600 may include a return spring 1698 that biases the plunger 1694 into a proximal position. The spring 1698 can also insure that the end effector 1604 is always closed or open, whatever is desired, when the end effector 1604 is removed from the patient.

The instrument 1600 may include a detachable electrode 1700 that is attached to the push rod 1654. The electrode 1700 can be attached to an electrical power supply (not shown). The push rod 1654, actuator rod 1660 and electrode 1700 can all be constructed from an electrically conductive material which provides an electrical path between the power supply and a cauterizing element(s) on the tip of a cauterizing type instrument. The handle 1658 and plunger 1694 may be constructed from an expensive disposable non-conductive plastic material.

Figure 55:
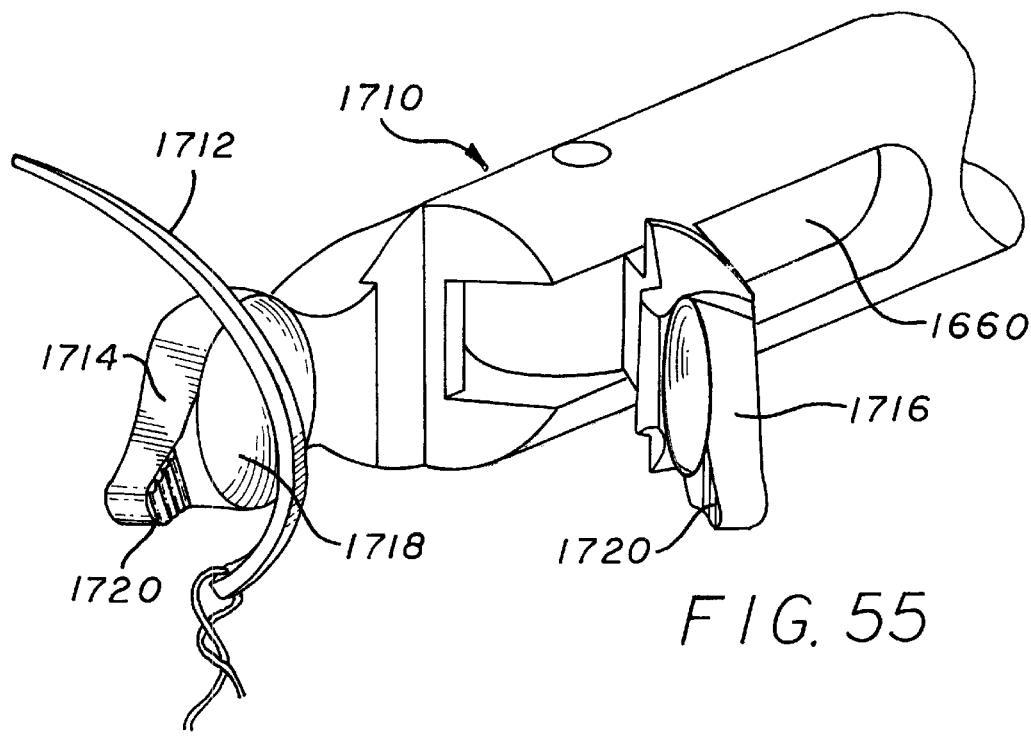
FIG. 55 is a perspective view of an embodiment of an effector.

FIG. 55 shows an embodiment of an end effector 1710 which can be used to grasp a needle 1712. The end effector 1710 may have a stationary finger 1714 and a clamp finger 1716 that is moved by the actuator rod 1660. The stationary finger 1714 may have an outer surface 1718 which has a radius of curvature that conforms to the shape of the needle 1712. The end effector 1710 can be manipulated so that the needle 1712 extends along the outer surface 1718. The needle 1712 is held in place by moving the clamp finger 1716 to a closed position. The outer surface 1718 is preferably oriented to be essentially perpendicular to the longitudinal axis of the push rod 1660 so that the needle 1712 can be moved in any direction in space. Each finger 1714 and 1716 may have a tip 1720 can be used to grasp tissue.

Figure 56:
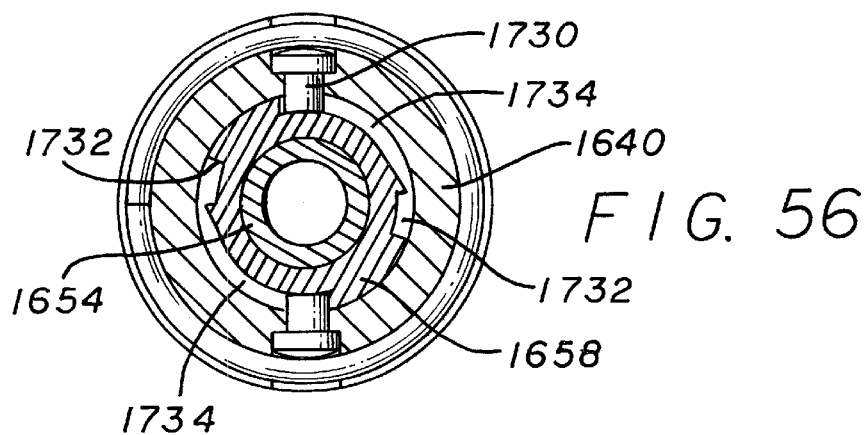
FIG. 56 is a cross-sectional view of a pin/slot interface of the tool driver and instrument.

Referring to FIGS. 48 and 56, show an interface which secures the handle 1658 to the sleeve 1662 and tube 1640 of the driver 1602. The tube 1640 may have a plurality of spring biased ball detents 1730 which can slide along corresponding alignment grooves 1732 of the handle 1658. The grooves 1732 may each have transverse portions 1734 which receive the detents 1730 when the handle 1658 is turned in a counter-clockwise direction. The detents 1730 and grooves 1732 align the instrument 1600 with the driver 1602 so that the actuator pin 1647 is aligned with the grooves of the sleeve 1646.

Referring to FIG. 48 the tool driver 1602 may include a force sensor 1740 which senses the force exerted onto the end effector. The force sensor 1740 can be coupled to a controller (not shown) which can utilize the feedback as part of an algorithm to control the instrument.

The mechanical advantage may vary for different surgical instruments. For example, the force ratio between the handle and tip of a hand-held tweezer may be 2/5, while the ratio for a needle grasper may be 5/1. It may be desirable to provide the following variable force transformation algorithm to allow an operator to vary the force ratio between the handle held by the hand of the surgeon and the tip of the instrument. This provides the surgeon with a more realistic "feel" of an instrument that is normally held by the surgeon. The force algorithm may be as follows.

$$F_t = R \cdot (F_{h-K} \cdot \theta)$$

where;

$F_t$=force at the instrument tip.
R=variable force ratio.
$F_h$=force applied by the opeartor on the handle.
K spring constant for instrument jaw.
θ=angle of instrument jaw.
The ratio R may be defined by;

$$R = \frac{F_{tm}}{F_{hm} - K \cdot \theta}$$

where;

$F_{tm}$=nominal maximum tip force.
$F_{hm}$=nominal maximum handle force.

Each instrument coupled to the tool driver may have a corresponding R value that is utilized by the controller to provide a tip force which corresponds to a handle force that is similar to the ratio of a corresponding instrument that is normally held in the hand of a surgeon.

By way of example, if the instrument coupled to the driver corresponds to a tweezer, an appropriate R value can be loaded into the controller so that two pounds of force exerted onto the handle will translate into 5 pounds of force at the tip of the end effector. Likewise, 5 pounds of forces sensed by the force sensor will translate into 2 pounds of feedback to the handle. The R value can be entered through an input device such as a keypad, voice recognition system, etc., or automatically called up from an electronically stored lookup table when the instrument 1600 is coupled to the driver 1602.

Referring to FIG. 49, the driver 1602 may include a printed circuit board assembly 1750 that is connected to the linear actuator 1650 and the force sensor 1740. The printed circuit board assembly 1750 may be coupled to the controller by a wire assembly 1752. The wire assembly 1752 is introduced to the driver 1602 through a connector port 1754.

The wire assembly 1752 may include an outer jacket 1756 that encloses an inner jacket 1758. The inner jacket 1758 may enclose electrical wires 1760. The inner jacket 1758 may be constructed from a non-porous material such as TEFLON. The outer jacket 1756 may be constructed from a flexible material such as silicon.

The outer jacket 1758 may extend through an inner channel 1762 of a sleeve 1764 that is screwed into the driver housing 1612. The sleeve 1764 may be sealed against the housing by an O-ring 1766. The assembly 1752 may further include a sealant 1768 that seals the inner jacket 1758 to the outer jacket 1756 within the sleeve 1764. The dual jackets and seals insure that moisture does not enter the tool driver through the wire assembly when the driver is sterilized.

The printed circuit board assembly 1750 may include a temperature sensor 1770. By way of example, the tool driver 1602 may be sterilized after each surgical procedure under elevated temperatures and pressures. During sterilization the sensor 1770 may be connected to an instrument (not shown) through the wire assembly 1752. The instrument may provide a readout of the temperature within the tool driver 1602 to allow an operator to determine whether the driver temperature exceeds a threshold value that may damage the driver. Alternatively, or in addition to, the instrument may provide an indicator, such as the illumination of light, when the temperature exceeds a threshold value.

Figure 57:
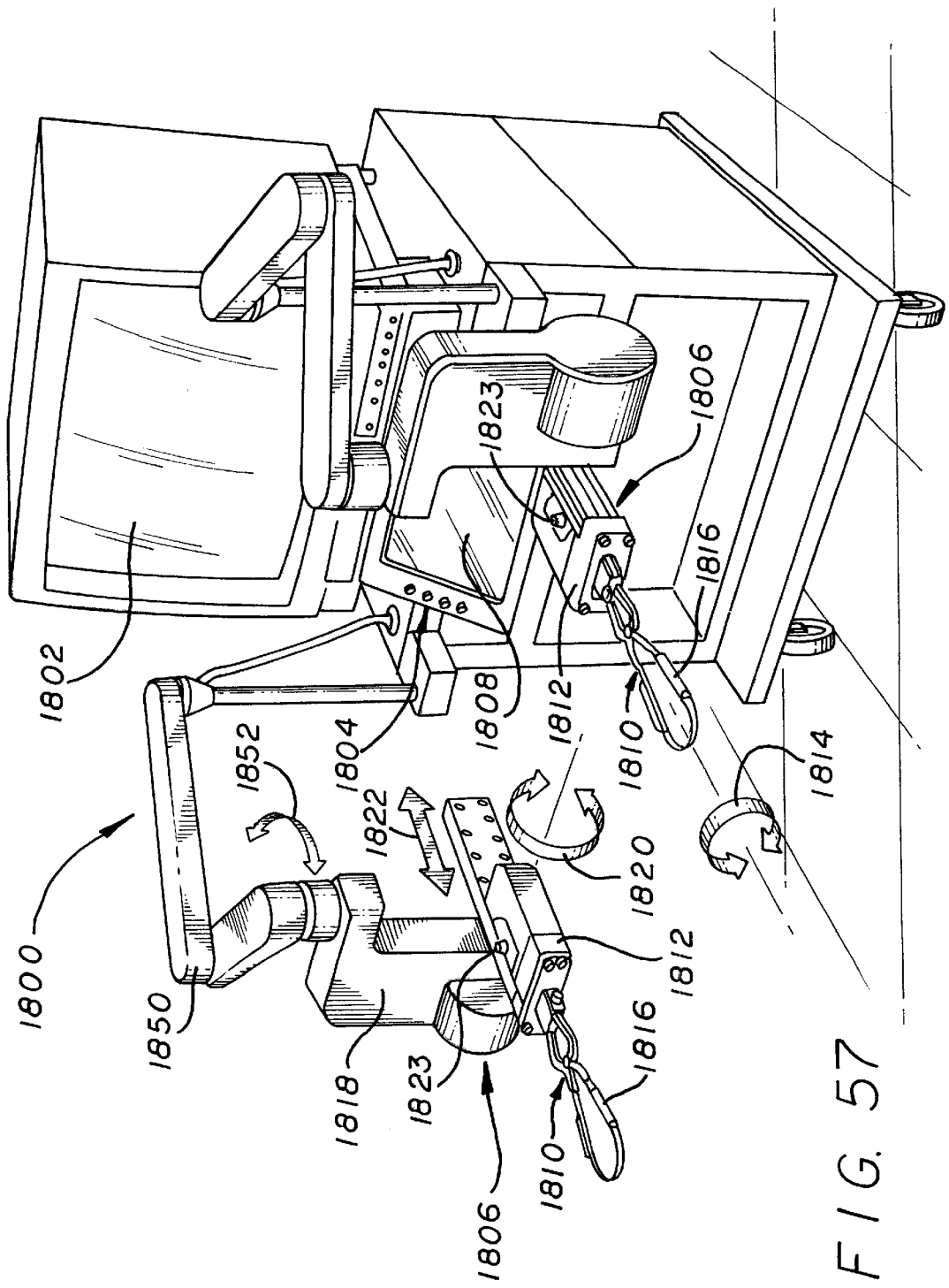
FIG. 57 is a perspective view of an embodiment of a console.

FIG. 57 shows an embodiment of a console 1800 for the system. The console 1800 may include a video monitor 1802, an input device 1804 and a pair of handle assemblies 1806. The handles 1806 can be manipulated to control the surgical instrument (not shown). The input device 1804 may include a touchpad screen 1808 which displays a menu(s), commands and other information which allow an operator to vary different operating parameters of the systems by pressing the screen 1808.

By way of example, the touchpad 1808 may allow the operator to vary the force ratio value R, or a scale factor that correlates the amount of spacial movement between the handles and the instrument. The operator may also select between a pull type surgical instrument and a push type instrument. A push type instrument may require a distal movement of the actuator rod to close the end effector. A pull type instrument may require an opposite proximal movement of the actuator rod to close the end effector. Selecting push or pull insures that the tool driver will properly actuate the instrument. The operator may also control the maximum jaw angle of the instrument and a jaw locking option wherein the instrument jaw remains locked even when the operator releases the handle.

Each handle assembly 1806 may include a grasper 1810 that can spin relative to a handle 1812 as indicated by arrow 1814. Rotation of the grasper 1810 can be translated into a corresponding spinning movement of the instrument about the instrument longitudinal axis. The grasper 1810 may contain a pair of pressure plates 1816 that can be depressed by the operator. The depression of the plates 1816 can cause a corresponding movement of the actuator rod and the end effector of the instrument.

The handle 1812 can be pivoted and translated relative to a swing arm 1818 as indicated by the arrows 1820 and 1822, respectively. Pivoting the handle 1812 may provide a corresponding rotational movement of the instrument within the patient. Likewise, translational movement of the handle 1812 may induce a movement of the instrument into and out of the patient. The handle 1812 may have a release button 1823 which can be depressed to decouple the handle assembly 1806 from the instrument, such that movement of the assembly 1806 will not create a corresponding movement of the instrument.

Figure 58:
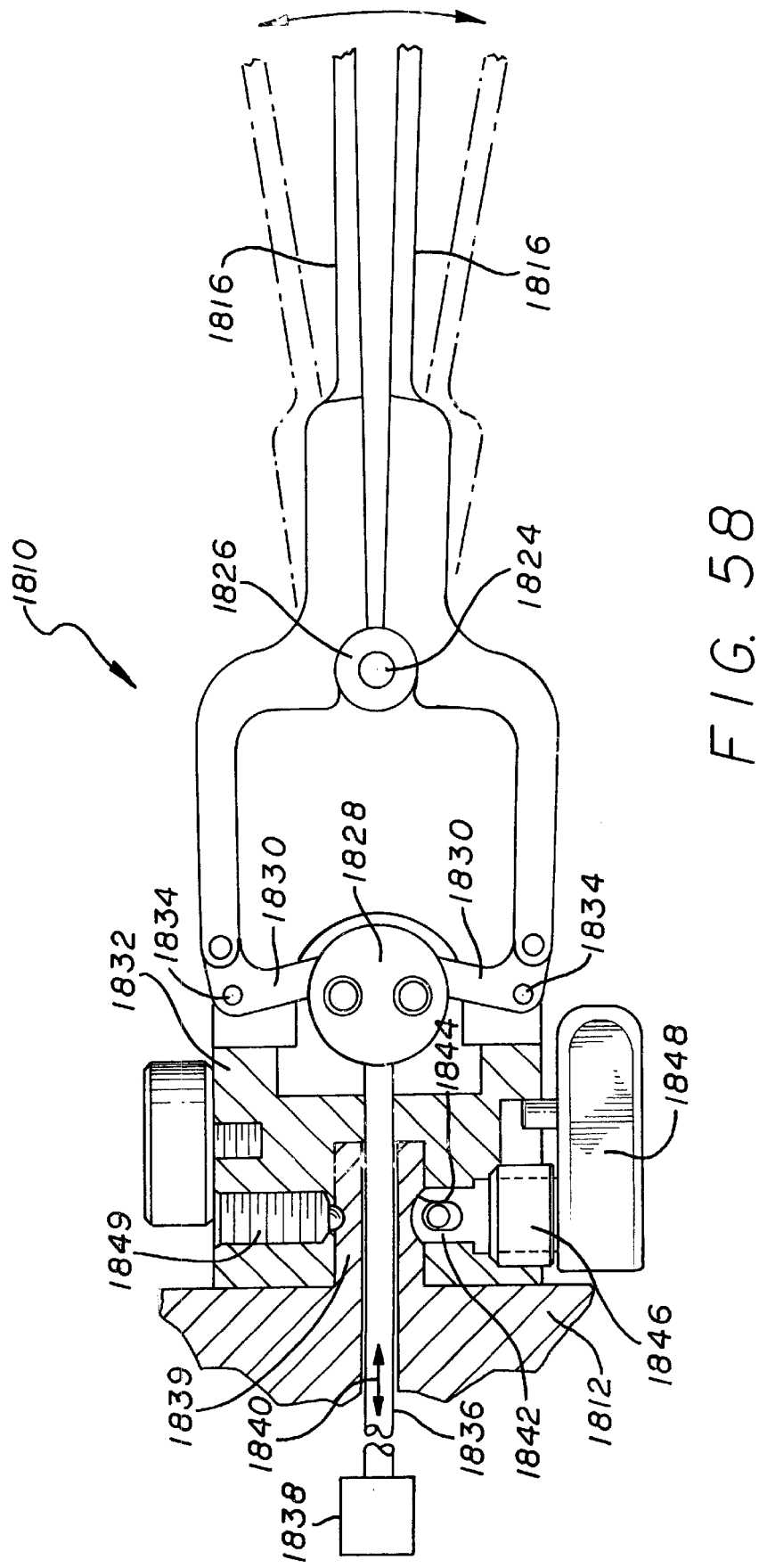
FIG. 58 is a cross-sectional view of a grasper of a handle assembly.

FIG. 58 shows an embodiment of the grasper 1810. The pressure plates 1816 can be pivotally connected together by a pin 1824 and bushing 1826. The plates 1816 are also connected to a push ring 1828 by a pair of rocker arms 1830. The rocker arms 1830 are pivotally connected to a grasper housing 1832 by pins 1834. The push ring 1828 is connected to a push rod 1836.

The push rod 1836 is connected to an actuator/sensor assembly 1838 that can translate the rod 1836 and ring 1828 as indicated by the arrow 1840. The actuator/sensor assembly 1838 can either induce or sense the translational movement of the rod 1836. Movement of the rod 1836 can either induce, or be responsive to, deflection of the plates 1816. The plates 1816, ring 1828, rod 1836 and actuator/sensor assembly 1838 allow the system to both sense the force being applied by the operator and apply a feedback force to the operator.

The push rod 1836 may be coaxial aligned with a connector rod 1839 that is used to couple the grasper 1810 to the handle 1812. The connector rod 1839 is locked in place by a connecting pin 1842 that sits within a corresponding groove 1844 of the rod 1840. The pin 1842 is attached to a threaded collar 1846 and a handle 1848. The handle 1848 can be rotated to move the pin 1842 into engagement with the connector rod 1836 to "frictionally" lock the rod 1836 to the grasper 1810. The grasper 1810 may also have a spring biased ball detent 1849 which mates with a corresponding feature of the rod 1840 to properly orient the grasper 1810 with the handle 1812.

Referring to FIG. 57, the swing arm 1818 can pivot about a forearm 1850 as indicated by arrow 1852. Pivotal movement of the swing arm 1818 may induce a corresponding movement of the instrument. The forearm may be adjusted to a desirable position by the operator.

FIG. 59 shows an embodiment of the swing arm 1818. The swing arm handle 1812 may include a sliding bearing assembly 1860 which allows an operator to slide the handle 1812 relative to the arm 1818. The handle 1812 may have cables (not shown) that are coupled to a roller 1862. The roller 1862 rotates in conjunction with any linear displacement of the handle 1812. Rotation of the roller 1862 can be detected by a rotational sensor 1864 that is connected to the controller of the system. The sensor 1864 can provide output signals that are processed to induce a corresponding movement of the instrument.

Translation of the handle 1812 may move the center of gravity of the assembly 1806. The assembly 1806 may include a counterweight assembly 1866 that counteracts the movement of the handle 1812 so that the handle assembly 1806 is mechanically balanced.

The counterweight assembly 1866 may include a counterweight 1868 that is coupled to a translator 1870. The translator 1870 causes the counterweight 1868 to move in a direction opposite from the movement of the handle 1812 to counteract the shifting weight of the handle 1812.

The counterweight 1868 may be connected to a roller 1872 that is coupled to a variable torque assembly 1874. The variable torque assembly may include an actuator 1876 that is connected to a linkage mechanism 1878. The linkage mechanism 1878 includes a finger plate 1880 that exerts a force on the roller 1872 and the counterweight 1868.

As shown in FIG. 60 the roller 1872 can move along the finger plate 1880. Movement of the roller 1872 varies the effective lever arm and corresponding torque exerted by the counterweight to counteract an opposite movement of the handle 1812. The output of the actuator 1876 can be varied to change the force exerted by the plate 1880 and torque applied by the counterweight 1868.

Figure 61:
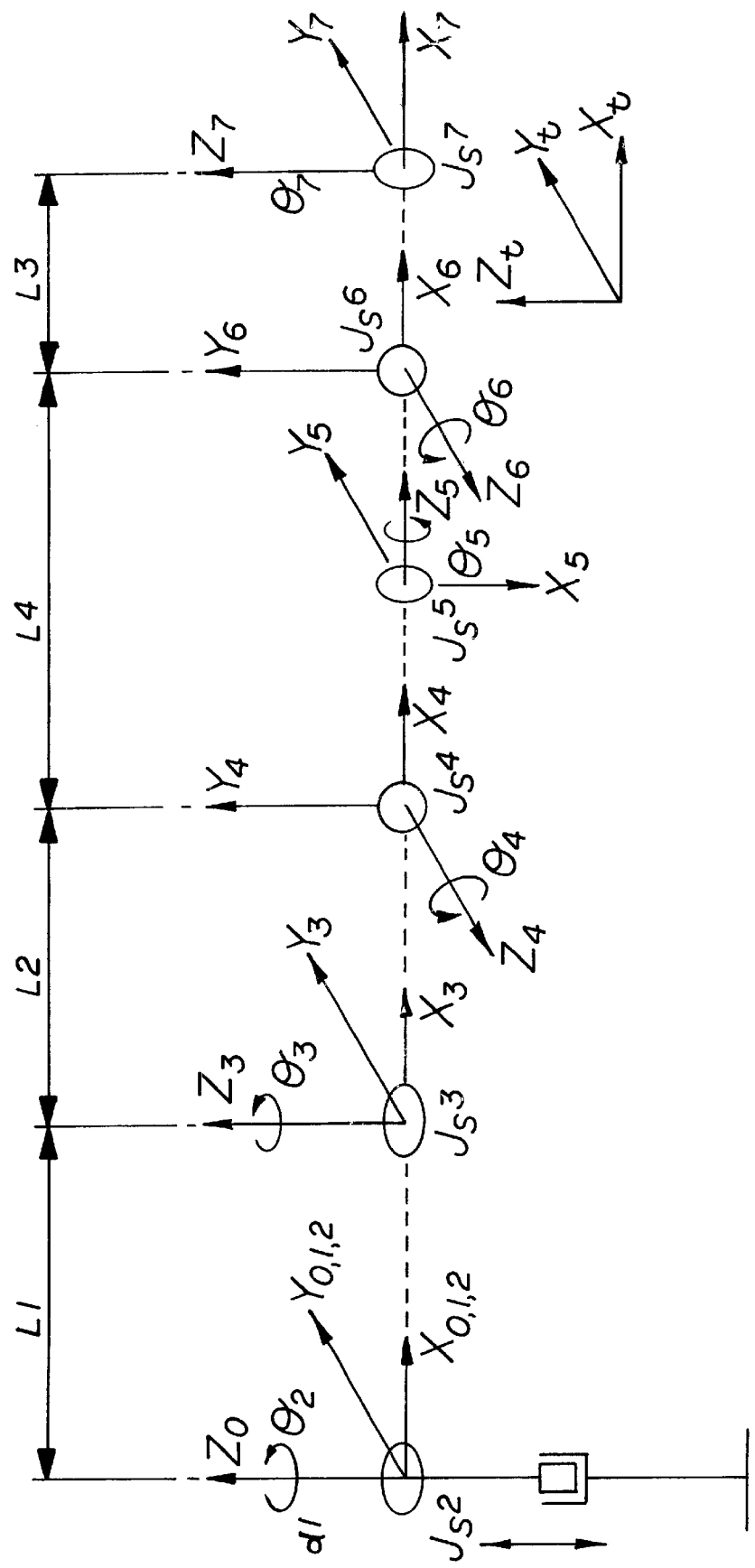
FIG. 61 is a schematic of an articulate arm of the system.

FIG. 61 shows a schematic of an articulate arm that corresponds to the arm shown in FIG. 3. When performing a cardiac surgical procedure it may be desirable to insert a surgical instrument into a patient and then move the tip of the instrument up toward the patient's sternum. The active actuator $J_{s4}$ will allow the instrument to move in such a manner.

The articulate arm can be located within nine different Cartesian coordinate systems designated by subscripts 0, 1, 2, 3, 4, 5, 6, 7 and t. The zero coordinate system is a fixed world system. The first coordinate system has an origin at the center of the first rotary motor $J_{s2}$. The origin can move along a z direction a distance d1. The x and y unit vectors of the first coordinate system do not vary regardless of the position of the first linkage arm $L_1$.

The second coordinate system has an origin at the center of the first rotary motor $J_{s2}$ but has x and y unit vectors that rotate with rotation of the first linkage arm $L_1$. The third, fourth, fifth, sixth and seventh coordinate systems correspond to the centers of joints $J_{s3}$, $J_{s4}$, $J_{s5}$ and $J_{s6}$ and $J_{s7}$, respectively. Joints $J_{s3}$, $J_{s4}$ and $J_{s7}$ may all be active. Joints $J_{s5}$ and $J_{s6}$ may be passive.

The tip of the instrument may be located within a tip coordinate system $X_t$, $Y_t$ and $Z_t$. A movement of the tip in a desired direction may be translated back into the world coordinate system $X_0$, $Y_0$ and $Z_0$ utilizing the following forward transformation matrices. The transformation matrix $T_0^1$ ransforms world coordinates into the coordinates of the first coordinate system, $T_1^2$ transforms the first coordinates into the second coordinate system and so forth and so on.

$$T_0^1 = \begin{pmatrix} 1 & 0 & 0 & 0 \\ 0 & 1 & 0 & 0 \\ 0 & 0 & 1 & d_1 \\ 0 & 0 & 0 & 1 \end{pmatrix}$$

$$T_1^2 = \begin{pmatrix} \cos\theta_2 & -\sin\theta_2 & 0 & 0 \\ \sin\theta_2 & \cos\theta_2 & 0 & 0 \\ 0 & 0 & 1 & 0 \\ 0 & 0 & 0 & 1 \end{pmatrix}$$

-continued $$T_2^3 = \begin{pmatrix} -\cos\theta_3 & -\sin\theta_3 & 0 & L_1 \\ \sin\theta_3 & \cos\theta_3 & 0 & 0 \\ 0 & 0 & 1 & 0 \\ 0 & 0 & 0 & 1 \end{pmatrix}$$

$$T_3^4 = \begin{pmatrix} -\cos\theta_4 & -\sin\theta_4 & 0 & L_2 \\ 0 & 0 & -1 & 0 \\ \sin\theta_4 & \cos\theta_4 & 0 & 0 \\ 0 & 0 & 0 & 1 \end{pmatrix}$$

$$T_4^t = \begin{pmatrix} 1 & 0 & 0 & L_4 \\ 0 & 0 & 1 & 0 \\ 0 & -1 & 0 & 0 \\ 0 & 0 & 0 & 1 \end{pmatrix}$$

$$T_t^5 = \begin{pmatrix} 0 & 0 & 1 & 0 \\ \sin\theta_5 & \cos\theta_5 & 0 & 0 \\ -\cos\theta_5 & \sin\theta_6 & 0 & 0 \\ 0 & 0 & 0 & 1 \end{pmatrix}$$

$$T_5^6 = \begin{pmatrix} -\sin\theta_6 & -\cos\theta_6 & 0 & 0 \\ 0 & 0 & -1 & 0 \\ \cos\theta_6 & -\sin\theta_6 & 0 & 0 \\ 0 & 0 & 0 & 1 \end{pmatrix}$$

$$T_6^7 = \begin{pmatrix} \cos\theta_7 & -\sin\theta_7 & 0 & L_3 \\ 0 & 0 & 1 & 0 \\ -\sin\theta_7 & -\cos\theta_7 & 0 & 0 \\ 0 & 0 & 0 & 1 \end{pmatrix}$$

The inverse of the above listed transformation matrices can be used to provide the following equations which define the amount of movement for each actuator for a desired movement of the instrument tip.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A surgical instrument, comprising:
   a handle;
   a push rod that is coupled to and movable relative to said handle, said push rod defining a locking cavity therein;
   an actuator rod detachably coupled to said push rod, said actuator rod including a locking barrel that is located within the locking cavity of said push rod when said actuator rod is coupled to said push rod; and,
   an end effector that is coupled to said actuator rod.

2. The instrument of claim 1, wherein said handle defines an inner channel, said push rod being movable within the inner channel of the handle, said handle including a plunger that is coupled to said push rod for decoupling the actuator rod from the push rod, said instrument further including a return spring that biases the plunger into a proximal position.

3. The instrument of claim 1, wherein said push rod includes a plurality of tips, that can be deflected into an open position to allow said locking barrel to be inserted into said locking cavity, and move back into a closed position to capture said locking barrel.

4. The instrument of claim 3, wherein said handle includes a lip that can engage and deflect said tips so that said locking barrel can be pulled out of said locking cavity.

5. The instrument of claim 4, further comprising a plunger that is coupled to said push rod and which can be depressed to move said tips into engagement with said lip so that said locking barrel can be pulled out of said locking cavity.

6. The instrument of claim 5, further comprising a spring that biases said plunger into a proximal position.

7. The instrument of claim 6, further comprising a pin that is attached to said push rod and which can move within a slot of said handle.

8. The instrument of claim 7, further comprising an instrument sleeve that is attached to said handle, wherein said actuator rod extends through said instrument sleeve.

9. The instrument of claim 1, wherein said handle includes an alignment groove.

10. The instrument of claim 9, wherein said alignment groove includes a transverse portion.

11. The instrument of claim 1, further comprising an electrode that is attached to said push rod and electrically connected to said end effector.

12. A surgical instrument, comprising:
    a handle;
    a push rod that can move relative to said handle;
    an actuator rod that is coupled to said push rod;
    an end effector that is coupled to said actuator rod; and,
    a plunger that is attached to said push rod and coupled to said handle, said plunger can be depressed so that said actuator rod can be detached from said push rod.

13. The instrument of claim 12, wherein said actuator rod includes a locking barrel that can be located within a locking cavity of said push rod.

14. The instrument of claim 13, wherein said push rod includes a plurality of tips, that can be deflected into an open position to allow said locking barrel to be inserted into said locking cavity, and move back into a closed position to capture said locking barrel.

15. The instrument of claim 14, wherein said handle includes a lip that can engage and deflect said tips when said plunger is depressed so that said locking barrel can be pulled out of said locking cavity.

16. The instrument of claim 12, further comprising a spring that biases said plunger into a proximal position.

17. The instrument of claim 12, further comprising a pin that is attached to said push rod and which can move within a slot of said handle.

18. The instrument of claim 12, wherein said handle includes an alignment groove.

19. The instrument of claim 18, wherein said alignment groove includes a transverse portion.

20. The instrument of claim 12, further comprising an instrument sleeve that is attached to said handle, wherein said actuator rod extends through said instrument sleeve.

21. The instrument of claim 12, further comprising an electrode that is attached to said push rod and electrically connected to said end effector.

22. A surgical instrument, comprising:
    a handle having an inner channel;
    a push rod coupled to the inner channel of the handle;
    an end effector; and
    an actuator rod that is coupled to the end effector and is detachably coupled to the push rod without using a tool, wherein said push rod is movable relative to the handle to actuate the end effector.

23. The instrument of claim 22, wherein said actuator rod includes a locking barrel that is located within a locking cavity of said push rod.

24. The instrument of claim 23, wherein said push rod includes a plurality of tips that are deflectable into an open position to allow said locking barrel to be inserted into said locking cavity, and movable back into a closed position to capture said locking barrel.

25. The instrument of claim 24, wherein said handle includes a lip that can engage and deflect said tips so that said locking barrel can be pulled out of said locking cavity.

26. The instrument of claim 25, further comprising a plunger that is coupled to said push rod, said plunger being depressible to move said tips into engagement with said lip so that said locking barrel can be pulled out of said locking cavity.

27. The instrument of claim 26, further comprising a spring that biases said plunger into a proximal position.

28. The instrument of claim 27, further comprising a pin that is attached to said push rod and which can move within a slot of said handle.

29. The instrument of claim 28, further comprising an instrument sleeve that is attached to said handle, wherein said actuator rod extends through said instrument sleeve.

* * * * *